United States Patent
Anceriz et al.

(10) Patent No.: US 12,365,731 B2
(45) Date of Patent: Jul. 22, 2025

(54) NKP46 BINDING AGENTS

(71) Applicant: INNATE PHARMA, Marseilles (FR)

(72) Inventors: Nadia Anceriz, Aubagne (FR); Mathieu Blery, Marseilles (FR); Laurent Gauthier, Marseilles (FR); Carine Paturel, Marcy l'Etoile (FR)

(73) Assignee: INNATE PHARMA, Marseilles (FR)

( * ) Notice: Subject to any disclaimer, the term of this patent is extended or adjusted under 35 U.S.C. 154(b) by 390 days.

(21) Appl. No.: 17/852,419

(22) Filed: Jun. 29, 2022

(65) Prior Publication Data

US 2022/0340661 A1    Oct. 27, 2022

Related U.S. Application Data

(62) Division of application No. 16/478,863, filed as application No. PCT/EP2018/051394 on Jan. 22, 2018, now Pat. No. 11,377,492.

(60) Provisional application No. 62/530,443, filed on Jul. 10, 2017, provisional application No. 62/449,617, filed on Jan. 24, 2017.

(51) Int. Cl.
| | |
|---|---|
| *A61P 35/00* | (2006.01) |
| *A61K 47/68* | (2017.01) |
| *A61P 37/02* | (2006.01) |
| *C07K 16/28* | (2006.01) |
| *C07K 16/30* | (2006.01) |
| *G01N 33/569* | (2006.01) |

(52) U.S. Cl.
CPC .... *C07K 16/2803* (2013.01); *A61K 47/68035* (2023.08); *A61K 47/6849* (2017.08); *A61P 35/00* (2018.01); *C07K 16/30* (2013.01); *G01N 33/56972* (2013.01); *C07K 2317/33* (2013.01); *C07K 2317/732* (2013.01); *C07K 2317/92* (2013.01)

(58) Field of Classification Search
CPC ............ C07K 16/2803; C07K 16/30; C07K 2317/732; C07K 2317/92; C07K 2317/24; A61K 47/6849; A61P 35/00; A61P 37/02
USPC ....................................... 424/139.1
See application file for complete search history.

(56) References Cited

U.S. PATENT DOCUMENTS

| 11,001,629 B2 | 5/2021 | Gauthier et al. |
| 11,377,492 B2 | 7/2022 | Anceriz et al. |
| 2021/0269523 A1 | 9/2021 | Gauthier et al. |

FOREIGN PATENT DOCUMENTS

| WO | WO 2015/015489 | 2/2015 |

OTHER PUBLICATIONS

Peters, C. et al. "Antibody-drug conjugates as novel anti-cancer chemotherapeutics" *Bioscience Reports*, Jun. 12, 2015, pp. 1-20, vol. 35, No. 4, Art. e00225.
Mellor, J. D. et al. "A critical review of the role of Fc gamma receptor polymorphisms in the response to monoclonal antibodies in cancer" *Journal of Hematology & Oncology*, 2013, pp. 1-10, vol. 6, No. 1.
Shemer-Avni, Y. et al. "Expression of NKp46 Splice Variants in Nasal Lavage Following Respiratory Viral Infection: Domain 1-Negative Isoforms Predominate and Manifest Higher Activity" *Frontiers in Immunology*, Feb. 15, 2017, pp. 1-10, vol. 8, Article 161.
Written Opinion in International Application No. PCT/EP2018/051394, Aug. 20, 2018, pp. 1-12.
Byers, T. "What Can Randomized Controlled Trials Tell US About Nutrition and Cancer Prevention" *CA Cancer Journal for Clinicians*, 1999, pp. 353-361, vol. 49, No. 6.

*Primary Examiner* — Yan Xiao
(74) *Attorney, Agent, or Firm* — SALIWANCHIK, LLOYD & EISENSCHENK

(57) ABSTRACT

The present invention provides antigen-binding proteins capable of binding to NKp46 polypeptides. The antigen-binding proteins have increased activity in the treatment of disorders characterized by NKp46-expressing cells, particularly tumor cells.

9 Claims, 5 Drawing Sheets
Specification includes a Sequence Listing.

SEQUENCE LISTING

```
<160> NUMBER OF SEQ ID NOS: 78

<210> SEQ ID NO 1
<211> LENGTH: 304
<212> TYPE: PRT
<213> ORGANISM: homo sapiens

<400> SEQUENCE: 1

Met Ser Ser Thr Leu Pro Ala Leu Leu Cys Val Gly Leu Cys Leu Ser
1               5                   10                  15

Gln Arg Ile Ser Ala Gln Gln Gln Thr Leu Pro Lys Pro Phe Ile Trp
            20                  25                  30

Ala Glu Pro His Phe Met Val Pro Lys Glu Lys Gln Val Thr Ile Cys
        35                  40                  45

Cys Gln Gly Asn Tyr Gly Ala Val Glu Tyr Gln Leu His Phe Glu Gly
    50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
            100                 105                 110

Leu Asp Leu Val Val Thr Glu Met Tyr Asp Thr Pro Thr Leu Ser Val
        115                 120                 125

His Pro Gly Pro Glu Val Ile Ser Gly Glu Lys Val Thr Phe Tyr Cys
    130                 135                 140

Arg Leu Asp Thr Ala Thr Ser Met Phe Leu Leu Leu Lys Glu Gly Arg
145                 150                 155                 160
```

```
Ser Ser His Val Gln Arg Gly Tyr Gly Lys Val Gln Ala Glu Phe Pro
            165                 170                 175

Leu Gly Pro Val Thr Thr Ala His Arg Gly Thr Tyr Arg Cys Phe Gly
        180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
                245                 250                 255

Leu Arg Met Gly Leu Ala Phe Leu Val Leu Ala Leu Val Trp Phe
                260                 265                 270

Leu Val Glu Asp Trp Leu Ser Arg Lys Arg Thr Arg Glu Arg Ala Ser
            275                 280                 285

Arg Ala Ser Thr Trp Glu Gly Arg Arg Arg Leu Asn Thr Gln Thr Leu
        290                 295                 300
```

<210> SEQ ID NO 2
<211> LENGTH: 306
<212> TYPE: PRT
<213> ORGANISM: Macaca fascicularis

<400> SEQUENCE: 2

```
Met Ser Ser Thr Leu Arg Ala Leu Leu Cys Leu Gly Leu Cys Leu Ser
1               5                   10                  15

Gln Arg Ile Ser Ala Pro Lys Gln Thr Leu Pro Lys Pro Ile Ile Arg
                20                  25                  30

Ala Glu Ser Thr Tyr Met Val Pro Lys Glu Lys Gln Ala Thr Leu Cys
            35                  40                  45

Cys Gln Gly Ser Tyr Gly Ala Val Glu Tyr Gln Leu His Phe Glu Gly
    50                  55                  60

Ser Leu Phe Ala Val Glu Arg Pro Lys Pro Pro Glu Arg Ile Asn Gly
65                  70                  75                  80

Val Lys Phe His Ile Pro Asp Met Asn Ser Arg Lys Ala Gly Arg Tyr
                85                  90                  95

Ser Cys Ile Tyr Arg Val Gly Glu Leu Trp Ser Glu Arg Ser Asp Leu
                100                 105                 110

Leu Asp Leu Val Val Thr Glu Met Tyr Asp Thr Pro Thr Leu Ser Val
            115                 120                 125

His Pro Gly Pro Glu Val Thr Ser Gly Glu Lys Val Thr Phe Tyr Cys
    130                 135                 140

Arg Leu Asp Thr Ala Thr Ser Met Phe Leu Leu Leu Lys Glu Gly Arg
145                 150                 155                 160

Ser Arg Asp Val Gln Arg Ser Tyr Gly Lys Val Gln Ala Glu Phe Pro
                165                 170                 175

Met Gly Pro Val Thr Thr Ala His Arg Gly Ser Tyr Arg Cys Phe Gly
            180                 185                 190

Ser Tyr Asn Asn Tyr Ala Trp Ser Phe Pro Ser Glu Pro Val Lys Leu
        195                 200                 205

Leu Val Thr Gly Asp Ile Glu Asn Thr Ser Leu Ala Pro Thr Asp Pro
    210                 215                 220
```

```
Thr Phe Pro Asp Ser Trp Asp Thr Cys Leu Leu Thr Arg Glu Thr Gly
225                 230                 235                 240

Leu Gln Lys Asp Leu Ala Leu Trp Asp His Thr Ala Gln Asn Leu Leu
            245                 250                 255

Arg Met Gly Leu Ala Phe Leu Val Leu Val Ala Leu Val Cys Leu Leu
        260                 265                 270

Val Glu Asp Trp Leu Ser Arg Lys Arg Thr Arg Glu Gln Ala Ser Arg
    275                 280                 285

Ala Ser Thr Trp Glu Gly Arg Arg Leu Asn Lys His Lys Asp Ser
290                 295                 300

Glu Glu
305

<210> SEQ ID NO 3
<211> LENGTH: 115
<212> TYPE: PRT
<213> ORGANISM: Mus musculus

<400> SEQUENCE: 3

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Thr Ile Tyr Pro Gly Ser Asp Ile Thr Asn Tyr Asp Glu Lys Phe
    50                  55                  60

Lys Asn Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asp Gly Arg Phe Ala Asn Trp Gly Gln Gly Thr Leu Val Thr
            100                 105                 110

Val Ser Ala
        115

<210> SEQ ID NO 4
<211> LENGTH: 105
<212> TYPE: PRT
<213> ORGANISM: Mus musculus

<400> SEQUENCE: 4

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Leu Pro Leu Thr Phe
                85                  90                  95

Gly Ala Gly Thr Lys Leu Glu Leu Lys
            100                 105
```

```
<210> SEQ ID NO 5
<211> LENGTH: 5
<212> TYPE: PRT
<213> ORGANISM: Mus musculus

<400> SEQUENCE: 5

Ser Tyr Trp Met His
1               5

<210> SEQ ID NO 6
<211> LENGTH: 7
<212> TYPE: PRT
<213> ORGANISM: Mus musculus

<400> SEQUENCE: 6

Gly Tyr Thr Phe Thr Ser Tyr
1               5

<210> SEQ ID NO 7
<211> LENGTH: 8
<212> TYPE: PRT
<213> ORGANISM: Mus musculus

<400> SEQUENCE: 7

Gly Tyr Thr Phe Thr Ser Tyr Trp
1               5

<210> SEQ ID NO 8
<211> LENGTH: 17
<212> TYPE: PRT
<213> ORGANISM: Mus musculus

<400> SEQUENCE: 8

Thr Ile Tyr Pro Gly Ser Asp Ile Thr Asn Tyr Asp Glu Lys Phe Lys
1               5                   10                  15

Asn

<210> SEQ ID NO 9
<211> LENGTH: 4
<212> TYPE: PRT
<213> ORGANISM: Mus musculus

<400> SEQUENCE: 9

Pro Gly Ser Asp
1

<210> SEQ ID NO 10
<211> LENGTH: 8
<212> TYPE: PRT
<213> ORGANISM: Mus musculus

<400> SEQUENCE: 10

Ile Tyr Pro Gly Ser Asp Ile Thr
1               5

<210> SEQ ID NO 11
<211> LENGTH: 6
<212> TYPE: PRT
<213> ORGANISM: Mus musculus

<400> SEQUENCE: 11

Asp Gly Arg Phe Ala Asn
1               5
```

<210> SEQ ID NO 12
<211> LENGTH: 4
<212> TYPE: PRT
<213> ORGANISM: Mus musculus

<400> SEQUENCE: 12

Gly Arg Phe Ala
1

<210> SEQ ID NO 13
<211> LENGTH: 8
<212> TYPE: PRT
<213> ORGANISM: Mus musculus

<400> SEQUENCE: 13

Thr Arg Asp Gly Arg Phe Ala Asn
1               5

<210> SEQ ID NO 14
<211> LENGTH: 10
<212> TYPE: PRT
<213> ORGANISM: Mus musculus

<400> SEQUENCE: 14

Ser Ala Ser Ser Ser Val Ser Tyr Met His
1               5                   10

<210> SEQ ID NO 15
<211> LENGTH: 6
<212> TYPE: PRT
<213> ORGANISM: Mus musculus

<400> SEQUENCE: 15

Ser Ser Ser Val Ser Tyr
1               5

<210> SEQ ID NO 16
<211> LENGTH: 5
<212> TYPE: PRT
<213> ORGANISM: Mus musculus

<400> SEQUENCE: 16

Ser Ser Val Ser Tyr
1               5

<210> SEQ ID NO 17
<211> LENGTH: 7
<212> TYPE: PRT
<213> ORGANISM: Mus musculus

<400> SEQUENCE: 17

Glu Ile Ser Lys Leu Ala Ser
1               5

<210> SEQ ID NO 18
<211> LENGTH: 5
<212> TYPE: PRT
<213> ORGANISM: Mus musculus
<220> FEATURE:
<221> NAME/KEY: X
<222> LOCATION: (4)..(5)
<223> OTHER INFORMATION: X cand be any amino acid

```
<400> SEQUENCE: 18

Glu Ile Ser Xaa Xaa
1               5

<210> SEQ ID NO 19
<211> LENGTH: 8
<212> TYPE: PRT
<213> ORGANISM: Mus musculus

<400> SEQUENCE: 19

Gln Gln Trp Asn Leu Pro Leu Thr
1               5

<210> SEQ ID NO 20
<211> LENGTH: 5
<212> TYPE: PRT
<213> ORGANISM: Mus musculus

<400> SEQUENCE: 20

Trp Asn Leu Pro Leu
1               5

<210> SEQ ID NO 21
<211> LENGTH: 107
<212> TYPE: PRT
<213> ORGANISM: Mus musculus

<400> SEQUENCE: 21

Glu Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Tyr
                85                  90                  95

Thr Phe Gly Gly Gly Thr Lys Leu Glu Ile Lys
            100                 105

<210> SEQ ID NO 22
<211> LENGTH: 11
<212> TYPE: PRT
<213> ORGANISM: Mus musculus

<400> SEQUENCE: 22

Arg Ala Ser Gln Asp Ile Gly Ser Ser Leu Asn
1               5                   10

<210> SEQ ID NO 23
<211> LENGTH: 7
<212> TYPE: PRT
<213> ORGANISM: Mus musculus

<400> SEQUENCE: 23

Ser Gln Asp Ile Gly Ser Ser
1               5
```

-continued

```
<210> SEQ ID NO 24
<211> LENGTH: 6
<212> TYPE: PRT
<213> ORGANISM: Mus musculus

<400> SEQUENCE: 24

Gln Asp Ile Gly Ser Ser
1               5

<210> SEQ ID NO 25
<211> LENGTH: 7
<212> TYPE: PRT
<213> ORGANISM: Mus musculus

<400> SEQUENCE: 25

Ala Thr Ser Ser Leu Asp Ser
1               5

<210> SEQ ID NO 26
<211> LENGTH: 5
<212> TYPE: PRT
<213> ORGANISM: Mus musculus
<220> FEATURE:
<221> NAME/KEY: X
<222> LOCATION: (4)..(5)
<223> OTHER INFORMATION: X may be any amino acid

<400> SEQUENCE: 26

Ala Thr Ser Xaa Xaa
1               5

<210> SEQ ID NO 27
<211> LENGTH: 9
<212> TYPE: PRT
<213> ORGANISM: Mus musculus

<400> SEQUENCE: 27

Leu Gln Tyr Ala Ser Ser Pro Tyr Thr
1               5

<210> SEQ ID NO 28
<211> LENGTH: 6
<212> TYPE: PRT
<213> ORGANISM: Mus musculus

<400> SEQUENCE: 28

Tyr Ala Ser Ser Pro Tyr
1               5

<210> SEQ ID NO 29
<211> LENGTH: 117
<212> TYPE: PRT
<213> ORGANISM: Mus musculus

<400> SEQUENCE: 29

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Leu Arg Pro Gly Gln Gly Phe Glu Trp Ile
        35                  40                  45

Gly Glu Ile Ile Pro Ser Asn Gly Val Thr Asn Tyr Asn Glu Lys Phe
    50                  55                  60
```

```
Lys Arg Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Ile Arg Leu Arg Tyr Ala Leu Asp Tyr Trp Gly Gln Gly Thr Ser
            100                 105                 110

Val Thr Val Ser Ala
            115

<210> SEQ ID NO 30
<211> LENGTH: 107
<212> TYPE: PRT
<213> ORGANISM: Mus musculus

<400> SEQUENCE: 30

Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Ser Asn Phe
             20                  25                  30

Leu Asn Trp Tyr Gln Gln Lys Pro Asp Gly Thr Val Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Pro
                 85                  90                  95

Thr Phe Gly Gly Gly Thr Lys Leu Glu Ile Lys
            100                 105

<210> SEQ ID NO 31
<211> LENGTH: 5
<212> TYPE: PRT
<213> ORGANISM: Mus musculus

<400> SEQUENCE: 31

Ser Tyr Trp Met His
  1               5

<210> SEQ ID NO 32
<211> LENGTH: 7
<212> TYPE: PRT
<213> ORGANISM: Mus musculus

<400> SEQUENCE: 32

Gly Tyr Thr Phe Thr Ser Tyr
  1               5

<210> SEQ ID NO 33
<211> LENGTH: 8
<212> TYPE: PRT
<213> ORGANISM: Mus musculus

<400> SEQUENCE: 33

Gly Tyr Thr Phe Thr Ser Tyr Trp
  1               5

<210> SEQ ID NO 34
<211> LENGTH: 17
<212> TYPE: PRT
<213> ORGANISM: Mus musculus
```

```
<400> SEQUENCE: 34

Glu Ile Ile Pro Ser Asn Gly Val Thr Asn Tyr Asn Glu Lys Phe Lys
1               5                   10                  15
Arg

<210> SEQ ID NO 35
<211> LENGTH: 4
<212> TYPE: PRT
<213> ORGANISM: Mus musculus

<400> SEQUENCE: 35

Pro Ser Asn Gly
1

<210> SEQ ID NO 36
<211> LENGTH: 8
<212> TYPE: PRT
<213> ORGANISM: Mus musculus

<400> SEQUENCE: 36

Ile Ile Pro Ser Asn Gly Val Thr
1               5

<210> SEQ ID NO 37
<211> LENGTH: 8
<212> TYPE: PRT
<213> ORGANISM: Mus musculus

<400> SEQUENCE: 37

Arg Leu Arg Tyr Ala Leu Asp Tyr
1               5

<210> SEQ ID NO 38
<211> LENGTH: 6
<212> TYPE: PRT
<213> ORGANISM: Mus musculus

<400> SEQUENCE: 38

Leu Arg Tyr Ala Leu Asp
1               5

<210> SEQ ID NO 39
<211> LENGTH: 10
<212> TYPE: PRT
<213> ORGANISM: Mus musculus

<400> SEQUENCE: 39

Thr Ile Arg Leu Arg Tyr Ala Leu Asp Tyr
1               5                   10

<210> SEQ ID NO 40
<211> LENGTH: 11
<212> TYPE: PRT
<213> ORGANISM: Mus musculus

<400> SEQUENCE: 40

Arg Ala Ser Gln Asp Ile Ser Asn Phe Leu Asn
1               5                   10

<210> SEQ ID NO 41
<211> LENGTH: 7
<212> TYPE: PRT
<213> ORGANISM: Mus musculus
```

```
<400> SEQUENCE: 41

Ser Gln Asp Ile Ser Asn Phe
1               5

<210> SEQ ID NO 42
<211> LENGTH: 6
<212> TYPE: PRT
<213> ORGANISM: Mus musculus

<400> SEQUENCE: 42

Gln Asp Ile Ser Asn Phe
1               5

<210> SEQ ID NO 43
<211> LENGTH: 7
<212> TYPE: PRT
<213> ORGANISM: Mus musculus

<400> SEQUENCE: 43

Tyr Thr Ser Arg Leu His Ser
1               5

<210> SEQ ID NO 44
<211> LENGTH: 5
<212> TYPE: PRT
<213> ORGANISM: Mus musculus
<220> FEATURE:
<221> NAME/KEY: X
<222> LOCATION: (4)..(5)
<223> OTHER INFORMATION: X may be any amino acid

<400> SEQUENCE: 44

Tyr Thr Ser Xaa Xaa
1               5

<210> SEQ ID NO 45
<211> LENGTH: 9
<212> TYPE: PRT
<213> ORGANISM: Mus musculus

<400> SEQUENCE: 45

Gln Gln Gly Asn Thr Leu Pro Pro Thr
1               5

<210> SEQ ID NO 46
<211> LENGTH: 6
<212> TYPE: PRT
<213> ORGANISM: Mus musculus

<400> SEQUENCE: 46

Gly Asn Thr Leu Pro Pro
1               5

<210> SEQ ID NO 47
<211> LENGTH: 107
<212> TYPE: PRT
<213> ORGANISM: Mus musculus

<400> SEQUENCE: 47

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30
```

-continued

Val Ala Trp Tyr Gln Gln Lys Pro Gly Gln Ser Pro Lys Ala Leu Ile
                35                  40                  45

Tyr Ser Thr Ser Phe Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Phe
                85                  90                  95

Thr Phe Gly Ser Gly Thr Lys Leu Glu Ile Lys
            100                 105

<210> SEQ ID NO 48
<211> LENGTH: 11
<212> TYPE: PRT
<213> ORGANISM: Mus musculus

<400> SEQUENCE: 48

Lys Ala Ser Gln Asn Val Gly Thr Asn Val Ala
1               5                   10

<210> SEQ ID NO 49
<211> LENGTH: 7
<212> TYPE: PRT
<213> ORGANISM: Mus musculus

<400> SEQUENCE: 49

Ser Gln Asn Val Gly Thr Asn
1               5

<210> SEQ ID NO 50
<211> LENGTH: 6
<212> TYPE: PRT
<213> ORGANISM: Mus musculus

<400> SEQUENCE: 50

Gln Asn Val Gly Thr Asn
1               5

<210> SEQ ID NO 51
<211> LENGTH: 7
<212> TYPE: PRT
<213> ORGANISM: Mus musculus

<400> SEQUENCE: 51

Ser Thr Ser Phe Arg Tyr Ser
1               5

<210> SEQ ID NO 52
<211> LENGTH: 5
<212> TYPE: PRT
<213> ORGANISM: Mus musculus
<220> FEATURE:
<221> NAME/KEY: X
<222> LOCATION: (4)..(5)
<223> OTHER INFORMATION: X may be any amino acid

<400> SEQUENCE: 52

Ser Thr Ser Xaa Xaa
1               5

<210> SEQ ID NO 53
<211> LENGTH: 9
<212> TYPE: PRT
<213> ORGANISM: Mus musculus

<400> SEQUENCE: 53

Gln Gln Tyr Asn Ser Tyr Pro Phe Thr
1               5

<210> SEQ ID NO 54
<211> LENGTH: 6
<212> TYPE: PRT
<213> ORGANISM: Mus musculus

<400> SEQUENCE: 54

Tyr Asn Ser Tyr Pro Phe
1               5

<210> SEQ ID NO 55
<211> LENGTH: 115
<212> TYPE: PRT
<213> ORGANISM: Mus musculus

<400> SEQUENCE: 55

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Met His Trp Ala Lys Gln Arg Pro Gly Gln Gly Leu Glu Trp Ile
        35                  40                  45

Gly His Ile His Pro Asn Ser Gly Ile Ser Asn Tyr Asn Glu Lys Phe
    50                  55                  60

Lys Gly Lys Ala Thr Leu Thr Val Asp Thr Ser Ser Thr Ala Tyr
65                  70                  75                  80

Val Asp Leu Ser Ser Leu Thr Ser Glu Asp Ser Ala Val Tyr Tyr Cys
                85                  90                  95

Ser Arg Gly Gly Arg Phe Asp Asp Trp Gly Ala Gly Thr Thr Val Thr
            100                 105                 110

Val Ser Ser
        115

<210> SEQ ID NO 56
<211> LENGTH: 107
<212> TYPE: PRT
<213> ORGANISM: Mus musculus

<400> SEQUENCE: 56

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Arg Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Trp
                85                  90                  95

Thr Phe Gly Gly Gly Thr Lys Leu Glu Ile Lys
            100                 105

```
<210> SEQ ID NO 57
<211> LENGTH: 5
<212> TYPE: PRT
<213> ORGANISM: Mus musculus

<400> SEQUENCE: 57

Ser Ser Trp Met His
1               5

<210> SEQ ID NO 58
<211> LENGTH: 7
<212> TYPE: PRT
<213> ORGANISM: Mus musculus

<400> SEQUENCE: 58

Gly Tyr Thr Phe Thr Ser Ser
1               5

<210> SEQ ID NO 59
<211> LENGTH: 8
<212> TYPE: PRT
<213> ORGANISM: Mus musculus

<400> SEQUENCE: 59

Gly Tyr Thr Phe Thr Ser Ser Trp
1               5

<210> SEQ ID NO 60
<211> LENGTH: 17
<212> TYPE: PRT
<213> ORGANISM: Mus musculus

<400> SEQUENCE: 60

His Ile His Pro Asn Ser Gly Ile Ser Asn Tyr Asn Glu Lys Phe Lys
1               5                   10                  15

Gly

<210> SEQ ID NO 61
<211> LENGTH: 4
<212> TYPE: PRT
<213> ORGANISM: Mus musculus

<400> SEQUENCE: 61

Pro Asn Ser Gly
1

<210> SEQ ID NO 62
<211> LENGTH: 8
<212> TYPE: PRT
<213> ORGANISM: Mus musculus

<400> SEQUENCE: 62

Ile His Pro Asn Ser Gly Ile Ser
1               5

<210> SEQ ID NO 63
<211> LENGTH: 6
<212> TYPE: PRT
<213> ORGANISM: Mus musculus

<400> SEQUENCE: 63

Gly Gly Arg Phe Asp Asp
1               5
```

```
<210> SEQ ID NO 64
<211> LENGTH: 4
<212> TYPE: PRT
<213> ORGANISM: Mus musculus

<400> SEQUENCE: 64

Gly Arg Phe Asp
1

<210> SEQ ID NO 65
<211> LENGTH: 8
<212> TYPE: PRT
<213> ORGANISM: Mus musculus

<400> SEQUENCE: 65

Ser Arg Gly Gly Arg Phe Asp Asp
1               5

<210> SEQ ID NO 66
<211> LENGTH: 7
<212> TYPE: PRT
<213> ORGANISM: Mus musculus

<400> SEQUENCE: 66

Ala Thr Ser Arg Leu Asp Ser
1               5

<210> SEQ ID NO 67
<211> LENGTH: 9
<212> TYPE: PRT
<213> ORGANISM: Mus musculus

<400> SEQUENCE: 67

Leu Gln Tyr Ala Ser Ser Pro Trp Thr
1               5

<210> SEQ ID NO 68
<211> LENGTH: 6
<212> TYPE: PRT
<213> ORGANISM: mus musculus

<400> SEQUENCE: 68

Tyr Ala Ser Ser Pro Trp
1               5

<210> SEQ ID NO 69
<211> LENGTH: 218
<212> TYPE: PRT
<213> ORGANISM: homo sapiens

<400> SEQUENCE: 69

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95
```

```
Lys Ala Leu Pro Ala Pro Ile Glu Lys Thr Ile Ser Lys Ala Lys Gly
                100                 105                 110

Gln Pro Arg Glu Pro Gln Val Tyr Thr Leu Pro Pro Ser Arg Asp Glu
            115                 120                 125

Leu Thr Lys Asn Gln Val Ser Leu Thr Cys Leu Val Lys Gly Phe Tyr
        130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 70
<211> LENGTH: 234
<212> TYPE: PRT
<213> ORGANISM: homo sapiens

<400> SEQUENCE: 70

Gln Gln Gln Thr Leu Pro Lys Pro Phe Ile Trp Ala Glu Pro His Phe
1               5                   10                  15

Met Val Pro Lys Glu Lys Gln Val Thr Ile Cys Cys Gln Gly Asn Tyr
            20                  25                  30

Gly Ala Val Glu Tyr Gln Leu His Phe Glu Gly Ser Leu Phe Ala Val
        35                  40                  45

Asp Arg Pro Lys Pro Pro Glu Arg Ile Asn Lys Val Lys Phe Tyr Ile
    50                  55                  60

Pro Asp Met Asn Ser Arg Met Ala Gly Gln Tyr Ser Cys Ile Tyr Arg
65                  70                  75                  80

Val Gly Glu Leu Trp Ser Glu Pro Ser Asn Leu Leu Asp Leu Val Val
                85                  90                  95

Thr Glu Met Tyr Asp Thr Pro Thr Leu Ser Val His Pro Gly Pro Glu
            100                 105                 110

Val Ile Ser Gly Glu Lys Val Thr Phe Tyr Cys Arg Leu Asp Thr Ala
        115                 120                 125

Thr Ser Met Phe Leu Leu Leu Lys Glu Gly Arg Ser Ser His Val Gln
    130                 135                 140

Arg Gly Tyr Gly Lys Val Gln Ala Glu Phe Pro Leu Gly Pro Val Thr
145                 150                 155                 160

Thr Ala His Arg Gly Thr Tyr Arg Cys Phe Gly Ser Tyr Asn Asn His
                165                 170                 175

Ala Trp Ser Phe Pro Ser Glu Pro Val Lys Leu Leu Val Thr Gly Asp
            180                 185                 190

Ile Glu Asn Thr Ser Leu Ala Pro Glu Asp Pro Thr Phe Pro Ala Asp
        195                 200                 205

Thr Trp Gly Thr Tyr Leu Leu Thr Thr Glu Thr Gly Leu Gln Lys Asp
    210                 215                 220

His Ala Leu Trp Asp His Thr Ala Gln Asn
225                 230
```

-continued

```
<210> SEQ ID NO 71
<211> LENGTH: 18
<212> TYPE: PRT
<213> ORGANISM: Homo sapiens

<400> SEQUENCE: 71

Asp Thr Pro Thr Leu Ser Val His Pro Gly Pro Glu Val Ile Ser Gly
1               5                   10                  15

Glu Lys

<210> SEQ ID NO 72
<211> LENGTH: 20
<212> TYPE: PRT
<213> ORGANISM: Homo sapiens

<400> SEQUENCE: 72

Val Gln Ala Glu Phe Pro Leu Gly Pro Val Thr Thr Ala His Arg Gly
1               5                   10                  15

Thr Tyr Arg Cys
            20

<210> SEQ ID NO 73
<211> LENGTH: 5
<212> TYPE: PRT
<213> ORGANISM: Homo sapiens

<400> SEQUENCE: 73

Asp Thr Pro Thr Leu
1               5

<210> SEQ ID NO 74
<211> LENGTH: 10
<212> TYPE: PRT
<213> ORGANISM: Homo sapiens

<400> SEQUENCE: 74

Trp Ser Phe Pro Ser Glu Pro Val Lys Leu
1               5                   10

<210> SEQ ID NO 75
<211> LENGTH: 11
<212> TYPE: PRT
<213> ORGANISM: Homo sapiens

<400> SEQUENCE: 75

Ala Trp Ser Phe Pro Ser Glu Pro Val Lys Leu
1               5                   10

<210> SEQ ID NO 76
<211> LENGTH: 17
<212> TYPE: PRT
<213> ORGANISM: Homo sapiens

<400> SEQUENCE: 76

Leu Lys Glu Gly Arg Ser Ser His Val Gln Arg Gly Tyr Gly Lys Val
1               5                   10                  15

Gln

<210> SEQ ID NO 77
<211> LENGTH: 19
<212> TYPE: PRT
<213> ORGANISM: Homo sapiens
```

-continued

```
<400> SEQUENCE: 77

Leu Leu Leu Lys Glu Gly Arg Ser Ser His Val Gln Arg Gly Tyr Gly
1               5                   10                  15

Lys Val Gln

<210> SEQ ID NO 78
<211> LENGTH: 6
<212> TYPE: PRT
<213> ORGANISM: Homo sapiens

<400> SEQUENCE: 78

Tyr Asp Thr Pro Thr Leu
1               5
```

NKP46 BINDING AGENTS

CROSS-REFERENCE TO RELATED APPLICATIONS

This application is a divisional of U.S. Ser. No. 16/478,863, filed Jul. 18, 2019, now U.S. Pat. No. 11,377,492, which is the U.S. national stage application of International Patent Application No. PCT/EP2018/051394, filed Jan. 22, 2018, which claims the benefit of U.S. Provisional Application No. 62/449,617 filed 24 Jan. 2017, and U.S. Provisional Application No. 62/530,443 filed 10 Jul. 2017, the disclosures of which are incorporated herein by reference in their entireties; including any drawings and sequence listings.

REFERENCE TO THE SEQUENCE LISTING

The present application is being filed along with a Sequence Listing in electronic format. The Sequence Listing is provided as a file entitled "Seq-List.txt", created Jul. 1, 2019, which is 27 KB in size. The information in the electronic format of the Sequence Listing is incorporated herein by reference in its entirety.

FIELD OF THE INVENTION

The present invention provides antigen-binding proteins capable of binding to NKp46 polypeptides. The antigen-binding proteins have increased activity in the treatment of disorders characterized by NKp46-expressing cells, particularly tumor cells.

BACKGROUND

NK cell activity is regulated by a complex mechanism that involves both activating and inhibitory signals. Several distinct NK-specific receptors have been identified that play an important role in the NK cell mediated recognition and killing of HLA Class I deficient target cells. Natural Cytotoxicity Receptors (NCR) refers to a class of activating receptor proteins, and the genes expressing them, that are specifically expressed in NK cells. Examples of NCRs include NKp30, NKp44, and NKp46 (see, e.g., Lanier (2001) Nat Immunol 2:23-27, Pende et al. (1999) J Exp Med. 190:1505-1516, Cantoni et al. (1999) J Exp Med. 189:787-796, Sivori et al (1997) J. Exp. Med. 186:1129-1136, Pessino et al. (1998) J Exp Med. 188(5):953-60; Mandelboim et al. (2001) Nature 409:1055-1060, the entire disclosures of which are herein incorporated by reference). These receptors are members of the Ig superfamily, and their cross-linking, induced by specific mAbs, leads to a strong NK cell activation resulting in increased intracellular Ca++ levels, triggering of cytotoxicity, and lymphokine release, and an activation of NK cytotoxicity against many types of target cells. The expression of NCRs, and NKp46 in particular, is reported as generally limited to NK cells.

PCTL's account for 15% to 20% of aggressive lymphomas and for 7% to 10% of all the non-Hodgkin lymphomas (NHLs) in Western countries. They usually occur in middle-aged to elderly patients, and presenting features are characterized by a disseminated disease in 68% of the patients, with systemic symptoms in nearly half of them (45%), bone marrow (BM) involvement in a quarter (25.8%), and extranodal disease in a third (37%). Despite aggressive therapy, more than half the patients die of their disease. While certain distinctive disease entities have improved prognostics if treated, the prognosis for many aggressive PTCLs remains relatively unchanged by the use of second- and third-generation chemotherapy regimens and 5-year overall survival (OS) still remains between 25% and 47% for PTCL-NOS, for example. Consequently, there is a need in the art for improved benefit to patients having PTC L.

SUMMARY OF THE INVENTION

Although NKp46 is an NK-cell selective cell surface protein in healthy individuals, NKp46 can be expressed by T cells in certain malignancies. Immunohistochemistry shows that NKp46 can be expressed in peripheral T-cell lymphomas (PTCLs) at expression levels permitting targeting with anti-NKp46 antibodies.

The invention results, inter alia, from the discovery of an epitope on human NKp46 that permits highly-effective targeting for elimination by antibodies, particularly immunoconjugates. By the study of a range of candidate anti-NKp46 antibodies, the inventors identified antibodies that had particularly high ability to mediate the depletion of NKp46+ tumor cells (antibodies 8B6A, 8B6B, 9H11A, 9H11B and 17E1). The assays presented herein were conducted using a drug conjugation methodology that permits precise numbers of cytotoxic agents to be conjugated to an antibody, such that substantially all antibodies in a mixture bear the same number of cytotoxic moieties (e.g., a drug:antibody ratio (DAR) of 2 or 4). The methodology permits antibodies and their epitopes to be compared without bias from differing distributions of DARs within the different antibody samples.

Interestingly, the antibodies that showed the highest activity all competed for binding to a single area/epitope on cell surface NKp46 polypeptide. The antibodies did not compete with known anti-NKp46 antibodies suggesting a region on NKp46 which is particularly suitable for targeting by immunoconjugates.

Furthermore, while many antibodies selected for binding to human NKp46 are unable to direct NK cells to lyse a RAJI tumor cell line made to express human NKp46, the antibodies 8B6A, 8B6B, 9H11A, 9H11B and 17E1 showed promising ability to induce ADCC toward tumor cells. The efficacy of the antibodies as inducers of ADCC is particularly remarkable in view of their high potency as immunoconjugates (highly active immunoconjugates often are poor ADCC-inducers in view of their ability to undergo intracellular internalization).

In view of the particularly high activity as immunoconjugates (as tested without the ability to mediate ADCC0, the antibodies can be advantageously used as immunoconjugates that lack Fcγ-mediated effector activity (e.g., do not mediate ADCC).

However, it will be appreciated that the antibodies can also be used as immunoconjugates that further possess Fcγ-mediated effector activity (e.g., mediate ADCC) thereby combining two modes of action. Alternatively, the antibodies can be used as "naked", ADCC-mediating, antibodies that are not conjugated to a toxic moiety.

In one aspect, as illustrated herein in the antibodies in the Examples using the anti-NKp46 antibodies immunoconjugates with stoichiometrically functionalized acceptor glutamines wherein substantially all antibodies in a mixture have a particular DAR (e.g., a DAR of 2 or 4), the antibodies are capable of potently inducing tumor cell death as immunoconjugates despite of lack of Fc-mediated effector function. The antibodies of the disclosure can comprise an Fc domain (or portion thereof) of human IgG1, IgG2, IgG3 or IgG4 isotype modified to reduce or abolish binding to one or more human Fcγ receptors (e.g., CD16A, CD16B, CD32A, CD32b, CD64). Such an antibody will minimize take-up by non-tumoral Fcγ receptor-expressing cells. Consequently, when conjugated to a cytotoxic agent having high potency/toxicity (e.g., DNA minor groove binding agents such as pyrrolobenzodiazepine agents, as shown in the Examples), the antibody is capable of being used at higher doses that would be possible otherwise, and may thus lead to greater efficacy in cancer treatment than an ADCC-mediating immunoconjugate. Optionally, as illustrated in the Examples herein, the antibody retains binding to human FcRn proteins thereby providing a vivo half-life.

Advantageously, the epitope bound by the antibodies is present on both human and non-primate NKp46 polypeptide, as expressed on the cell surface, as well as on NKp46 as expressed by cancer cells.

Provided in one aspect is an antibody or antibody fragment that competes for binding to NKp46 with any of 8B6A, 8B6B, 9H11A, 9H11B and 17E1, and/or binds to the same epitope on NKp46 as any of 8B6A, 8B6B, 9H11A, 9H11B and 17E1.

Provided in one aspect are several monoclonal antibodies that bind a human NKp46 polypeptide of SEQ ID NO: 1 expressed on the surface of a cell, and to a non-human primate NKp46 polypeptide of SEQ ID NO: 2 expressed on the surface of a cell, optionally wherein the antibody comprises a human Fc domain and is a depleting antibody.

In one aspect, provided is an antigen-binding compound that binds the same epitope and/or competes for binding to an NKp46 polypeptide with any one or any combination of monoclonal antibodies 8B6A, 8B6B, 9H11A, 9H11B and 17E1. In one embodiment, provided is antigen-binding compound binds the same epitope and/or competes for binding to an NKp46 polypeptide with an antibody selected from the group consisting of:
  (a) an antibody having respectively a VH and VL region of SEQ ID NOS: 3 and 4 (8B6A);
  (b) (a) an antibody having respectively a VH and VL region of SEQ ID NOS: 3 and 21 (8B6B);
  (c) an antibody having respectively a VH and VL region of SEQ ID NOS: 29 and 30 (9H11A);
  (d) an antibody having respectively a VH and VL region of SEQ ID NOS: 29 and 47 (9H11B); and
  (e) an antibody having respectively a VH and VL region of SEQ ID NOS: 55 and 56 (17E1).

The inventors have furthermore identified the epitopes on human NKp46 bound by the antibodies. The antibodies bind human NKp46 in the extracellular domain referred to as the "D2" domain. Thus, in one aspect, the invention provides an antigen binding domain, or a protein or polypeptide comprising such, e.g. an antibody or antibody fragment, that specifically binds to a segment of NKp46 corresponding to residues 100-187 of the NKp46 polypeptide of SEQ ID NO: 70. In another aspect the antibody binds a segment of NKp46 corresponding to residues 101-118 or 101-105 or 100-105 of the NKp46 polypeptide of SEQ ID NO: 70. In another aspect, the antibody binds to a segment of NKp46 corresponding to residues 150 to 169 of the NKp46 polypeptide of SEQ ID NO: 70. In another aspect, the antibody binds to a segment of NKp46 corresponding to residues 133-151 or 135-151 of the NKp46 polypeptide of SEQ ID NO: 70. In another aspect, the antibody binds to a segment of NKp46 corresponding to residues 178-187 or 177-187. In one embodiment, the antibody has decreased binding to an NKp46 polypeptide having an amino acid substitution in a segment of residues disclosed herein, compared to a wild-type NKp46 amino acid sequence. Such antibodies can further be characterized by having any properties described herein.

In one aspect, a protein (e.g. an antibody or antibody fragment) of the invention that binds a NKp46 polypeptide binds to at least one residue in the segment corresponding to residues 100-187 of the NKp46 polypeptide of SEQ ID NO: 70. In one embodiment the antibody binds to at least one residue in the segment corresponding to residues 101-118 (or 101-105 or 100-105), optionally further in combination with at least one residue in the segment 150-169 of the NKp46 polypeptide of SEQ ID NO: 70. Optionally, the antibody binds to at least one residue in the segment corresponding to residues 135 to 151 (or 133 to 151) of the NKp46 and/or to at least one residue in the segment corresponding to residues 178-187 (or 177-187) polypeptide of SEQ ID NO: 70.

In one aspect, provided is an antigen binding domain or antigen-binding protein (e.g., a hypervariable region or protein comprising such, an antibody or antibody fragment, an immunoconjugate, etc.) that binds a human NKp46 polypeptide, wherein the domain or protein comprises a heavy chain variable region and a light chain variable region combination selected from the group consisting of:
  (a) a heavy chain variable domain comprising the CDR 1, 2 and 3 of the heavy chain variable region of SEQ ID NO: 3 and (ii) a light chain variable region comprising the CDR 1, 2 and 3 of the light chain variable region of SEQ ID NO: 4;
  (b) a heavy chain variable domain comprising the CDR 1, 2 and 3 of the heavy chain variable region of SEQ ID NO: 3 and (ii) a light chain variable region comprising the CDR 1, 2 and 3 of the light chain variable region of SEQ ID NO: 21;
  (c) a heavy chain variable domain comprising the CDR 1, 2 and 3 of the heavy chain variable region of SEQ ID NO: 29 and (ii) a light chain variable region comprising the CDR 1, 2 and 3 of the light chain variable region of SEQ ID NO: 30;
  (d) a heavy chain variable domain comprising the CDR 1, 2 and 3 of the heavy chain variable region of SEQ ID NO: 29 and (ii) a light chain variable region comprising the CDR 1, 2 and 3 of the light chain variable region of SEQ ID NO: 47; and
  (e) a heavy chain variable domain comprising the CDR 1, 2 and 3 of the heavy chain variable region of SEQ ID NO: 55 and (ii) a light chain variable region comprising the CDR 1, 2 and 3 of the light chain variable region of SEQ ID NO: 56.

Optionally, an antigen-binding compound has an $EC_{50}$ of no more than 2 μg/ml, optionally no more than 1 μg/ml, no more than 0.5 μg/ml, no more than 0.1 μg/ml or no more than 0.05 μg/ml for binding to cells (e.g. CHO cells) made to express at their surface human NKp46 (e.g., a polypeptide having the amino acid sequence of SEQ ID NO: 1) or non-human primate NKp46 of SEQ ID NO: 2 (e.g., cynomolgus monkey).

In one embodiment, an anti-NKp46 antibody binds an epitope comprising one, two or three amino acid residues selected from the group consisting of the amino acid residues on NKp46 bound by 8B6A, 8B6B, 9H11A, 9H11B or 17E1.

In one embodiment, the antibodies do not compete for binding to NKp46 with antibodies Bab281, 9E2 or 195314 (reported to neutralize NKp46 function in NK cells). In one embodiment provided is an antibody that binds human NKp46 without substantially blocking the interaction of NKp46 with a natural ligand (e.g., wherein NKp46 and a natural ligand thereof are each expressed at the surface of cells).

Preferably the compound is an antibody, optionally a tetrameric antibody comprising two Ig heavy chains and two Ig light chains. Preferably the antibody has binding affinity ($K_D$), optionally wherein binding affinity is bivalent, optionally wherein binding affinity is monovalent, for a human NKp46 polypeptide at of less than $10^{-8}$ M, preferably less than $10^{-9}$ M, preferably less than $10^{-10}$ M, or preferably less than $10^{-11}$ M, as determined by, e.g., surface plasmon resonance (SPR) screening (such as by analysis with a BIAcore™ SPR analytical device). In one embodiment, the antibody is a depleting antibody, optionally wherein the antibody is an immunoconjugate comprising a cytotoxic moiety, optionally wherein the antibody induces ADCC and/or CDC toward an NKp46-expressing tumor cell.

In one aspect of any embodiment herein, the antibody is capable, upon binding to NKp46 on the surface of a tumor cell, to undergo intracellular internalization.

In one aspect of any embodiment herein, when an antibody is bound to NKp46 on an NKp46-expressing cell, a substantially reduced the amount of cell-surface NKp46 is observed in the NKp46-expressing cell.

In one embodiment, the antibody has a high affinity and slow off-rate, cross-reacts with cynomolgus and/or rhesus NKp46, and is of a depleting isotype such as, e.g., human IgG1.

In one aspect, provided is an anti-NKp46 immunoconjugate represented by Formula I:

(Formula I)

wherein,

Ab is an anti-NKp46 antibody or antibody fragment of the disclosure, e.g., an antibody comprising the heavy and light chain CDR1, 2 and 3 of any of antibodies 8B6A, 8B6B, 9H11A, 9H11B and 17E1, or an antibody or antibody fragment that binds the same epitope on NKp46;

X is a moiety which connects Ab and Z, e.g., the residue of a linker following covalent linkage to one or both of Ab and Z;

Z is an agent, optionally a cytotoxic agent, e.g., which is to be delivered to a NKp46-expressing cell; and m ranges from about 1 to about 15, optionally wherein m is 2 or 4.

In one embodiment, X comprises a linker (e.g., a peptidyl linker) that is cleaved by an intracellular peptidase or protease enzyme, optionally, a lysosomal or endosomal protease.

In one embodiment, the cytotoxic agent is selected from the group consisting of: taxanes, anthracyclines, camptothecins, epothilones, mytomycins, combretastatins, vinca alkaloids, nitrogen mustards, maytansinoids, calicheamycins, duocarmycins, tubulysins, dolastatins, auristatins, enediynes, pyrrolobenzodiazepines, ethylenimines, radioisotopes, and peptide toxins or fragments thereof.

In one embodiment of any aspect herein, an immunoconjugate comprises a cytotoxic agent covalently bound to an acceptor glutamine residues (Q) within or appended to a Fc region of the antibody (e.g., a Q within a TGase recognition tag fused to the C-terminus of a heavy and/or light chain). In one embodiment, the acceptor glutamine within a Fc region is at residue position 295 and/or 297 (Kabat EU numbering) of a heavy chain.

In one aspect, provided is an anti-NKp46 antibody or antibody fragment of any aspect of the disclosure, wherein the antibody (or antibody fragment) comprises a functionalized acceptor glutamine residue (Q) comprising the structure:

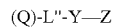

or a pharmaceutically acceptable salt or solvate thereof, wherein:

Q is a glutamine residue present within or appended to a constant region of the antibody or antibody fragment;

L" is a lysine-based linker in which the nitrogen atom is covalently bonded to the γ carbon of Q as a secondary amine;

Y is a spacer system; and

Z is a cytotoxic agent, optionally a DNA minor groove binding agent.

In one aspect, provided is a composition comprising a plurality of anti-NKp46 antibodies or antibody fragments of any aspect of the disclosure, wherein at least 90% of the antibodies or antibody fragments in said composition have (m) functionalized acceptor glutamine residues (Q) per antibody or fragment, wherein m is an integer selected from 2 or 4, wherein each of the functionalized acceptor glutamine residues has the structure:

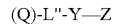

or a pharmaceutically acceptable salt or solvate thereof, wherein:

Q is a glutamine residue present within or appended to a constant region of the antibodies or antibody fragments;

L" is a lysine-based linker in which the nitrogen atom is covalently bonded to the γ carbon of Q as a secondary amine;

Y is a spacer system; and

Z is a cytotoxic agent, optionally a DNA minor groove binding agents.

In one aspect, provided is an anti-NKp46 antibody or antibody fragment of any aspect of the disclosure, wherein the antibody (or antibody fragment) comprises a functionalized acceptor glutamine residue (Q) comprising the structure:

or a pharmaceutically acceptable salt or solvate thereof, wherein:

Q is a glutamine residue present within or appended to a constant region of the antibodies or antibody fragments;

L" is a lysine-based linker in which the nitrogen atom is covalently bonded to the γ carbon of Q as a secondary amine;

(RR') is an addition product between a reactive moiety R and a complementary reactive moiety R';

Y is a spacer system; and

Z is a pyrrolobenzodiazepine (e.g., a pyrrolobenzodiazepine multimer, a pyrrolobenzodiazepine dimer, a pyrrolobenzodiazepine trimer).

In one aspect, provided is a composition comprising a plurality of anti-NKp46 antibodies or antibody fragments of any aspect of the disclosure (e.g., a plurality of antibodies comprising the heavy and light chain CDR1, 2 and 3 of any of antibodies 8B6A, 8B6B, 9H11A, 9H11B and 17E1), wherein at least 90% of the antibodies or antibody fragments in said composition have (m) functionalized acceptor glutamine residues (Q) per antibody or fragment, wherein m is an integer selected from 2 or 4, wherein each of the functionalized acceptor glutamine residues has the structure:

(Q)-L''-RR'—Y—Z or a pharmaceutically acceptable salt or solvate thereof, wherein:

Q is a glutamine residue present within or appended to a constant region of the antibodies or antibody fragments;

L'' is a lysine-based linker in which the nitrogen atom is covalently bonded to the γ carbon of Q as a secondary amine;

(RR') is an addition product between a reactive moiety R and a complementary reactive moiety R';

Y is a spacer system; and

Z is a pyrrolobenzodiazepine (e.g., a pyrrolobenzodiazepine multimer, a pyrrolobenzodiazepine dimer, a pyrrolobenzodiazepine trimer).

In one embodiment of the above structures, the antibodies or antibody fragments bind the same epitope and/or compete for binding to a NKp46 polypeptide with an antibody comprising the respective VH and VL of 8B6A, 8B6B, 9H11A, 9H11B or 17E1. In one embodiment of any of the above structures, the antibodies or antibody fragments comprise a heavy chain variable region and a light chain variable region combination selected from the group consisting of:

(a) a heavy chain variable domain comprising the CDR 1, 2 and 3 of the heavy chain variable region of SEQ ID NO: 3 and (ii) a light chain variable region comprising the CDR 1, 2 and 3 of the light chain variable region of SEQ ID NO: 4;

(b) a heavy chain variable domain comprising the CDR 1, 2 and 3 of the heavy chain variable region of SEQ ID NO: 3 and (ii) a light chain variable region comprising the CDR 1, 2 and 3 of the light chain variable region of SEQ ID NO: 21;

(c) a heavy chain variable domain comprising the CDR 1, 2 and 3 of the heavy chain variable region of SEQ ID NO: 29 and (ii) a light chain variable region comprising the CDR 1, 2 and 3 of the light chain variable region of SEQ ID NO: 30;

(d) a heavy chain variable domain comprising the CDR 1, 2 and 3 of the heavy chain variable region of SEQ ID NO: 29 and (ii) a light chain variable region comprising the CDR 1, 2 and 3 of the light chain variable region of SEQ ID NO: 47; and (e) a heavy chain variable domain comprising the CDR 1, 2 and 3 of the heavy chain variable region of SEQ ID NO: 55 and (ii) a light chain variable region comprising the CDR 1, 2 and 3 of the light chain variable region of SEQ ID NO: 56.

In one aspect, provided is an antibody that specifically binds NKp46, wherein the antibody has one or more (including any combination thereof, or all of) of the following properties:

(a) has a monovalent Kd of less than $10^{-8}$ M, or preferably less than $10^{-9}$ M for binding to a NKp46 polypeptide, as determined by, e.g., surface plasmon resonance (SPR) screening (such as by analysis with a BIAcore™ SPR analytical device);

(b) binds to an epitope on NKp46 as described herein (one or more amino acid residues on human NKp46 bound by antibodies 8B6A, 8B6B, 9H11A, 9H11B and/or 17E1 and/or competes for binding to a NKp46 polypeptide with antibody 8B6A, 8B6B, 9H11A, 9H11B and/or 17E1 and/or binds to at least one residue in the segment corresponding to residues 100-187 (or a residue in segment corresponding to residues 101-105 and/or a residue in segment corresponding to residues 150-169) of the NKp46 polypeptide of SEQ ID NO: 70);

(c) binds to non-human primate NKp46 (e.g., cynomolgus monkey polypeptide having an amino acid sequence of SEQ ID NO: 2), e.g., as expressed on the surface of a cell;

(d) binds to NKp46 as expressed on the surface of a tumor cell; and/or (e) is capable of undergoing intracellular internalization upon binding to an NKp46 polypeptide expressed at the surface of a cell (e.g., a malignant cell).

In any of the embodiments herein, any antibody herein may be characterized by any one or more features of (a)-(e), above.

In one embodiment, an antibody mediates or is capable of mediating complement dependent cytotoxicity (CDC) and/or antibody dependent cellular cytotoxicity (ADCC) toward a cell that expresses NKp46 on its surface.

In one embodiment, an antibody (e.g. an immunoconjugate) does not mediate or is not capable of mediating antibody dependent cellular cytotoxicity (ADCC) toward a cell that expresses NKp46 on its surface. For example, an antibody may lack N-linked glycosylation at amino acid residue N297 (Kabat EU numbering) in its heavy chains, and/or may comprise an amino acid modification in an Fc domain that reduces or abolishes binding to human CD16A and/or other human Fcγ receptors.

In one embodiment, provided is a method of producing and/or testing an anti-NKp46 antibody, said method comprising: (i) assessing whether the antibody binds to an epitope or region on NKp46 as described herein (one or more amino acid residues on NKp46 bound by antibodies 8B6A, 8B6B, 9H11A, 9H11B and/or 17E1 and/or competes for binding to a NKp46 polypeptide with antibody 8B6A, 8B6B, 9H11A, 9H11B and/or 17E1 and/or binds to at least one residue in the segment corresponding to residues 100-187 of the NKp46 polypeptide of SEQ ID NO:1); and/or (ii) assessing whether the antibody induces complement dependent cytotoxicity (CDC) and/or antibody dependent cellular cytotoxicity (ADCC) toward a cell that expresses NKp46 on its surface. Step (i) may optionally comprise bringing the antibody that binds a NKp46 polypeptide into contact with NKp46 polypeptide (e.g., an isolated polypeptide or a polypeptide expressed on the surface of a cell), optionally wherein the NKp46 polypeptide is a mutated polypeptide. Step (ii) may optionally comprise bringing the antibody that binds a NKp46 polypeptide into contact with a cell expressing a NKp46 polypeptide (e.g., a tumor cell) in the presence of immune effector cells (e.g., T cells, NK cells).

In another embodiment, provided is a method of producing, assessing, selecting or screening an antibody or immunoconjugate that binds a NKp46 polypeptide in a mammalian subject, optionally for the treatment of a cancer, said method comprising the steps of:

a) providing a plurality immunoconjugates comprising an antibody that binds human NKp46 conjugated to a cytotoxic moiety, wherein the immunoconjugates differ in their hypervariable region amino acid sequences but bear the same cytotoxic moiety and share the same number of cytotoxic moieties per antibody; and b) performing a selection step to select an antibody or immunoconjugate from the plurality, the step comprising:

(i) assessing whether the immunoconjugate is capable of (directly) depleting a cell that expresses NKp46 on its surface (e.g., as an immunoconjugate lacking effector function, in the absence of immune effector cells, in the absence of cells other than NKp46+ expressing cells, and/or in the absence of non-tumoral cells). In one embodiment, each immunoconjugate is a composition comprising a plurality of immunoconjugates sharing hypervariable regions, wherein at least 90% of the immunoconjugates in each composition have (m) cytotoxic moieties per antibody or fragment, wherein m is an integer selected from 2 or 4. In one embodiment, each cytotoxic moiety is bound to an acceptor glutamine within the primary amino acid sequence of an antibody.

Optionally, the method further comprises: (ii) assessing whether the antibody binds to a region or epitope on NKp46 as described herein (one or more amino acid residues on NKp46 bound by antibodies 8B6A, 8B6B, 9H11A, 9H11B and/or 17E1 and/or competes for binding to a NKp46 polypeptide with antibody 8B6A, 8B6B, 9H11A, 9H11B and/or 17E1 and/or binds to at least one residue in the segment corresponding to residues 100-187 of the NKp46 polypeptide of SEQ ID NO:1); and/or (iii) assessing whether the antibody induces antibody dependent cellular cytotoxicity (ADCC) toward a cell that expresses NKp46 on its surface.

In one embodiment, the method further comprises selecting an immunoconjugate that is capable of (directly) depleting a cell that expresses NKp46 on its surface. In one embodiment, the method further comprises selecting an immunoconjugate that binds to an epitope on NKp46 as described herein (one or more amino acid residues on NKp46 bound by antibodies 8B6A, 8B6B, 9H11A, 9H11B and/or 17E1 and/or competes for binding to a NKp46 polypeptide with antibody 8B6A, 8B6B, 9H11A, 9H11B and/or 17E1 and/or binds to at least one residue in the segment corresponding to residues 100-187 of the NKp46 polypeptide of SEQ ID NO:1). In one embodiment, the method further comprises selecting an immunoconjugate that induces antibody dependent cellular cytotoxicity (ADCC). In one embodiment, the method further comprises a step of further processing a selected immunoconjugate, of producing of a quantity of immunoconjugate a selected immunoconjugate, and/or of further testing a selected immunoconjugate for biological activity in vitro or in vivo.

In another embodiment, provided is a method of producing an antibody that binds a NKp46 polypeptide comprising culturing a recombinant host cell expressing an anti-NKp46 antibody described herein, and recovering anti-NKp46 antibody produced by said host cell, optionally further comprising formulating said antibody (e.g., with a pharmaceutical excipient) for administration to a human subject.

Optionally, the compound in any embodiment herein is an antibody, optionally a tetrameric antibody comprising two Ig heavy chains and two Ig light chains.

In one embodiment, the anti-NKp46 antibody is a "naked antibody" and is not coupled to a toxic agent, optionally the naked antibody comprises an Fc region modified to increase binding to an Fcγ receptor, e.g., CD16. In one embodiment, a naked or coupled antibody comprises a heavy chain comprising a human Fc region (e.g., IgG1) that binds Fcγ receptors (e.g., CD16). Optionally such antibody induces complement dependent cytotoxicity (CDC) and/or antibody dependent cellular cytotoxicity (ADCC) toward a cell that expresses NKp46 on its surface.

In one aspect of any of the embodiments herein, the antibody may have a heavy and/or light chain having one, two or three CDRs of the respective heavy and/or light chain of an antibody selected from the group consisting of antibody 8B6A, 8B6B, 9H11A, 9H11B and 17E1.

In one embodiment the antibody is chimeric, e.g., contains a non-murine, optionally a human, constant region. In one embodiment the antibody has a variable region comprising human framework amino acid sequences. In one embodiment, the antibody is human or humanized. In one aspect of any of the embodiments, the isotype of the antibody is a human IgG, optionally human IgG1, IgG2, IgG3 or IgG4. In one embodiment the antibody comprises a human Fc domain or is of an isotype that is bound by human FcγR (e.g., FcγRIIIA), e.g., an antibody of IgG1 or IgG3 isotype.

In one embodiment the antibody is an immunoconjugate that comprises an antibody bound to a cytotoxic agent, wherein the antibody comprises a human Fc domain of an isotype that naturally is bound by human FcγR (e.g., FcγRIIIA) but comprising one or more amino acid modifications to decrease binding to a human FcγR polypeptide (e.g., CD16A, CD16B, CD32A, CD32B, CD64). In one embodiment the antibody comprises a human Fc domain of an isotype that naturally is bound by human FcγR (e.g., FcγRIIIA) but which Fc domain lacks N297-linked glycosylation (Kabat EU numbering) and has no/low binding to a human FcγR polypeptide (e.g., CD16A, CD16B, CD32A, CD32B, CD64).

In one aspect of any of the embodiments, the antibody is or comprises an antibody fragment selected from a Fab, Fab', Fab'-SH, F(ab')2, Fv, diabody, single-chain antibody fragment, or a multispecific antibody (e.g., a bispecific antibody, a trispecific antibody) comprising multiple different antibody fragments. Optionally an antibody is tetrameric (two heavy and two light chains) and binds NKp46 in bivalent fashion (e.g., IgG antibodies).

In one embodiment, the antibodies are capable of directly inducing (e.g., in the absence of immune effector cells) at least 20%, 30%, 40% or 50% cell death, e.g., in an in vitro assay, of NKp46-expressing cells.

In one aspect, provided is a method of treatment using a depleting antibody that specifically binds NKp46. The antibodies can be used as prophylactic or therapeutic treatment; in any of the embodiments herein, a therapeutically effective amount of the antibody can be interchanged with a prophylactically effective amount of an antibody. In one aspect, provided is a method of treating a patient with a cancer or other proliferative disease characterized by proliferating NKp46-expressing cells, the method comprising administering to the patient a pharmaceutically effective amount of an antibody of the disclosure. In one embodiment, the cancer is a lymphoma. In one embodiment, the cancer or disease is selected from the group consisting of: a PTCL-NOS, AITL, or ALCL (ALK+ or ALK−), ATL, NK-/T cell lymphoma, an extranodal NK-/T-cell lymphoma, nasal type, EATL, Celiac disease, Refractory Celiac Disease type I (RCDI) and Refractory Celiac Disease type II (RCDII). In one embodiment, the antibody is an antibody that comprises the heavy and light chain CDRs (e.g. according to the Kabat numbering scheme) of an antibody selected from the group consisting of antibody 8B6A, 8B6B, 9H11A, 9H11B and 17E1. In one embodiment, the antibody is an antibody that competes for binding to NKp46 with antibody 8B6A, 8B6B, 9H11A, 9H11B or 17E1, or an antibody that binds to the same epitope as any one of the foregoing, and/or an antibody that binds to at least one residue in the segment corresponding to residues 100-187 of the NKp46 polypeptide of SEQ ID NO:1.

The methods of treatment the anti-NKp46 antibody can be used to a treat an individual in combination with a second therapeutic agent, including an anti-cancer agent when used to treat cancer (e.g., chemotherapeutic drugs, tumor vaccines, antibodies that bind to tumor-specific antigens on tumor cells, antibodies that deplete tumor cells, antibodies that potentiate immune responses, etc.).

Further provided is a method for selecting subjects having a disorder (e.g., a cancer) that responds to a treatment using an anti-NKp46 agent of the disclosure (e.g., an antibody that binds to a NKp46 polypeptide), the method comprising determining whether cells (e.g., tumor cells) in said subject express a NKp46 polypeptide, the expression of a NKp46 polypeptide being indicative of a responder subject. In one embodiment, the method comprises determining whether cells (e.g., tumor cells, pro-inflammatory cells, etc.) in said subject express a NKp46 polypeptide having the amino acid sequence of SEQ ID NO: 1. In one embodiment, the step of determining whether cells in said subject express a NKp46 polypeptide comprising bringing a biological sample from the subject (e.g., by obtaining a sample of cancer cells, a blood or any tissue sample, etc.) into contact with an anti-NKp46 antibody of the disclosure.

Optionally, in any of the methods, the method further comprises administering to a responder subject an antibody (e.g., an anti-NKp46 antibody of the disclosure) that binds to a NKp46 polypeptide.

In a preferred embodiment, the expression of a NKp46 polypeptide in a disease-related cell is determined using a NKp46-specific ligand. Preferably, the ligand is an antibody, or a fragment or derivative thereof.

In another aspect, provided is a method (e.g., a method of conducting a diagnostic assay, a responder assay, etc.), comprising assessing whether a patient has disease-related cells (e.g., tumor cells) expressing a NKp46 polypeptide, e.g., a NKp46 polypeptide (one or more NKp46 alleles) bound by an antibody of the disclosure. Said method may comprise, for example, obtaining a biological sample from a patient comprising disease-related cells, bringing said disease-related cells into contact with such antibody and assessing whether the antibody binds to disease-related cells. A finding that NKp46 is expressed by disease-related cells indicates that the patient has a condition characterized by NKp46-expressing cells and/or is suitable for treatment with an anti-NKp46 antibody of the disclosure. The patient can further be treated with a treatment suitable for the particular disease characterized by NKp46-expressing cells. Optionally the patient is treated with the anti-NKp46 antibody. In one embodiment, the method is used for selecting subjects having a cancer, and the disease-related cells are cancer cells.

Also provided is a method of treating an individual, the method comprising:
a) determining whether the individual has pathogenic NKp46-expressing cells, and
b) if the individual is determined to patient have pathogenic NKp46-expressing cells, administering an antigen-binding compound (e.g., antibody) of the disclosure.

In one embodiment, provided is a method for treating or preventing a peripheral T cell lymphoma in an individual, the method comprising administering to an individual a therapeutically active amount of an anti-NKp46 antigen binding compound disclosed herein. In one aspect, a composition comprising an anti-NKp46 compound can be used in the treatment or prevention of LDGL (lymphoproliferative disease of granular lymphocytes), optionally NK-LDGL (NK-type lymphoproliferative disease of granular lymphocytes; alternatively called NK-LGL). In one aspect, a composition comprising an anti-NKp46 compound can be used in the treatment or prevention of peripheral T cell lymphoma. Optionally the said treatment or prevention comprises administration of a compound that binds a NKp46 polypeptide to an individual having a PTCL (including a condition susceptible to progressing to a PTCL). In one embodiment of any of the therapeutic uses or PTCL treatment or prevention methods herein, the individual has a NK/T-lymphoma. In one embodiment of any of the therapeutic uses or PTCL treatment or prevention methods herein, the individual has an enteropathy associated T cell lymphoma (EATL), a RCDI or an RCDII. In one embodiment of any of the therapeutic uses or PTCL treatment or prevention methods herein, the individual has an anaplastic large cell lymphoma (ALCL). In one embodiment of any of the therapeutic uses or PTCL treatment or prevention methods herein, the individual has a PTCL-NOS. In one embodiment of any of the therapeutic uses or PTCL treatment or prevention methods herein, the treatment or prevention of a PTCL (e.g., an EATL, RCDI, RCDII, an ALCL, a PTCL-NOS) in an individual comprises:
a) determining the NKp46 polypeptide status of malignant cells within the individual having a PTCL, and
b) upon a determination that the patient that a NKp46 polypeptide prominently expressed on the surface of malignant cells, administering to the individual a compound that binds a NKp46 polypeptide of any of the embodiments herein.

In one embodiment of any aspect herein, the PTCL is an aggressive and/or advanced PTCL. In one embodiment, the PTCL is aggressive non-cutaneous PTCL. In one embodiment, the PTCL is PTCL-NOS (also referred to as PCTL-U). In one embodiment, the PTCL is a nodal (e.g., primarily nodal) PTCL, for example a PTCL-NOS, AITL, or ALCL (ALK+ or ALK−). In one embodiment, the PTCL is an anaplastic large cell lymphoma (ALCL), optionally an ALK− negative ALCL. In one embodiment, the PTCL is an angioimmunoblastic T-cell lymphoma (AITL), optionally a cutaneous AITL, optionally a non-cutaneous AITL. In one embodiment, a PTCL may be an aggressive, non-cutaneous, primarily nodal PCTL. In one embodiment, the PTCL is an extranodal (e.g., primarily extranodal) PTCL. In one example a PTCL may be an aggressive, non-cutaneous, extranodal PCTL. In one embodiment, the PTCL is an adult T cell leukemia or lymphoma (ATL), e.g., an HTLV+ ATL. In one embodiment, the PTCL is an orthovisceral extranodal disease, e.g., NK-/T cell lymphoma or an enteropathy-associated T cell lymphoma. In one embodiment, the PTCL is an extranodal NK-/T-cell lymphoma, nasal type. In one embodiment, the PTCL is RCDI, RCDII, an enteropathy-associated T cell lymphoma (EATL).

These and additional advantageous aspects and features of the invention may be further described elsewhere herein.

DETAILED DESCRIPTION OF THE INVENTION

Definitions

Figure 1:
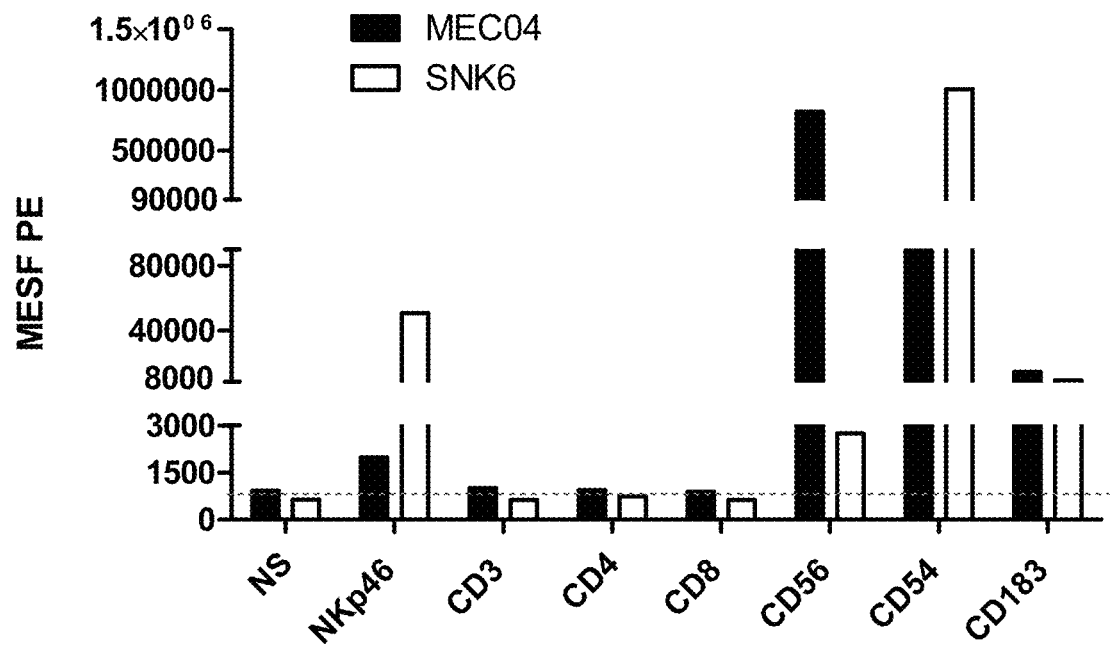
FIG. 1 shows staining by anti-NKp46 antibody on NK-/T-lymphoma cells. The figure additionally shows that the NKp46-positive cells express CD183 (CXCR3), CD56 and CD54 (ICAM).

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can be replaced by "consisting essentially of", or by "consisting of".

"NKp46 polypeptide" and "NKp46 receptor" refer to a protein or polypeptide encoded by the Ncr1 gene or by a cDNA prepared from such a gene. Any naturally occurring isoform, allele or variant is encompassed by the term NKp46 polypeptide (e.g., an NKp46 polypeptide 90%, 95%, 98% or 99% identical to SEQ ID NO: 1, or a contiguous sequence of at least 20, 30, 50, 100 or 200 amino acid residues thereof). The 304 amino acid residue sequence of human NKp46 (isoform a) is shown as follows:

```
                                    (SEQ ID NO: 1)
     MSSTLPALLC VGLCLSQRIS AQQQTLPKPF

IWAEPHFMVP KEKQVTICCQ GNYGAVEYQL

HFEGSLFAVD RPKPPERINK VKFYIPDMNS

RMAGQYSCIY RVGELWSEPS NLLDLVVTEM

YDTPTLSVHP GPEVISGEKV TFYCRLDTAT
```

-continued
```
     SMFLLLKEGR SSHVQRGYGK VQAEFPLGPV

TTAHRGTYRC FGSYNNHAWS FPSEPVKLLV

TGDIENTSLA PEDPTFPADT WGTYLLTTET

GLQKDHALWD HTAQNLLRMG LAFLVLVALV

WFLVEDWLSR KRTRERASRA STWEGRRRLN

TQTL.
```

SEQ ID NO: 1 corresponds to NCBI accession number NP_004820, the disclosure of which is incorporated herein by reference. The human NKp46 mRNA sequence is described in NCBI accession number NM_004829, the disclosure of which is incorporated herein by reference.

Certain aspects of the present disclosure provide anti-NKp46 antibodies that bind to a human NKp46, or a homolog thereof, including without limitation a mammalian NKp46 protein and NKp46 orthologs from other species, e.g. non-human primates, Macaca fascicularis.

Whenever within this whole specification "treatment of a proliferative disease" or "treatment of a tumor", or "treatment of cancer" or the like is mentioned with reference to anti-NKp46 binding agent (e.g., antibody), there is meant: (a) method of treatment of a proliferative disease, said method comprising the step of administering (for at least one treatment) an anti-NKp46 binding agent, (preferably in a pharmaceutically acceptable carrier material) to a warm-blooded animal, especially a human, in need of such treatment, in a dose that allows for the treatment of said disease (a therapeutically effective amount), preferably in a dose (amount) as specified to be preferred hereinabove and herein below; (b) the use of an anti-NKp46 binding agent for the treatment of a proliferative disease, or an anti-NKp46 binding agent, for use in said treatment (especially in a human); (c) the use of an anti-NKp46 binding agent, for the manufacture of a pharmaceutical preparation for the treatment of a proliferative disease, a method of using an anti-NKp46 binding agent for the manufacture of a pharmaceutical preparation for the treatment of a proliferative disease, comprising admixing an anti-NKp46 binding agent with a pharmaceutically acceptable carrier, or a pharmaceutical preparation comprising an effective dose of an anti-NKp46 binding agent that is appropriate for the treatment of a proliferative disease; or (d) any combination of a), b), and c), in accordance with the subject matter allowable for patenting in a country where this application is filed.

The term "transglutaminase", used interchangeably with "TGase" or "TG", refers to an enzyme capable of cross-linking proteins through an acyl-transfer reaction between the γ-carboxamide group of peptide-bound glutamine and the ε-amino group of a lysine or a structurally related primary amine such as amino pentyl group, e.g., a peptide-bound lysine, resulting in a ε-(γ-glutamyl)lysine isopeptide bond. TGases include, inter alia, bacterial transglutaminase (BTG) such as the enzyme having EC reference EC 2.3.2.13 (protein-glutamine-γ-glutamyltransferase).

The term "acceptor glutamine residue", when referring to a glutamine residue of an antibody, means a glutamine residue that is recognized by a TGase and can be cross-linked by a TGase through a reaction between the glutamine and a lysine or a structurally related primary amine such as amino pentyl group. Preferably the acceptor glutamine residue is a surface-exposed glutamine residue.

The term "TGase recognition tag" refers to a sequence of amino acids comprising an acceptor glutamine residue and that when incorporated into (e.g., appended to) a polypeptide sequence, under suitable conditions, is recognized by a TGase and leads to cross-linking by the TGase through a reaction between an amino acid side chain within the sequence of amino acids and a reaction partner. The recognition tag may be a peptide sequence that is not naturally present in the polypeptide comprising the enzyme recognition tag.

The terms "cancer" and "tumor" as used herein are defined as a new growth of cells or tissue comprising uncontrolled and progressive multiplication. In a specific embodiment, upon a natural course the cancer is fatal.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG can readily be employed because they are the most common antibodies in the physiological situation and because they are most easily made in a laboratory setting. The antibody can be a monoclonal antibody. Particularly preferred are humanized, chimeric, human, or otherwise-human-suitable antibodies. "Antibodies" also includes any fragment or derivative of any of the herein described antibodies.

The term "hypervariable region" when used herein refers to the amino acid residues of an antibody that are responsible for antigen binding. The hypervariable region generally comprises amino acid residues from a "complementarity-determining region" or "CDR" (e.g., residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g., residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

When an antibody is said to "compete with" a particular monoclonal antibody (e.g., 8B6A, 8B6B, 9H11A, 9H11B or 17E1), it means that the antibody competes with the monoclonal antibody in a binding assay using either recombinant NKp46 molecules or surface expressed NKp46 molecules. For example, if a test antibody reduces the binding of 8B6A, 8B6B, 9H11A, 9H11B or 17E1 to a NKp46 polypeptide or NKp46-expressing cell in a binding assay, the antibody is said to "compete" respectively with 68B6A, 8B6B, 9H11A, 9H11B or 17E1

The term "affinity", as used herein, means the strength of the binding of an antibody to an epitope. The affinity of an antibody is given by the dissociation constant $K_D$, defined as [Ab] x [Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of surface plasmon resonance (SPR) screening (such as by analysis with a BIAcore™ SPR analytical device).

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous (or discontinuous) and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "depleting", with respect to NKp46-expressing cells means a process, method, or compound that can kill, eliminate, lyse or induce such killing, elimination or lysis, so as to negatively affect the number of NKp46-expressing cells present in a sample or in a subject.

The terms "immunoconjugate" and "antibody conjugate" are used interchangeably and refer to an antigen binding agent, e.g., an antibody binding polypeptide or an antibody that is conjugated to another moiety (e.g., a detectable moiety, a therapeutic agent, a cytotoxic agent, an anti-cancer agent). When an immunoconjugate comprises an antigen binding agent conjugated to a therapeutic agent, e.g., a cytotoxic agent or anti-cancer agent, the immunoconjugate can also be referred to as a "antibody drug conjugate" or an "ADC".

The term "agent" is used herein to denote a chemical compound, a mixture of chemical compounds, a biological macromolecule, or an extract made from biological materials. The term "therapeutic agent" refers to an agent that has biological activity.

The terms "toxic agent" and "cytotoxic agent" encompass any compound that can slow down, halt, or reverse the proliferation of cells, decrease their activity in any detectable way, or directly or indirectly kill them. Cytotoxic agents may cause cell death primarily by interfering directly with the cell's functioning, and include, but are not limited to, alkylating agents, tumor necrosis factor inhibitors, DNA intercalators, DNA minor groove binding agents, microtubule inhibitors, kinase inhibitors, proteasome inhibitors and topoisomerase inhibitors. A "toxic payload" as used herein refers to a sufficient amount of cytotoxic agent which, when delivered to a cell results in cell death. Delivery of a toxic payload may be accomplished by administration of a sufficient amount of immunoconjugate comprising an antibody or antigen binding fragment of the disclosure and a cytotoxic agent. Delivery of a toxic payload may also be accomplished by administration of a sufficient amount of an immunoconjugate comprising a cytotoxic agent, wherein the immunoconjugate comprises a secondary antibody or antigen binding fragment thereof which recognizes and binds an antibody of the disclosure.

A "humanized" or "human" antibody refers to an antibody in which the constant and variable framework region of one or more human immunoglobulins is fused with the binding region, e.g., the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, MD, also referred to as "Kabat EU").

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

The term "complement-dependent cytotoxicity" or "CDC" is a term well understood in the art, and refers to the ability of a molecule to lyse a target in the presence of complement. The complement activation pathway is initiated by the binding of the first component of the complement system (C1q) to a molecule (e.g., an antibody) complexed with a cognate antigen.

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" comprises events wherein intracellular internalization is initiated and/or the rate and/or extent of intracellular internalization is increased.

By "amino acid modification" herein is meant an amino acid substitution, insertion, and/or deletion in a polypeptide sequence. An example of amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. Any compound, e.g., antibody, described herein can optionally be described as being isolated, purified or biologically pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

As used herein, "NK cells", also referred to "natural killer cells", refers to a sub-population of lymphocytes that is involved in non-conventional immunity. NK cells can be identified by virtue of certain characteristics and biological properties, such as the expression of specific surface antigens including CD56 and/or CD16 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response.

An antibody that "binds" a polypeptide or epitope designates an antibody that binds said determinant with specificity and/or affinity.

Producing Anti-NKp46 Antibodies

The hypervariable regions, heavy and light chain CDRs, heavy and light chain variable regions, and protein (e.g., antibodies) that comprise them, will bind human (and optionally further non-human primate) NKp46 expressed on the surface of a cell, e.g., a tumor cell, an NK cell, etc. When used in therapy for the elimination of NKp46-expressing tumor cells (e.g., malignant T cells) or for elimination of other immune cells, the antibodies will typically be depleting, for example by directly causing the death of NKp46-expressing tumor cells when conjugated to a cytotoxic moiety, and/or by directing immune effector cells (e.g. NK cells, T cells, macrophages), ADCC, ADCP (antibody dependent cellular phagocytosis) and/or CDC toward tumor cells. When used in other applications, e.g., for detection of, for identification of, for isolation of, and/or more generally for binding to human and/or non-human primate NKp46 polypeptides and/or NKp46-expressing cells (e.g., NK cells), the antibodies need not be depleting.

In one embodiment, the antibody competes for binding to the NKp46 polypeptide with any one or more of antibodies 8B6A, 8B6B, 9H11A, 9H11B or 17E1. Preferably the antibody recognizes, binds to, or has immunospecificity for substantially or essentially the same, or the same, epitope or "epitopic site" on a NKp46 polypeptide. In one embodiment, the antibodies do not compete for binding to NKp46 with any of the antibodies Bab281, 9E2 or 195314 (reported to be blocking).

The antibodies of the disclosure may be produced by a variety of techniques known in the art. Typically, they are produced by immunization of a non-human animal, preferably a mouse, with an immunogen comprising a NKp46 polypeptide, preferably a human NKp46 polypeptide. The NKp46 polypeptide may comprise the full length sequence of a human NKp46 polypeptide, or a fragment or derivative thereof, typically an immunogenic fragment, i.e., a portion of the polypeptide comprising an epitope exposed on the surface of cells expressing a NKp46 polypeptide, preferably the epitope recognized by the 8B6A, 8B6B, 9H11A, 9H11B or 17E1 antibody. Such fragments typically contain at least about 7 consecutive amino acids of the mature polypeptide sequence, even more preferably at least about 10 consecutive amino acids thereof. Fragments typically are essentially derived from the extra-cellular domain of the receptor. In one embodiment, the immunogen comprises a wild-type human NKp46 polypeptide in a lipid membrane, typically at the surface of a cell. In a specific embodiment, the immunogen comprises intact cells, particularly intact human cells, optionally treated or lysed. In another preferred embodiment, the polypeptide is a recombinant NKp46 polypeptide. In a specific embodiment, the immunogen comprises intact NKp46-expressing cells.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, NY (1988), the entire disclosure of which is herein incorporated by reference).

Antibodies may also be produced by selection from combinatorial libraries of immunoglobulins, as disclosed for instance in (Ward et al. Nature, 341 (1989) p. 544, the entire disclosure of which is herein incorporated by reference).

The identification of one or more antibodies that bind(s) to NKp46, particularly substantially or essentially the same region as monoclonal antibody 8B6A, 8B6B, 9H11A, 9H11B or 17E1, can be readily determined using any one of a variety of immunological screening assays in which antibody competition can be assessed. Many such assays are routinely practiced and are well known in the art (see, e. g., U.S. Pat. No. 5,660,827, which is incorporated herein by reference).

For example, where the test antibodies to be examined are obtained from different source animals, or are even of a different Ig isotype, a simple competition assay may be employed in which the control (8B6A, 8B6B, 9H11A, 9H11B or 17E1, for example) and test antibodies are admixed (or pre-adsorbed) and applied to a sample containing NKp46 polypeptides. Protocols based upon western blotting and the use of BIACORE analysis are suitable for use in such competition studies.

In certain embodiments, one pre-mixes the control antibodies (8B6A, 8B6B, 9H11A, 9H11B or 17E1, for example) with varying amounts of the test antibodies (e.g., about 1:10 or about 1:100) for a period of time prior to applying to the NKp46 antigen sample. In other embodiments, the control and varying amounts of test antibodies can simply be admixed during exposure to the NKp46 antigen sample. As long as one can distinguish bound from free antibodies (e. g., by using separation or washing techniques to eliminate unbound antibodies) and 8B6A, 8B6B, 9H11A, 9H11B or 17E1 from the test antibodies (e. g., by using species-specific or isotype-specific secondary antibodies or by specifically labeling 8B6A, 8B6B, 9H11A, 9H11B or 17E1 with a detectable label) one can determine if the test antibodies reduce the binding of 8B6A, 8B6B, 9H11A, 9H11B or 17E1 to the antigens, indicating that the test antibody recognizes a region containing residues of the epitope of 8B6A, 8B6B, 9H11A, 9H11B or 17E1. The binding of the (labeled)

control antibodies in the absence of a completely irrelevant antibody can serve as the control high value. The control low value can be obtained by incubating the labeled (8B6A, 8B6B, 9H11A, 9H11B or 17E1) antibodies with unlabelled antibodies of exactly the same type (8B6A, 8B6B, 9H11A, 9H11B or 17E1), where competition would occur and reduce binding of the labeled antibodies. In a test assay, a significant reduction in labeled antibody reactivity in the presence of a test antibody is indicative of a test antibody that recognizes substantially the same region, i.e., one that "cross-reacts" or competes with the labeled (8B6A, 8B6B, 9H11A, 9H11B or 17E1) antibody. Any test antibody that reduces the binding of 8B6A, 8B6B, 9H11A, 9H11B or 17E1 to NKp46 antigens by at least about 50%, such as at least about 60%, or more preferably at least about 80% or 90% (e. g., about 65-100%), at any ratio of 8B6A, 8B6B, 9H11A, 9H11B or 17E1:test antibody between about 1:10 and about 1:100 is considered to be an antibody that binds to substantially the same region or determinant as 8B6A, 8B6B, 9H11A, 9H11B or 17E1. Preferably, such test antibody will reduce the binding of 8B6A, 8B6B, 9H11A, 9H11B or 17E1 to the NKp46 antigen by at least about 90% (e.g., about 95%).

Competition can also be assessed by, for example, a flow cytometry test. In such a test, cells bearing a given NKp46 polypeptide can be incubated first with 8B6A, 8B6B, 9H11A, 9H11B or 17E1, for example, and then with the test antibody labeled with a fluorochrome or biotin. The antibody is said to compete with 8B6A, 8B6B, 9H11A, 9H11B or 17E1 if the binding obtained upon preincubation with a saturating amount of 8B6A, 8B6B, 9H11A, 9H11B or 17E1 is about 80%, preferably about 50%, about 40% or less (e.g., about 30%, 20% or 10%) of the binding (as measured by mean of fluorescence) obtained by the antibody without preincubation with 8B6A, 8B6B, 9H11A, 9H11B or 17E1. Alternatively, an antibody is said to compete with 8B6A, 8B6B, 9H11A, 9H11B or 17E1 if the binding obtained with a labeled 8B6A, 8B6B, 9H11A, 9H11B or 17E1 antibody (by a fluorochrome or biotin) on cells preincubated with a saturating amount of test antibody is about 80%, preferably about 50%, about 40%, or less (e. g., about 30%, 20% or 10%) of the binding obtained without preincubation with the test antibody.

A simple competition assay in which a test antibody is pre-adsorbed and applied at saturating concentration to a surface onto which a NKp46 antigen is immobilized may also be employed. The surface in the simple competition assay is preferably a BIACORE chip (or other media suitable for surface plasmon resonance analysis). The control antibody (e.g., 8B6A, 8B6B, 9H11A, 9H11B or 17E1) is then brought into contact with the surface at a NKp46-saturating concentration and the NKp46 and surface binding of the control antibody is measured. This binding of the control antibody is compared with the binding of the control antibody to the NKp46-containing surface in the absence of test antibody. In a test assay, a significant reduction in binding of the NKp46-containing surface by the control antibody in the presence of a test antibody indicates that the test antibody recognizes substantially the same region on the surface of NKp46 as the control antibody such that the test antibody "cross-reacts" with the control antibody. Any test antibody that reduces the binding of control (such as 8B6A, 8B6B, 9H11A, 9H11B or 17E1) antibody to a NKp46 antigen by at least about 30% or more, preferably about 40%, can be considered to be an antibody that binds to substantially the same region as a control (e.g., 8B6A, 8B6B, 9H11A, 9H11B or 17E1). Preferably, such a test antibody will reduce the binding of the control antibody (e.g., 8B6A, 8B6B, 9H11A, 9H11B or 17E1) to the NKp46 antigen by at least about 50% (e. g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the NKp46 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

The antibodies will bind to NKp46-expressing cells from an individual or individuals with a disease characterized by expression of NKp46-positive cells, i.e., an individual that is a candidate for treatment with one of the herein-described methods using an anti-NKp46 antibody. Accordingly, once an antibody that specifically recognizes NKp46 on cells is obtained, it can optionally be tested for its ability to bind to NKp46-positive cells (e.g., cancer cells). In particular, prior to treating a patient with one of the present antibodies, one may optionally test the ability of the antibody to bind malignant cells taken from the patient, e.g., in a blood sample or tumor biopsy, to maximize the likelihood that the therapy will be beneficial in the patient.

In one embodiment, the antibodies are validated in an immunoassay to test their ability to bind to NKp46-expressing cells, e.g., malignant cells. For example, a blood sample or tumor biopsy is performed and tumor cells are collected. The ability of a given antibody to bind to the cells is then assessed using standard methods well known to those in the art. To assess the binding of the antibodies to the cells, the antibodies can either be directly or indirectly labeled. When indirectly labeled, a secondary, labeled antibody is typically added.

Determination of whether an antibody binds within an epitope region can be carried out in ways known to the person skilled in the art. As one example of such mapping/characterization methods, an epitope region for an anti-NKp46 antibody may be determined by epitope "footprinting" using chemical modification of the exposed amines/carboxyls in the NKp46 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e. g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e. g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. Protease digestion techniques also can be useful in the context of epitope mapping and identification. Antigenic determinant-relevant regions/sequences can be determined by protease digestion, e.g., by using trypsin in a ratio of about 1:50 to NKp46 or o/n digestion at and pH 7-8, followed by mass spectrometry (MS) analysis for peptide identification. The peptides protected from trypsin cleavage by the anti-NKp46 binder can subsequently be identified by comparison of samples subjected to trypsin digestion and samples incubated with antibody and then subjected to digestion by e.g., trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the NKp46 polypeptide that is not surface exposed and, accordingly, most likely not relevant in terms of immunogenicity/antigenicity.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kröger et al., Biosensors and Bioelectronics 2002; 17:937-944.

It should also be noted that an antibody binding the same or substantially the same epitope as an antibody can be identified in one or more of the exemplary competition assays described herein.

Upon immunization and production of antibodies in a vertebrate or cell, particular selection steps may be performed to isolate antibodies as claimed. In this regard, in a specific embodiment, provided are methods of producing such antibodies, comprising: (a) immunizing a non-human mammal with an immunogen comprising a NKp46 polypeptide; and (b) preparing antibodies from said immunized animal; and (c) selecting antibodies from step (b) that are capable of binding NKp46.

In one aspect provided is an antibody that has an average disassociation constant ($K_D$), optionally for monovalent binding, of less than $1\times10^{-8}$ M, optionally less than $1\times10^{-9}$ M, with respect to human NKp46, as determined by, e.g., surface plasmon resonance (SPR) screening (such as by analysis with a BIAcore™ SPR analytical device). In a more particular exemplary aspect, provided are anti-NKp46 antibodies that have a KD of about $1\times10^{-8}$ M to about $1\times10^{-10}$ M, or about $1\times10^{-9}$ M to about $1\times10^{-11}$ M, for NKp46.

Antibodies can be characterized for example by a mean KD of no more than about (i.e., better affinity than) 100, 60, 10, 5, or 1 nanomolar, preferably sub-nanomolar or optionally no more than about 500, 200, 100 or 10 picomolar. KD can be determined for example for example by immobilizing recombinantly produced human NKp46 proteins on a chip surface, followed by application of the antibody to be tested in solution. In one embodiment, the method further comprises a step (d), selecting antibodies from (b) that are capable of competing for binding to NKp46 with antibody 8B6A, 8B6B, 9H11A, 9H11B or 17E1.

In one aspect of any of the embodiments, the antibodies prepared according to the present methods are monoclonal antibodies. In another aspect, the non-human animal used to produce antibodies is a mammal, such as a rodent, bovine, porcine, fowl, horse, rabbit, goat, or sheep. Antibodies of the invention can optionally be specified to be antibodies other than any of antibodies 195314, 9E2 or Bab281, or derivatives thereof, e.g., that comprise their respective heavy and light chain CDRs or the antigen binding region in whole or in part.

DNA encoding an antibody that binds an epitope present on NKp46 polypeptides is isolated from a hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies, e.g., antibody 8B6A, 8B6B, 9H11A, 9H11B or 17E1, can be readily isolated and sequenced using conventional procedures (e. g., by using oligonucleotide probes that are capable of binding specifically to genes encoding the heavy and light chains of murine antibodies). In one aspect, provided is a nucleic acid encoding a heavy chain or a light chain of an anti-NKp46 antibody of any embodiment herein. Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody. In one embodiment, provided is an isolated nucleic acid sequence encoding a light chain and/or a heavy chain of an antibody (e.g., 8B6A, 8B6B, 9H11A, 9H11B or 17E1), as well as a recombinant host cell comprising (e.g., in its genome) such nucleic acid.

Once an antibody is obtained it will generally be assessed for its activity. For example, the antibody can be tested for its ability to inhibit the proliferation of and/or cause the elimination of a NKp46-expressing target cell. For example, the antibody can be conjugated to a cytotoxic agent, e.g., as further described herein, and assessed for the ability to deplete a target cell. In another example, the ability to induce ADCC, ADCP or CDC towards an NKp46-expressing target cell is assessed.

Testing CDC, ADCP and ADCC can be carried out can be determined by various assays including those described in the experimental examples herein. Testing ADCC typically involves assessing cell-mediated cytotoxicity in which a NKp46-expressing target cell (e.g., a cancer or other NKp46-expressing cell) with bound anti-NKp46 antibody is recognized by an effector cell (e.g., a leukocyte bearing Fc receptors), without the involvement of complement. A cell which does not express a NKp46 antigen can optionally be used as a control. Activation of NK cell cytotoxicity is assessed by measuring an increase in cytokine production (e.g., IFN-γ production) or cytotoxicity markers (e.g., CD107 mobilization). An antibody that induces ADCC will typically induce an increase in cytokine production, expression of cytotoxicity markers, or target cell lysis of at least 50%, 80%, 100% or more in the presence of target (NKp46-expressing) cells, compared to a control antibody (e.g., an antibody not binding to NKp46, an anti-NKp46 antibody having murine constant regions). In another example, lysis of target cells is detected, e.g., in a chromium release assay, the antibody can for example induce lysis of at least 40% or 50% of target cells.

Testing the ability of an immunoconjugate to deplete a target cell can be carried out by any of a number of assays, known in the art, for determining whether an immunoconjugate exerts a cytostatic or cytotoxic effect on a desired cell line. For example, the cytotoxic or cytostatic activity of an immunoconjugate can be measured by: exposing mammalian cells expressing NKp46 in a cell culture medium; culturing the cells for a period from about 6 hours to about 5 days; and measuring cell viability. Cell-based in vitro assays can be used to measure viability (proliferation), cytotoxicity, and induction of apoptosis (caspase activation).

Cell viability can be measured by assessing ATP production by NKp46-expressing cells in culture, for example as described in the Examples herein.

In other examples, a thymidine incorporation assay may be used. For example, cancer cells expressing NKp46 at a density of 5,000 cells/well of a 96-well plated can be cultured for a 72-hour period and exposed to 0.5 μCi of $^3$H-thymidine during the final 8 hours of the 72-hour period. The incorporation of $^3$H-thymidine into cells of the culture is measured in the presence and absence of the immunoconjugate.

In another example determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an immunoconjugate is useful in the treatment of cancers.

Cell viability can also be measured by determining in a cell the uptake of a dye such as neutral red, trypan blue, or ALAMAR™ blue. In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity. Alternatively, a tetrazolium salt, such as MTT or WST, is used in a quantitative colorimetric assay for mammalian cell survival and proliferation by detecting living, but not dead, cells.

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays. Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., (1995), Cancer Research 55: 3110-16).

Antibody Epitopes

In one embodiment, the antibodies bind the same or substantially the same epitope as antibody 8B6A, 8B6B, 9H11A, 9H11B or 17E1. In one embodiment, the antibodies bind to an epitope of NKp46 that at least partially overlaps with, or includes at least one residue in, the epitope bound by antibody 8B6A, 8B6B, 9H11A, 9H11B or 17E1. The residues bound by the antibody can be specified as being present on the surface of the of the NKp46 polypeptide, e.g., in a NKp46 polypeptide expressed on the surface of a cell.

In another embodiment, the antibodies bind an epitope which at least partially overlaps, or includes at least one residue in the segment corresponding to residues 100-187, e.g. residues 101 to 118 (or 101 to 105 or 100 to 105), residues 150 to 169, residues 135 to 151 (or 133 to 151) and/or residues 178 to 187 (or 177 to 187) of the NKp46 polypeptide of SEQ ID NO: 70. In one embodiment, all key residues of the epitope are in a segment corresponding to residues 100 to 187, or in residues 101 to 118 (or 101 to 105 or 100 to 105), residues 150 to 169, residues 135 to 151 (or 133 to 151) and/or residues 178 to 187 (or 177-187), of the NKp46 polypeptide of SEQ ID NO: 70. In one embodiment, the antibodies bind an epitope comprising 1, 2, 3, 4, 5, 6, 7 or more residues in the segment corresponding to residues 100 to 187, residues 101 to 118 (or 101 to 105 or 100 to 105), residues 150 to 169, residues 135 to 151 (or 133 to 151) or residues 178 to 187 (or 177 to 187) of the NKp46 polypeptide of SEQ ID NO: 70. In another embodiment, the antibodies bind an epitope comprising 1, 2, 3, 4, 5, 6, 7 or more residues in the segment corresponding to residues 101-118 or 100-105 or 101-105 and 1, 2, 3, 4, 5, 6, 7 or more residues in the segment corresponding to residues 150-169 of the NKp46 polypeptide of SEQ ID NO: 70.

It will be appreciated that the amino acid residues and/or segments indicated with reference to the NKp46 amino acid sequence of SEQ ID NO: 70 can alternatively be expressed with reference to the NKp46 amino acid sequence of SEQ ID NO: 1. For example: residues 100-118 of SEQ ID NO: 70 correspond to residues 121-139 of SEQ ID NO: 1; residues 101-118 of SEQ ID NO: 70 correspond to residues 122-139 of SEQ ID NO: 1; residues 101-105 of SEQ ID NO: 70 correspond to residues 122-126 of SEQ ID NO: 1; residues 100-105 of SEQ ID NO: 70 correspond to residues 121-126 of SEQ ID NO: 1; residues 133-151 of SEQ ID NO: 70 correspond to residues 154-172 of SEQ ID NO: 1; residues 135-151 of SEQ ID NO: 70 correspond to residues 156-172 or SEQ ID NO: 1; residues 150-169 of SEQ ID NO: 70 correspond to residues 171-190 of SEQ ID NO: 1; residues 177-187 of SEQ ID NO: 70 correspond to residues 198-208 of SEQ ID NO: 1; residues 178-187 of SEQ ID NO: 70 correspond to residues 199-208 of SEQ ID NO: 1.

In another embodiment, an antibody or agent of the disclosure binds to one or more amino acid residues within a segment of the NKp46 polypeptide having the amino acid sequence DTPTLSVHPGPEVISGEK (SEQ ID NO: 71). Optionally, an antibody or agent of the disclosure further binds to one or more amino acid residues within a segment of the NKp46 polypeptide having the amino acid sequence VQAEFPLGPVTTAHRGTYRC (SEQ ID NO: 72).

In another embodiment, an antibody or agent of the disclosure binds to one or more amino acid residues within a segment of the NKp46 polypeptide having the amino acid sequence DTPTL (SEQ ID NO: 73). Optionally, an antibody or agent of the disclosure further binds to one or more amino acid residues within a segment of the NKp46 polypeptide having the amino acid sequence VQAEFPLGPVTTAHRG-TYRC(SEQ ID NO: 72).

In another embodiment, an antibody or agent of the disclosure binds to one or more amino acid residues within a segment of the NKp46 polypeptide having the amino acid sequence VQAEFPLGPVTTAHRGTYRC (SEQ ID NO: 72).

In any embodiment, an antibody or agent of the disclosure may optionally further bind to one or more amino acid residues within a segment of the NKp46 polypeptide having the amino acid sequence WSFPSEPVKL (SEQ ID NO: 74).

In any embodiment, an antibody or agent of the disclosure may optionally further bind to one or more amino acid residues within a segment of the NKp46 polypeptide having the amino acid sequence AWSFPSEPVKL (SEQ ID NO: 75).

In any embodiment, an antibody or agent of the disclosure may optionally further bind to one or more amino acid residues within a segment of the NKp46 polypeptide having the amino acid sequence LKEGRSSHVQRGYGKVQ (SEQ ID NO: 76).

In any embodiment, an antibody or agent of the disclosure may optionally further bind to one or more amino acid residues within a segment of the NKp46 polypeptide having the amino acid sequence LLLKEGRSSHVQRGYGKVQ (SEQ ID NO: 77).

In any embodiment, an antibody or agent of the disclosure may bind one or more amino acids present on the surface of the NKp46 polypeptide within the epitopes bound by the anti-NKp46 antibodies of the invention. In one such embodiment, the antibodies bind 1, 2 or 3 residues selected from the group consisting of 101, 102 and 104 of the NKp46 polypeptide of SEQ ID NO: 70 (residues 122, 123 and 125 of the polypeptide of SEQ ID NO: 1).

In one embodiment, the antibodies bind 1, 2, 3, 4, 5, 6, 7 or more residues selected from the group consisting of V150, Q151, E153, P155, G157, P158, T160, T161, A162, H163, R164, T166 and R168 of the NKp46 polypeptide of SEQ ID NO: 70 (residues 171, 172, 174, 176, 179, 181, 182, 183, 184, 185, 187 and 189 of the polypeptide of SEQ ID NO: 1). Optionally, the antibodies further bind 1, 2, 3, 4, 5, 6, 7 or more residues selected from the group consisting of Y100, D101, T102 and T104, of the NKp46 polypeptide of SEQ ID NO: 70.

In one embodiment, the antibodies bind 1, 2, 3, 4, 5, 6, 7 or more residues selected from the group consisting of D101, T102, T104, S106, H108, P109, P111, E112, I114, S115, G116, E117, K118, V150, Q151, E153, P155, G157, P158, T160, T161, A162, H163, R164, T166 and R168 of the NKp46 polypeptide of SEQ ID NO: 70. In another embodiment, the antibodies bind 1, 2, 3, 4, 5, 6, 7 or more residues selected from the group consisting of D101, T102, T104, V150, Q151, E153, P155, G157, P158, T160, T161, A162, H163, R164, T166 and R168 of the NKp46 polypeptide of SEQ ID NO: 70.

In one aspect, provided is an anti-NKp46 antibody that has reduced binding to a NKp46 polypeptide having a mutation at one, two or three of the residues selected from the group consisting of: 101, 102 and 104 with reference to SEQ ID NO: 70 (residues 122, 123 and 125 of the polypeptide of SEQ ID NO: 1).

In one aspect, provided is an anti-NKp46 antibody that has reduced binding to a NKp46 polypeptide having a mutation at one, two, three of more of (or all of) the residues selected from the group consisting of: V150, Q151, E153, P155, G157, P158, T160, T161, A162, H163, R164, T166 and R168 with reference to SEQ ID NO: 70 (residues 171, 172, 174, 176, 179, 181, 182, 183, 184, 185, 187 and 189 of the polypeptide of SEQ ID NO: 1).

In one aspect, provided is an anti-NKp46 antibody that has reduced binding to a NKp46 polypeptide having a mutation at one, two, three of more of (or all of) the residues selected from the group consisting of: D101, T102, T104, S106, H108, P109, P111, E112, I114, S115, G116, E117, K118, V150, Q151, E153, P155, G157, P158, T160, T161, A162, H163, R164, T166 and R168 with reference to SEQ ID NO: 70. In one aspect, provided is an anti-NKp46 antibody that has reduced binding to a NKp46 polypeptide having a mutation at one, two, three of more of (or all of) the residues selected from the group consisting of: D101, T102, T104, V150, Q151, E153, P155, G157, P158, T160, T161, A162, H163, R164, T166 and R168 with reference to SEQ ID NO: 70.

In another aspect, provided is an anti-NKp46 antibody that has reduced binding to a NKp46 polypeptide having a mutation at one, two, three of (or all of) more of the residues selected from the group consisting of: F180, P181, E183, P184 and K186, with reference to SEQ ID NO: 70 (residues 201, 202, 204, 205 and 207 of the polypeptide of SEQ ID NO: 1).

In another aspect, provided is an anti-NKp46 antibody that has reduced binding to a NKp46 polypeptide having a mutation at one, two, three of (or all of) more of the residues selected from the group consisting of: E137, G138, R139, S140, S141, H142, Q144, R145, Y147, G148, K149, V150 and Q151, with reference to SEQ ID NO: 70 (residues of the 158, 159, 160, 161, 162, 163, 165, 166, 168, 169, 170, 171 and 172 polypeptide of SEQ ID NO: 1).

Binding of anti-NKp46 antibody to cells transfected with the NKp46 mutants can be measured and compared to the ability of anti-NKp46 antibody to bind a wild-type NKp46 polypeptide (e.g., SEQ ID NO: 1, or SEQ ID NO: 70). A reduction in binding between an anti-NKp46 antibody and a mutant NKp46 polypeptide means that there is a reduction in binding affinity (e.g., as measured by known methods such FACS testing of cells expressing a particular mutant, or by Biacore testing of binding to mutant polypeptides) and/or a reduction in the total binding capacity of the anti-NKp46 antibody (e.g., as evidenced by a decrease in Bmax in a plot of anti-NKp46 antibody concentration versus polypeptide concentration). A significant reduction in binding indicates that the mutated residue is directly involved in binding to the anti-NKp46 antibody or is in close proximity to the binding protein when the anti-NKp46 antibody is bound to NKp46.

In some embodiments, a significant reduction in binding means that the binding affinity and/or capacity between an anti-NKp46 antibody and a mutant NKp46 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type NKp46 polypeptide. In certain embodiments, binding is reduced below detectable limits. In some embodiments, a significant reduction in binding is evidenced when binding of an anti-NKp46 antibody to a mutant NKp46 polypeptide is less than 50% (e.g., less than 45%, 40%, 35%, 30%, 25%, 20%, 15% or 10%) of the binding observed between the anti-NKp46 antibody and a wild-type NKp46 polypeptide.

In some embodiments, anti-NKp46 antibodies are provided that exhibit significantly lower binding for a mutant NKp46 polypeptide in which a residue in a segment comprising an amino acid residue bound by antibody 8B6A, 8B6B, 9H11A, 9H11B or 17E1 is substituted with a different amino acid.

Antibody CDR Sequences
Antibody 8B6A

The amino acid sequence of the heavy chain variable region of antibody 8B6A is listed as SEQ ID NO: 3, the amino acid sequence of the light chain variable region is listed as SEQ ID NO: 4. In a specific embodiment, provided is an antibody that binds essentially the same epitope or determinant as monoclonal antibody 8B6A; optionally the antibody comprises the hypervariable region of antibody 8B6A. In any of the embodiments herein, antibody 8B6A can be characterized by its amino acid sequence and/or nucleic acid sequence encoding it. In one preferred embodiment, the monoclonal antibody comprises the Fab or F(ab')$_2$ portion of 8B6A. Also provided is a monoclonal antibody that comprises the heavy chain variable region of 8B6A. According to one embodiment, the monoclonal antibody comprises the three CDRs of the heavy chain variable region of 8B6A. Also provided is a monoclonal antibody that further comprises the variable light chain variable region of 8B6A or one, two or three of the CDRs of the light chain variable region of 8B6A. Optionally any one or more of said light or heavy chain CDRs may contain one, two, three, four or five or more amino acid modifications (e.g., substitutions, insertions or deletions). Optionally, provided is an antibody where any of the light and/or heavy chain variable regions comprising part or all of an antigen binding region of antibody 8B6A are fused to an immunoglobulin constant region of the human IgG type, optionally a human constant region, optionally a human IgG1 or IgG3 isotype.

In another aspect, provided is an antibody, wherein the antibody comprises: a HCDR1 region of 8B6A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 8B6A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 8B6A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 8B6A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 8B6A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 8B6A comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1,2,3 and LCDR1,2,3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

Antibody 8B6B

The amino acid sequence of the heavy chain variable region of antibody 8B6B is listed as SEQ ID NO: 3, the amino acid sequence of the light chain variable region is listed as SEQ ID NO: 21. Antibodies 8B6B and 8B6A share the same heavy chain but are associated with different light chains. In a specific embodiment, provided is an antibody that binds essentially the same epitope or determinant as monoclonal antibody 8B6B; optionally the antibody comprises the hypervariable region of antibody 8B6B. In any of the embodiments herein, antibody 8B6B can be characterized by its amino acid sequence and/or nucleic acid sequence encoding it. In one preferred embodiment, the monoclonal antibody comprises the Fab or F(ab')$_2$ portion of 8B6B. Also provided is a monoclonal antibody that comprises the heavy chain variable region of 8B6B. According to one embodiment, the monoclonal antibody comprises the three CDRs of the heavy chain variable region of 8B6B. Also provided is a monoclonal antibody that further comprises the variable light chain variable region of 8B6B or one, two or three of the CDRs of the light chain variable region of 8B6B. Optionally any one or more of said light or heavy chain CDRs may contain one, two, three, four or five or more amino acid modifications (e.g., substitutions, insertions or deletions). Optionally, provided is an antibody where any of the light and/or heavy chain variable regions comprising part or all of an antigen binding region of antibody 8B6B are fused to an immunoglobulin constant region of the human IgG type, optionally a human constant region, optionally a human IgG1 or IgG3 isotype.

In another aspect, provided is an antibody, wherein the antibody comprises: a HCDR1 region of 8B6B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 8B6B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 8B6B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 8B6B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 8B6B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 8B6B comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1,2,3 and LCDR1,2,3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

Antibody 9H11A

The amino acid sequence of the heavy chain variable region of antibody 9H11A is listed as SEQ ID NO: 29, the amino acid sequence of the light chain variable region is listed as SEQ ID NO: 30. In a specific embodiment, provided is an antibody that binds essentially the same epitope or determinant as monoclonal antibodies 9H11A; optionally the antibody comprises the hypervariable region of antibody 9H11A. In any of the embodiments herein, antibody 9H11A can be characterized by its amino acid sequence and/or nucleic acid sequence encoding it. In one preferred embodiment, the monoclonal antibody comprises the Fab or F(ab')$_2$ portion of 9H11A. Also provided is a monoclonal antibody that comprises the heavy chain variable region of 9H11A. According to one embodiment, the monoclonal antibody comprises the three CDRs of the heavy chain variable region of 9H11A. Also provided is a monoclonal antibody that further comprises the variable light chain variable region of 9H11A or one, two or three of the CDRs of the light chain variable region of 9H11A. Optionally any one or more of said light or heavy chain CDRs may contain one, two, three, four or five or more amino acid modifications (e.g., substitutions, insertions or deletions). Optionally, provided is an antibody where any of the light and/or heavy chain variable regions comprising part or all of an antigen binding region of antibody 9H11A are fused to an immunoglobulin constant region of the human IgG type, optionally a human constant region, optionally a human IgG1 or IgG3 isotype.

In another aspect, provided is an antibody, wherein the antibody comprises: a HCDR1 region of 9H11A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 9H11A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 9H11A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 9H11A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 9H11A comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 9H11A comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1,2,3 and LCDR1,2,3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

Antibody 9H11B

The amino acid sequence of the heavy chain variable region of antibody 9H11B is listed as SEQ ID NO: 29, the amino acid sequence of the light chain variable region is listed as SEQ ID NO: 47. Antibodies 9H11B and 9H11A share the same heavy chain but are associated with different light chains. In a specific embodiment, provided is an antibody that binds essentially the same epitope or determinant as monoclonal antibodies 9H11B; optionally the antibody comprises the hypervariable region of antibody 9H11B. In any of the embodiments herein, antibody 9H11B can be characterized by its amino acid sequence and/or nucleic acid sequence encoding it. In one preferred embodiment, the monoclonal antibody comprises the Fab or F(ab')$_2$ portion of 9H11B. Also provided is a monoclonal antibody that comprises the heavy chain variable region of 9H11B. According to one embodiment, the monoclonal antibody comprises the three CDRs of the heavy chain variable region of 9H11B. Also provided is a monoclonal antibody that further comprises the variable light chain variable region of 9H11B or one, two or three of the CDRs of the light chain variable region of 9H11B. Optionally any one or more of said light or heavy chain CDRs may contain one, two, three, four or five or more amino acid modifications (e.g., substitutions, insertions or deletions). Optionally, provided is an antibody where any of the light and/or heavy chain variable regions comprising part or all of an antigen binding region of antibody 9H11B are fused to an immunoglobulin constant region of the human IgG type, optionally a human constant region, optionally a human IgG1 or IgG3 isotype.

In another aspect, provided is an antibody, wherein the antibody comprises: a HCDR1 region of 9H11B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 9H11B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 9H11B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 9H11B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 9H11B comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 9H11B comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1,2,3 and LCDR1,2,3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

Antibody 17E1

The amino acid sequence of the heavy chain variable region of antibody 17E1 is listed as SEQ ID NO: 55, the amino acid sequence of the light chain variable region is listed as SEQ ID NO: 56. In a specific embodiment, provided is an antibody that binds essentially the same epitope or determinant as monoclonal antibodies 17E1; optionally the antibody comprises the hypervariable region of antibody 17E1. In any of the embodiments herein, antibody 17E1 can be characterized by its amino acid sequence and/or nucleic acid sequence encoding it. In one preferred embodiment, the monoclonal antibody comprises the Fab or F(ab')$_2$ portion of 17E1. Also provided is a monoclonal antibody that comprises the heavy chain variable region of 17E1. According to one embodiment, the monoclonal antibody comprises the three CDRs of the heavy chain variable region of 17E1. Also provided is a monoclonal antibody that further comprises the variable light chain variable region of 17E1 or one, two or three of the CDRs of the light chain variable region of 17E1. Optionally any one or more of said light or heavy chain CDRs may contain one, two, three, four or five or more amino acid modifications (e.g., substitutions, insertions or deletions). Optionally, provided is an antibody where any of the light and/or heavy chain variable regions comprising part or all of an antigen binding region of antibody 17E1 are fused to an immunoglobulin constant region of the human IgG type, optionally a human constant region, optionally a human IgG1 or IgG3 isotype.

In another aspect, provided is an antibody, wherein the antibody comprises: a HCDR1 region of 17E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 17E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 17E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 17E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 17E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 17E1 comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1,2,3 and LCDR1,2,3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

In another aspect of any of the embodiments herein, any of the heavy and light chain variable regions, and/or any of the CDRs 1, 2 and 3 of the heavy and light chains, of 8B6A, 8B6B, 9H11A, 9H11B or 17E1 may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular variable region(s), CDR or set of CDRs listed in the corresponding SEQ ID NO.

In any of the antibodies, e.g., 8B6A, 8B6B, 9H11A, 9H11B or 17E1, the specified variable region and CDR sequences may comprise sequence modifications, e.g., a substitution (1, 2, 3, 4, 5, 6, 7, 8 or more sequence modifications). In one embodiment, a CDRs 1, 2 and/or 3 of the heavy and light chains comprises one, two, three or more amino acid substitutions, where the residue substituted is a residue present in a sequence of human origin. In one embodiment the substitution is a conservative modification. A conservative sequence modification refers to an amino acid modification that does not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for retained function (i.e., the properties set forth herein) using the assays described herein.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

The sequences of the CDRs, according to AbM (Oxford Molecular's AbM antibody modelling software definition), Kabat and Chothia definitions systems, have been summarized in Table A below. The sequences of the variable regions of the antibodies according are listed in Table B below (if leader sequences are present any antibody chain can be specified to start at the amino acid position immediately following the end of the leader sequence), and each CDRs underlined. In any embodiment herein, a VL or VH sequence can be specified or numbered so as to contain or lack a signal peptide or any part thereof.

In one embodiment, the antibodies are of the human IgG1 or IgG3 isotype. In one embodiment, the antibodies are antibody fragments that retain their binding and/or functional properties.

TABLE A

| mAb | CDR definition | HCDR1 SEQ ID | Sequence | HCDR2 SEQ ID | Sequence | HCDR3 SEQ ID | Sequence |
|---|---|---|---|---|---|---|---|
| 8B6-A | Kabat | 5 | SYWMH | 8 | TIYPGSDI TNYDEKFK N | 11 | DGRFAN |
|  | Chotia | 6 | GYTFTSY | 9 | PGSD | 12 | GRFA |
|  | IMGT | 7 | GYTFTSY W | 10 | IYPGSDIT | 13 | TRDGRFAN |
| 8B6-B | Kabat | 5 | SYWMH | 8 | TIYPGSDI TNYDEKFK N | 11 | DGRFAN |
|  | Chotia | 6 | GYTFTSY | 9 | PGSD | 12 | GRFA |
|  | IMGT | 7 | GYTFTSY W | 10 | IYPGSDIT | 13 | TRDGRFAN |
| 9H11-A | Kabat | 31 | SYWMH | 34 | EIIPSNGV TNYNEKFK R | 37 | RLRYALDY |
|  | Chotia | 32 | GYTFTSY | 35 | PSNG | 38 | LRYALD |
|  | IMGT | 33 | GYTFTSY W | 36 | IIPSNGVT | 39 | TIRLRY- ALDY |
| 9H11-B | Kabat | 31 | SYWMH | 34 | EIIPSNGV TNYNEKFK R | 37 | RLRYALDY |
|  | Chotia | 32 | GYTFTSY | 35 | PSNG | 38 | LRYALD |
|  | IMGT | 33 | GYTFTSY W | 36 | IIPSNGVT | 39 | TIRLRY- ALDY |
| 17E1 | Kabat | 57 | SSWMH | 60 | HIHPNSGIS NYNEKFKG | 63 | GGRFDD |
|  | Chotia | 58 | GYTFTSS | 61 | PNSG | 64 | GRFD |
|  | IMGT | 59 | GYTFTSS W | 62 | IHPNSGIS | 65 | SRGGRFDD |

| mAb | CDR definition | LCDR1 SEQ ID | Sequence | LCDR2 SEQ ID | Sequence | LCDR3 SEQ ID | Sequence |
|---|---|---|---|---|---|---|---|
| 8B6-A | Kabat | 14 | SASSSVS YMH | 17 | EISKLAS | 19 | QQWNLPLT |
|  | Chotia | 15 | SSSVSY | | EIS | 20 | WNLPL |
|  | IMGT | 16 | SSVSY | | EIS | 19 | QQWNLPLT |
| 8B6-B | Kabat | 22 | RASQDIG SSL N | 25 | ATSSLDS | 27 | LQYASSPYT |
|  | Chotia | 23 | SQDIGSS | | ATS | 28 | YASSPY |
|  | IMGT | 24 | QDIGSS | | ATS | 27 | LQYASSPYT |
| 9H11-A | Kabat | 40 | RASQDIS NFL N | 43 | YTSRLHS | 45 | QQGNTLPPT |
|  | Chotia | 41 | SQDISNF | | YTS | 46 | GNTLPP |
|  | IMGT | 42 | QDISNF | | YTS | 45 | QQGNTLPPT |
| 9H11-B | Kabat | 48 | KASQNVG TNV A | 51 | STSFRYS | 53 | QQYN- SYPFT |
|  | Chotia | 49 | SQNVGTN | | STS | 54 | YNSYPF |
|  | IMGT | 50 | QNVGTN | | STS | 53 | QQYN- SYPFT |
| 17E1 | Kabat | 22 | RASQDIG SSL N | 66 | ATSRLDS | 67 | LQYASSPWT |
|  | Chotia | 23 | SQDIGSS | 26 | ATS | 68 | YASSPW |
|  | IMGT | 24 | QDIGSS | 26 | ATS | 67 | LQYASSPWT |

TABLE B

| Antibody portion | SEQ ID NO | Sequence |
|---|---|---|
| 8B6A VH | 3 | QVQLQQPGSELVRPGASVKLSCKAS GYTFTSYWMHWVKQRPGQGLEWIGT IYPGSDITNYDEKFKNKATLTVDTS SSTAYMQLSSLTSEDSAVYYCTRDG RFANWGQGTLVTVSA |
| 8B6A VK | 4 | EIVLTQSPAITAASLGQKVTITCSA SSSVSYMHWYQQKSGTSPKPWIYEI SKLASGVPARFSGSGSGTSYSLTIS SMEAEDAAIYYCQQWNLPLTFGAGT KLELK |
| 8B6B VH | 3 | QVQLQQPGSELVRPGASVKLSCKAS GYTFTSYWMHWVKQRPGQGLEWIGT |

TABLE B-continued

| Antibody portion | SEQ ID NO | Sequence |
|---|---|---|
| | | IYPGSDITNYDEKFKNKATLTVDTS SSTAYMQLSSLTSEDSAVYYCTRDG RFANWGQGTLVTVSA |
| 8B6B VK | 21 | EIQMTQSPSSLSASLGERVSLTCRA SQDIGSSLNWLQQEPDGTIKRLIYA TSSLDSGVPKRFSGSRSGSDYSLTI SSLESEDFVDYYCLQYASSPYTFGG GTKLEIK |
| 9H11A VH | 29 | QVQLQQPGAELVKPGASVKLSCKAS GYTFTSYWMHWVKLRPGQGFEWIGE IIPSNGVTNYNEKFKRKATLTVDKS SSTAYMQLSSLTSEDSAVYYCTIRL RYALDYWGQGTSVTVSA |
| 9H11A VK | 30 | DIQMTQTTSSLSASLGDRVTISCRA SQDISNFLNWYQQKPDGTVKLLIYY TSRLHSGVPSRFSGSGSGTDYSLTI SNLEQEDIATYFCQQGNTLPPTFGG GTKLEIK |
| 9H11B VH | 29 | QVQLQQPGAELVKPGASVKLSCKAS GYTFTSYWMHWVKLRPGQGFEWIGE IIPSNGVTNYNEKFKRKATLTVDKS SSTAYMQLSSLTSEDSAVYYCTIRL RYALDYWGQGTSVTVSA |
| 9H11B VK | 47 | DIVMTQSQKFMSTSVGDRVSVTCKA SQNVGTNVAWYQQKPGQSPKALIYS TSFRYSGVPDRFTGSGSGTDFTLTI SNVQSEDLAEYFCQQYNSYPFTFGS GTKLEIK |
| 17E1 VH | 55 | QVQLQQPGSVLVRPGASVKLSCKAS GYTFTSSWMHWAKQRPGQGLEWIGH IHPNSGISNYNEKFKGKATLTVDTS SSTAYVDLSSLTSEDSAVYYCSRGG RFDDWGAGTTVTVSS |
| 17E1 VK | 56 | DIQMTQSPSSLSASLGERVSLTCRA SQDIGSSLNWLQQEPDGTIKRLIYA TSRLDSGVPKRFSGSRSGSDYSLTI SSLESEDFVDYYCLQYASSPWTFGG GTKLEIK |

Fragments and Derivatives

Fragments and derivatives of antibodies (which are encompassed by the term "antibody" or "antibodies" as used in this application, unless otherwise stated or clearly contradicted by context), preferably a 8B6A, 8B6B, 9H11A, 9H11B or 17E1-like antibody, can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or a "dAb".

Fragments of the present antibodies can be obtained using standard methods. For instance, Fab or F (ab') 2 fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG).

Alternatively, the DNA of a hybridoma producing an antibody may be modified so as to encode a fragment. The modified DNA is then inserted into an expression vector and used to transform or transfect an appropriate cell, which then expresses the desired fragment.

In certain embodiments, the DNA of a hybridoma producing an antibody can be modified prior to insertion into an expression vector, for example, by substituting the coding sequence for human heavy- and light-chain constant domains in place of the homologous non-human sequences, or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

In one embodiment, the antibody is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for NKp46 receptors and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding. In a one example, the FRs of a humanized antibody chain are derived from a human variable region having at least about 60% overall sequence identity, and preferably at least about 80% overall sequence identity, with the variable region of the nonhuman donor (e.g., an 8B6A, 8B6B, 9H11A, 9H11B or 17E1 antibody). Optionally, the humanized heavy and/or light chain variable region shares at least about 60%, 70% or 80% overall sequence identity with the respective heavy and/or light chain variable region of the nonhuman donor (e.g., an 8B6A, 8B6B, 9H11A, 9H11B or 17E1 antibody).

Another method of making "humanized" monoclonal antibodies is to use a XenoMouse (Abgenix, Fremont, CA) as the mouse used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

The antibodies may also be derivatized to "chimeric" antibodies (immunoglobulins) in which a portion of the heavy/light chain(s) is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci. U.S.A, pp. 6851 (1984)).

Anti-NKp46 antibody molecules can be used to detect cells expressing NKp46, e.g., as anti-NKp46 immunoconjugates comprising an anti-NKp46 antibody conjugated to a detectable agent. Useful detectable agents with which an antibody or an antibody portion may be derivatized (or labeled) include fluorescent compounds, various enzymes, prosthetic groups, luminescent materials, bioluminescent materials, fluorescent emitting metal atoms, e.g., europium (Eu), and other anthanides, and radioactive materials (described above). Exemplary fluorescent detectable agents include fluorescein, fluorescein isothiocyanate, rhodamine, 5-dimethylamine-l-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin. Alternatively, the anti-NKp46 antibody may be associated with a second antibody that binds to the anti-NKp46 antibody, wherein the second antibody is derivatized with a detectable label; binding said second antibody into contact with the anti-NKp46 antibody, in vitro or in vivo, will allow the anti-NKp46 to serve as a labeled antibody.

Conjugation to a detectable moiety is useful, inter alia, when an antibody of the disclosure is used for diagnostic purposes. Such purposes include, but are not limited to, assaying biological samples, e.g., a blood sample or tissue biopsy, for the presence of NKp46-expressing cells, and detecting the presence, level, or activity of NKp46-expressing cells in an individual. Such assay and detection methods can be used in the diagnostic/therapeutic methods herein, e.g., involving detecting NKp46 expression in cells of a patient and if the patient's cells are determined to express NKp46, subsequently administering an NKp46 modulating antibody of the invention.

In certain embodiments, the present antibodies are used to purify NKp46-expressing cells from a biological sample. Biological samples can be obtained from a patient, e.g., for diagnostic or ex vivo therapeutic purposes, or from individuals or non-human primates to obtain a source of such cells for research purposes.

In one such embodiment, labeled antibodies can be used in FACS sorting to purify or isolate NKp46-expressing cells from a biological sample. Alternatively, in some embodiments conjugation of an antibody herein to a solid support can be useful as a tool for affinity purification of cells bearing an NKp46 receptor on their cell surface from a biological sample, such as a blood sample or cells from a tissue biopsy from an individual. This method of purification is another alternate embodiment, as is the resulting purified population of cells.

Regardless of the method used to isolate or purify the NKp46-expressing cells, the ability to do so is useful for numerous purposes, e.g., to diagnose an NKp46-associated disorder by assessing the number or activity of NKp46-expressing cells, e.g., prior to administration of anti-NKp46 antibodies as described herein. Further, purified NKp46-expressing cells are useful in a research context, e.g., to better characterize the cells and their various properties and behaviors, as well as to identify compounds or methods that can be used to modulate their behavior, activity, survival, or proliferation.

Antibody-Drug Conjugates

In some embodiments, the antibody molecule and non-antibody moiety are connected by means of a linker. In such embodiments, the immunoconjugate is represented by Formula (I):

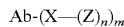　　　　　　　Formula (I)

wherein,

Ab is an anti-NKp46 antibody of the disclosure;

X is a moiety which connects Ab and Z, e.g., the residue of a linker following covalent linkage to one or both of Ab and Z;

Z is a therapeutic agent (e.g., any cytotoxic agent) or a label, or alternatively any other moiety which is to be delivered to a NKp46-expressing cell; and n is an integer selected from among 1 to 10, optionally 1, 2, 3 or 4 m is an integer selected from among 1 to 15.

The variable m represents the number of —X—Z moieties per antibody molecule in an immunoconjugate of formula (I). In various embodiments, m ranges from 1 to 15, 1 to 10, 1 to 9, 1 to 8, 1 to 7, 1 to 6, 1 to 5, 1 to 4, 1 to 3, 1 to 2. In some embodiments, m ranges from 2 to 10, 2 to 9, 2 to 8, 2 to 7, 2 to 6, 2 to 5, 2 to 4 or 2 to 3. In other embodiments, m is 1, 2, 3, 4, 5 or 6. In some compositions comprising a plurality of immunoconjugates of formula (I), m is the average number of —X—(Z)$_n$ moieties per Ab, also referred to as the average drug loading. Average drug loading may range from 1 to about 15 —X—(Z)$_n$ moieties per Ab. In some embodiments, when m represents the average drug loading, m is about 1, about 2, about 3, about 4, about 5, about 6, about 7, or about 8. In exemplary embodiments, m is from about 2 to about 8. In one embodiment, m is about 8. In another embodiment, m is about 4. In another embodiment, m is about 2. Optionally, n is 1.

The number of —X—Z moieties per Ab may be characterized by conventional means such as mass spectroscopy, ELISA assay, and HPLC. The quantitative distribution of immunoconjugates in terms of m may also be determined. In some instances, separation, purification, and characterization of homogeneous immunoconjugates where m is a certain value, as distinguished from immunoconjugates with other drug loadings, may be achieved by means such as reverse phase HPLC or electrophoresis.

The immunoconjugates of formula (I) may exist as mixtures, wherein each component of the mixture has a different m value. For example, an immunoconjugate of formula (I) may exist as a mixture comprising or consisting of two, three, four or more separate immunoconjugate components, comprising a first immunoconjugate component wherein m is 1, 2, 3, 4, 5, 6, 7 or 8 and a second immunoconjugate component wherein m is 1, 2, 3, 4, 5, 6, 7 or 8, and optionally a third, and/or fourth, and/or further immunoconjugates.

In some embodiments, e.g., as described in the Examples, the immunoconjugates of formula (I) exist as substantially homogenous compositions, wherein at least 80%, 90% or 95% of the immunoconjugates in a composition have the same m values (e.g., the same m value and the same n value); optionally n is 1 or 2 and m is 2 or 4.

A variety of suitable linkers (e.g., heterobifunctional reagents for connecting an antibody molecule to a therapeutic agent or label) and methods for preparing immunoconjugates are known in the art. (See, for example, Chari et al, Cancer Research 52: 127-131 (1992).) The linker can be cleavable, e.g., under physiological conditions., e.g., under intracellular conditions, such that cleavage of the linker releases the drug (therapeutic agent or label) in the intracellular environment. In other embodiments, the linker is not cleavable, and the drug is released, for example, by antibody degradation.

The linker can be bonded to a chemically reactive group on the antibody moiety, e.g., to a free amino, imino, hydroxyl, thiol or carboxyl group (e.g., to the N- or C-terminus, to the epsilon amino group of one or more lysine residues, the free carboxylic acid group of one or more glutamic acid or aspartic acid residues, or to the sulfhydryl group of one or more cysteinyl residues). The site to which the linker is bound can be a natural residue in the amino acid sequence of the antibody moiety or it can be introduced into the antibody moiety, e.g., by DNA recombinant technology (e.g., by introducing a cysteine or protease cleavage site in the amino acid sequence) or by protein biochemistry (e.g., reduction, pH adjustment or proteolysis).

One of the most commonly used non-specific methods of covalent attachment is the carbodiimide reaction to link a carboxy (or amino) group of a compound to amino (or carboxy) groups of the antibody molecule. Additionally, bifunctional agents such as dialdehydes or imidoesters have been used to link the amino group of a compound to amino groups of an antibody molecule. Also available for attachment of drugs to antibody molecules is the Schiff base reaction. This method involves the periodate oxidation of a drug that contains glycol or hydroxy groups, thus forming an aldehyde which is then reacted with the antibody molecule. Attachment occurs via formation of a Schiff base with amino groups of the antibody molecule. Isothiocyanates can also be used as coupling agents for covalently attaching drugs to antibody molecule. Other techniques are known to the skilled artisan.

In certain embodiments, an intermediate, which is the precursor of the linker (X), is reacted with the drug (Z) under appropriate conditions. In certain embodiments, reactive groups are used on the drug and/or the intermediate. The product of the reaction between the drug and the intermediate, or the derivatized drug, is subsequently reacted with the antibody molecule under appropriate conditions.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells. Most typical are peptidyl linkers that are cleavable by enzymes that are present in cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene).

In yet other specific embodiments, the linker is a malonate linker (Johnson et al, 1995, Anticancer Res. 15: 1387-93), a maleimidobenzoyl linker (Lau et al., 1995, BioorgMed Chem. 3(10): 1299-1304), or a 3'-N-amide analog (Lau et al, 1995, Bioorg. Med. Chem. 3(10):1305-12).

In yet other embodiments, the linker unit is not cleavable and the drug is released by antibody degradation. (See for example U.S. Publication No. 20050238649 incorporated by reference herein in its entirety and for all purposes).

In one embodiment, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, in a sample of immunoconjugate, are cleaved when the immunoconjugate presents in an extracellular environment (e.g., in plasma). Whether a linker is not substantially sensitive to the extracellular environment can be determined, for example, by incubating with plasma the immunoconjugate for a predetermined time period (e.g., 2, 4, 8, 16, or 24 hours) and then quantitating the amount of free drug present in the plasma.

In other embodiments, a linker can function as a spacer to distance an antibody from an agent in order to avoid interference with binding capabilities. In one embodiment, a linker may comprise a stretcher unit, e.g., a molecule that forms a bond with a sulfur atom, a primary or secondary amino group or a carbohydrate group of the antibody, and which stretcher links the antibody to the therapeutic agent or label (Z) or to an amino acid unit which is in turn linked to Z. When the stretcher is linked to an amino acid unit, the amino acid unit can be directly linked to Z or can comprise a spacer element (e.g., a non-self immolative or a self immolative spacer) linking the amino acid unit and Z. The amino acid unit can be a single amino acid or a peptide, e.g., valine-citrulline or phenyalanine-lysine.

In certain embodiments, enzyme catalyzed methods are used to conjugate a cytotoxic agent to an amino acid residue of the antibody.

Advantageously, a transglutaminase (TGase) enzyme is employed to catalyze the stoichiometrically functionalization of acceptor glutamines on antibodies with a cytotoxic agent. For example, TGase-catalyzed methods can be used to functionalize antibodies with large and/or hydrophobic substrates (for example pyrrolobenzodiazepine dimers which represent highly hydrophobic organic molecules). In another example, a sortase enzyme is employed to catalyze the functionalization of acceptor amino acid residues on antibodies, e.g., within a sortase recognition peptide tag engineered within or appended to a constant region of the antibody. Coupling of cytotoxic moieties to acceptor glutamines on antibody constant regions using TGase-catalyzed methods, and linkers suitable therefore, are described in PCT publication nos. WO2013/309283 and WO2014/202775 (Innate Pharma), the disclosures of which are incorporated herein by reference. Enzymes of the TG-family catalyze covalent protein crosslinking by forming proteinase resistant isopeptide bonds between a lysine donor residue of one protein and an acceptor glutamine residue of another protein, and is accompanied by the release of ammonia. The catalytic mechanism of transglutaminases has been proposed as follows. After the Glycine-containing first substrate (an acceptor glutamine) binds to the enzyme, it forms a γ-glutamylthioester with the cysteine residue in the active center of TGase, known as the acylenzyme intermediate, accompanied by the release of ammonia. The second substrate (donor or K-substrate) then binds to the acylenzyme intermediate and attacks the thioester bond. The product (two proteins crosslinked by an Nε(γ-glutamyl)lysine isopetide bridge) is formed and released. This re-establishes the active-centre Cys residue of the enzyme in its original form and allows it to participate in another cycle of catalysis. The formation of the covalent acylenzyme intermediate is thought to be the rate-limiting step in these reactions. The catalytic triad of many transglutaminases is papain-like, containing Cys-His-Asp (where His is histidine and Asp is aspartic acid) and, crucially, a tryptophan (Trp) residue located 36 residues away from the active-centre Cys. In contrast, bacterial TG isolated from *Streptoverticillium* sp (vide supra) has an atypical catalytic triad and shows no sequence homology with the papain-like catalytic triad of other TGases.

TGases display strict specificity in recognition of glutamine protein substrates. However, TGases display broad specificity for recognition of the acyl-acceptor amine group, which can either be the ε-amino group of peptidyl lysine or a low-molecular mass primary amine (frequently a polyamine) (see, e.g., Folk, et al. (1980) J. Biol. Chem. 255, 3695-3700). Thus a wide range of lysine-based linkers can be envisaged. For example, in addition to lysine, the small lysine-mimicking primary amine 5-pentylamine (cadaverin) and variants or fragments thereof can efficiently bind to the acylenzyme intermediate, and a pseudo-isopeptide bond with the glutamine-containing protein is formed. See, e.g., Lorand, L. et al. (1979) Biochemistry 18, 1756-1765 (1979); Murthy, S. N. et al. (1994). J. Biol. Chem. 269, 22907-22911 (1994); Murthy, P. et al. (2009) Biochemistry (2009).

Bacterial, archaeal and eukaryotic TGases have been characterized and differ in several ways from mammalian TGases (Lorand, L. & Graham, R. M. (2003) Nat. Rev. Mol. Cell Biol. 4, 140-156). BTG and more generally microbial TGases (EC 2.3.2.13, protein-glutamine-γ-glutamyltransferase) such as *Streptomyces mobaraensis* are calcium-independent and have an amino acid sequence of) very different from those of mammalian TGs (Ando et al. (1989) Agric. Biol. Chem. 53, 2613-2617). BTG is furthermore much smaller (37.8 kDa versus 76.6 kDa for guinea pig liver TG). Additionally, BTG shows broader substrate specificity for the amine acceptor glutamine substrates in proteins than do mammalian TGases. These characteristics, together with a higher reaction rate, low cost of production, and a decreased tendency to catalyze deamidation make BTG a preferred enzyme for use herein.

Antibodies can be conjugated to an acceptor glutamine introduced to an antibody at a suitable position. For example, a glutamine recognition tag comprising one or the number of desired acceptor glutamines can be chosen from among a range of peptide sequences and fused to the C-terminus of the antibody heavy and/or light chains.

If the acceptor glutamine is the glutamine residue naturally present at residue Q295 (Kabat EU numbering) and/or at nearby residues such as residue N297 The antibodies that are to be conjugated to the lysine-based linker will typically be free of N-linked glycosylation at residue N297 (Kabat EU numbering). Full-length wild-type IgG antibodies naturally comprise N-linked glycosylation at residue 297 of the heavy chain which interferes and prevents with TGase-mediated conjugation onto glutamine residue Q295 naturally present in the CH2 domain. Consequently, antibodies may be prepared such that they lack N297-linked glycosylation. Enzymatic deglycosylation can be carried out as described herein or according to any suitable method. For example, antibody (1 mg) in PBS buffer (0.1 mol/L NaCl and 0.05 mol/L sodium phosphate buffer, pH 7.4) are incubated with 100 units (0.2 μL) of N-glycosidase F (PNGase F) from *Flavobacterium meningosepticum* (New England BioLabs, Ipswich, UK) at 37° C. overnight. The enzyme is then removed by centrifugation-dialysis (Vivaspin MWCO 50 kDa, Vivascience, Winkel, Switzerland). The product can be analyzed by LC/MS. Alternatively, antibody Fc domains can be engineered to introduce an amino acid substation that prevents N-linked glycosylation. For example a N297X substitution can be introduced into a heavy chain of an antibody, wherein X is any amino acid other than asparagine. When X is a glutamine residue, the glutamine at residue 297 will serve as an acceptor glutamine and will be coupled to a linker by TGase.

Antibodies can be engineered to have the desired number of acceptor glutamines. In one example, an antibody comprises a single acceptor glutamine at residue 295 of each heavy chain (e.g., the antibody comprises a N297X substitution, where X is any amino acid other than asparagine or glutamine, or the antibody is enzymatically deglycosylated); the antibody will have a total of two acceptor glutamines. In one example, an antibody comprises a single acceptor glutamine at residue 297 of each heavy chain (e.g., the antibody comprises a Q295X substitution, where X is any amino acid other than glutamine, and a N297Q substitution); the antibody will have a total of two acceptor glutamines. In one example, an antibody comprises an acceptor glutamine at residues 295 and 297 of each heavy chain (e.g., the antibody comprises a N295Q substitution); the antibody will have a total of four acceptor glutamines. In one example, an antibody comprises one or more acceptor glutamines within a TGase recognition tag fused, optionally via intervening amino acid residues, to a C-terminus of a light and/or heavy chain.

In one embodiment, the product is analyzed for drug loading (e.g., number of conjugates per antibody. Such methods can be used to determine the mean number of conjugates per antibody (e.g., the mean DAR) as well as the distribution of number of conjugates per antibody in a composition, i.e., the percentage of total antibody with any given level of drug loading or DAR. The portion of antibodies having a number (n) of conjugated acceptor glutamines (e.g., n=1, 2, 3, 4, 5, 6, etc.) can be determined. One technique adapted to such determination and more generally drug loading is hydrophobic interaction chromatography (HIC), HIC can be carried out as described for example in Hamblett et al. (2004) Cancer Res. 10: 7063-7070; Wakankar et al. (2011) mAbs 3(2): 161-172; and Lyon et al (2012) Methods in Enzymology, Vol. 502: 123-138, the disclosure of which are incorporated herein by reference.

Examples of useful TGases include microbial transglutaminases, such as e.g., from *Streptomyces* mobaraense, *Streptomyces* cinnamoneum and *Streptomyces* griseocarneum (for discussion of suitable TGases, see, e.g., PCT publication nos. WO2013/309283 and WO2014/202775). A preferred TGase is bacterial transglutaminase (BTG) (see, e.g., EC 2.3.2.13, protein-glutamine-γ-glutamyltransferase). In a more preferred embodiment, the TGase is from *S. mobaraensis*. In another embodiment, the TGase is a mutant TGase having at least 80% sequence homology with native TGase. A preferred example is recombinant bacterial transglutaminase derived from *streptomyces mobaraensis* (available from Zedira, Darmstadt, Germany).

The TGase-catalyzed reaction can be carried out under mild conditions, from several hours to a day (e.g., overnight). Recombinant BTG (EC 2.3.2.13) from *streptomyces mobaraensis* (Zedira, Darmstadt, Germany) can be used at a concentration of between 1 and 20 U/mL, preferably between 6 U/mL and 20 U/mL. The lysine-based linker substrates are reacted with antibody (1 mg/mL) at ligand concentrations between 400 and 600 mol/L, providing a 60 to 90-fold excess of the substrates over the antibody, or optionally at lower excess of substrates, e.g., 1- to 20-fold, or 10-20 fold. The reactions are performed in potassium-free phosphate buffered saline (PBS; pH 8) at 37° C. After 4 h to several days (depending on the antibody and the ligand), steady-state conditions are achieved. Excess ligand and enzyme are then removed using centrifugation-dialysis (Vivaspin MWCO 50 kDa, Vivascience, Winkel, Switzerland). Reactions are monitored by LC/MS. Higher amounts of TGase can be used as a function of different lysine-derivatives and substrates.

An acceptor glutamine present on an antibody (e.g., part of the antibody's primary structure, including for example an antibody or antibody fragment with a peptide tag) will, under suitable conditions, be recognized by a TGase and covalently bound to a lysine-based linker. Resulting antibody conjugates can be analyzed using any suitable method. Preferably, the stoichiometry of the conjugated antibodies can be characterized by liquid chromatography mass spectrometry (LC/MS) using a top-down approach in order to assess the number of lysine-based linker and/or where applicable moieties-of-interest conjugated to antibodies, and in particular the homogeneity of the composition. Conjugates can be reduced before LC/MS analysis and light chains and heavy chains are measured separately.

In one aspect, provided is a method for conjugating a moiety of interest (Z) to an antibody, comprising the steps of:
  a) providing an antibody of the disclosure, wherein the antibody comprises at least one acceptor glutamine residue in or appended to a heavy and/or light chain constant region; and
  b) reacting said antibody with a linker comprising a primary amine (a lysine-based linker) comprising a moiety of interest (Z), in the presence of a TGase, under conditions sufficient to obtain an antibody comprising an acceptor glutamine linked (covalently) to a moiety of interest (Z) via said linker.

Certain aspects of the disclosure are directed to a linking reagent that can be attached, by the action of a TGase, to a polypeptide at a glutamine residue (Q) within the sequence of the antibody (Ab). The linking reagent comprises a lysine derivative (Lys) or a functional equivalent thereof, that is connected to at least one reactive group (R) or a moiety-of-interest (Z). The lysine derivative (Lys) or a functional equivalent can comprise generally any primary amine chain which is a substrate for TGase, e.g., comprising an alkylamine, oxoamine. In one embodiment, a plurality of reactive groups, preferably non-complementary reactive groups, can be attached to the linking reagent. The reactive group is preferably a functionality that is insensitive to water but selectively undergoes a very high conversion addition reaction with a complementary reagent. The functional equivalent of a lysine derivative may comprise a 2 to 20 carbon chain, or a functional equivalent thereof, with an $H_2N$ or $H_2NCH_2$ (aminomethylene) group, or a protected $H_2N$ or $H_2NCH_2$ group that can be derived from the $H_2N$ or aminomethylene positioned at one or more ends of the carbon chain. The functional equivalent of the carbon chain may comprise a chain of 3 to 20 atoms where one or more of the atoms other than the primary amine can be other than carbon, for example oxygen, sulfur, nitrogen, or other atoms, e.g., with an $H_2NOCH_2$ group, or a protected $H_2NOCH_2$ group positioned at one or more ends of the carbon chain. The oxygen, sulfur, or nitrogen atom can be of an ether, ester, thioether, thioester, amino, alkylamino, amido or alkylamido functionality within the carbon chain. Suitable linkers are described, for example, in PCT publication nos. WO2013/309283 and WO2014/202775.

One exemplary functional equivalent of the carbon chain is an oligo (ethylene oxide) chain. The functionality within the carbon chain can be included to couple the reactive group to the $H_2N$ $H_2NOCH_2$ or $H_2NCH_2$ group or protected $H_2N$, $H_2NOCH_2$ or $H_2NCH_2$ group. The carbon chain, or its functional equivalent, can be substituted or unsubstituted. For example, the carbon chain, or its functional equivalent can comprise a plurality of ($CH_2$— $CH_2$—O—) groups, optionally ($CH_2$— $CH_2$—O—)$_n$ group wherein n is an integer selected among the range of 1 to 6. The substituents can be alkyl groups, aryl groups, alkyl aryl groups, carboxylic acid groups, amide groups, hydroxy groups, or any other groups that do not compete with the amino group for, or inhibit, conjugation with a glutamine residue of the protein. Typically, when a substituent is present, its presence is in a convenient starting material, such as the carboxylic acid group of lysine, from which the lysine derivative results. The amine at the end of a carbon chain or functional equivalent is necessarily included in the linking reagent.

Examples of starting materials for the functional equivalent of lysine can be an α,ω-diaminoalkane, for example, 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, or 1,12-diaminododecane. Other starting materials for the functional equivalent of a lysine derivative can be α,ω-diamino oligo (ethylene oxide), for example, $H_2N(CH_2CH_2O)_x CH_2CH_2NH_2$ where x is an integer selected among the range of 1 to 6. The α,ω-diamino oligo (ethylene oxide) can be a single oligomer or it can be a mixture of oligomers where x defines an average size. An exemplary protected $H_2NCH_2$ is the tert-butylcarbamate protected amine of tert-butyl N-(5-aminopentyl)carbamate (N-Boc-cadaverin).

Linking reagents used for direct (one-step) linking of a moiety of interest (Z) to an antibody will advantageously comprise an element that functions as a spacer to distance a large, charged or hydrophobic organic moiety-of-interest (Z) from the acceptor glutamine. The spacer may be embodied in the lysine derivative or functional equivalent thereof, or in a further element of the linker (e.g., an L, V and/or Y group as further described herein). In one embodiment, the element that functions as a spacer is a lysine derivative (Lys) or a functional equivalent thereof having a structure NH—(C)—, wherein (C) is a substituted or unsubstituted alkyl or heteroalkyl chain, wherein any carbon of the chain is optionally substituted with an alkoxy, hydroxyl, alkylcarbonyloxy, alkyl-S—, thiol, alkyl-C(O)S—, amine, alkylamine, amide, or alkylamide, and where the chain length is an integer greater than 10 atoms, an integer from among the range of 10 to 20. For example, C can be a carbon comprising framework of 10 to 20 atoms substituted at one or more atoms. In one embodiment, the linking reagent comprises an L, V and/or Y group that functions as a spacer and is positioned between the NH—(C)— group and the moiety-of-interest (Z), wherein L is a carbon-comprising framework of 1 to 200 atoms substituted at one or more atoms, optionally wherein the carbon comprising framework is a linear hydrocarbon, a symmetrically or asymmetrically branched hydrocarbon, monosaccharide, a glycan, disaccharide, linear or branched oligosaccharide (asymmetrically branched or symmetrically branched), other natural linear or branched oligomers (asymmetrically branched or symmetrically branched), amino acid residue, di-, tri- or oligopeptide, or any dimer, trimer, or higher oligomer (linear, asymmetrically branched or symmetrically branched) for example resulting from any chain-growth or step-growth polymerization process; V is a non-cleavable moiety or a conditionally-cleavable moiety, optionally following prior conditional transformation, which can be cleaved or transformed by a chemical, photochemical, physical, biological, or enzymatic process (e.g., cleavage of V ultimately leading to release of one or more moieties subsequently or ultimately linked to V, for example a Z moiety). In some embodiments, V is, preferably, a di-, tri-, tetra-, or oligopeptide (e.g., a valine-citrulline containing peptide, or the like) and Y is a spacer system (e.g., a self-eliminating spacer system or a non-self-elimination spacer system) which is comprised of 1 or more spacers. The spacer system Y may self-eliminating or non-self-eliminating. A "self-eliminating" spacer unit allows for release of the drug moiety without a separate hydrolysis step. When a self-eliminating spacer is used, after cleavage or transformation of V, the side of Y linked to V becomes unblocked, which results in eventual release of one or more moieties Z. Y may for example be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O— $C_{1-5}$ alkyl, —O— $C_{5-10}$ alkyl, —O— $C_{11-20}$ alkyl, or $(CH_2-CH_2-O-)_{1-24}$, or $(CH_2)_{x1}-(CH_2-O-CH_2)_{1-24}-(CH_2)_{x2}-$ group, wherein x1 and x2 are independently an integer selected among the range of 0 to 20, an amino acid, an oligopeptide, glycan, sulfate, phosphate, or carboxylate. Optionally, Y is absent. In some embodiments, Y is a $C_{2-6}$ alkyl group. The self-elimination spacer systems may for example be those described in WO 02/083180 and WO 2004/043493, which are incorporated herein by reference in their entirety, as well as other self-elimination spacers known to a person skilled in the art. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the spacer unit is p-aminobenzyloxycarbonyl (PAB). Examples of self-eliminating spacer units further include, but are not limited to, aromatic compounds that are electronically similar to p-aminobenzyl alcohol (see, e.g., US 2005/0256030 A1), such as 2-aminoimidazol-5-methanoi derivatives (Hay et al. (1999) Bioorg. Med. Chem. Lett. 9:2237) and ortho- or para-aminobenzylacetals. Spacers can be used mat undergo cyclization upon amide bond hydrolysis, such as substituted and unsubstituted 4-aminobutyric acid amides (Rodrigues et al. Chemistry Biology, 1995, 2, 223) and 2-aminophenylpropionic acid amides (Amsberry, et al., J. Org. Chem., 1990, 55. 5867). Elimination of amine-containing drugs that are substituted at the a-position of glycine (Kingsbury, et al., J. Med. Chem., 1984, 27, 1447) are also examples of self-immolative spacers.

V may comprise for example a carbon comprising framework of 1 to 200 atoms, optionally a carbon comprising framework of at least 10 atoms, e.g., 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), an amino acid, a di-, tri-, tetra-, or oligopeptide, or more generally any dimer, trimer, or higher oligomer (linear, asymmetrically branched or symmetrically branched) resulting from any chain-growth or step-growth polymerization process. V may for example be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O— $C_{1-5}$ alkyl, —O— $C_{5-10}$ alkyl, —O— $C_{11-20}$ alkyl, or $(CH_2-CH_2-O-)_{1-24}$, or $(CH_2)_{x1}-(CH_2-O-CH_2)_{1-24}-(CH_2)_{x2}-$ group, wherein x1 and x2 are independently an integer selected among the range of 0 to 20, an amino acid, an oligopeptide, glycan, sulfate, phosphate, or carboxylate. Optionally, V may be or absent. In some embodiments, V is a $C_{2-6}$ alkyl group.

In certain embodiment, V contains a di-, tri-, tetra-, or oligopeptide which consists of an amino acid sequence recognized by a protease. The tripeptide may be linked via its C-terminus to Y. In one embodiment, the C-terminal amino acid residue of the tripeptide is selected from arginine, citrulline, and lysine, the middle amino acid residue of the tripeptide is selected from alanine, valine, leucine, isoleucine, methionine, phenylalanine, cyclohexylglycine, tryptophan and proline, and the N-terminal ammo acid residue of the tripeptide is selected from any natural or unnatural amino acid. In one embodiment the disclosure provides to a compound wherein V comprises a dipeptide. The dipeptide may be linked via its C-terminus to Y. In one embodiment, the C-terminal amino acid residue of the dipeptide is selected from alanine, arginine, citrulline, and lysine, and the N-terminal amino acid residue of the dipeptide is selected from any natural or unnatural amino acid. In one embodiment, V is selected from phenylalanine-lysine and valine-citrulline.

In one embodiment provided is an antibody or antibody fragment comprising a functionalized acceptor glutamine residue, the functionalized acceptor glutamine residue having Formula II,

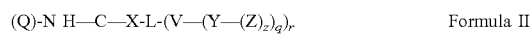

or a pharmaceutically acceptable salt or solvate thereof, wherein:

Q is a glutamine residue present in an antibody or antibody fragment;

C is a substituted or unsubstituted alkyl or heteroalkyl chain, optionally wherein any carbon of the chain is substituted with an alkoxy, hydroxyl, alkylcarbonyloxy, alkyl-S—, thiol, alkyl-C(O)S—, amine, alkylamine, amide, or alkylamide;

X is NH, O, S, absent, or a bond;

L is independently absent, a bond or a continuation of a bond, or a carbon comprising framework of 5 to 200 atoms substituted at one or more atoms, optionally, wherein the carbon comprising framework comprises a linear framework of 5 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

r is an integer selected from among 1, 2, 3 or 4;

q is an integer selected from among 1, 2, 3 or 4;

z is an integer selected from among 1, 2, 3 or 4; and

V is independently absent, a non-cleavable moiety or a conditionally-cleavable moiety;

Y is independently absent, a bond or a continuation of a bond, or a spacer system which is comprised of 1 or more spacers; and Z is a cytotoxic agent.

In some embodiments, particularly when highly hydrophobic drugs are conjugated to antibodies, organic solvent is generally required to maintain solubility and avoid formation of aggregated antibody-drug conjugates. Where a hydrophobic linker substrate cannot be solubilized without high concentrations of organic solvent (e.g., linkers comprising pyrrolobenzodiazepine moieties require as much as 50% solvent to permit highly homogenous coupling at a DAR of 2), a multi-step coupling process making use of a linker with a reactive moiety can be used to achieve highly homogenous compositions. Organic solvent at 5% or higher, however, inhibits the ability of TGase to conjugate efficiently, resulting in incomplete coupling (less than 90% or acceptor glutamines functionalized) when the linker with reactive moiety is coupled to an antibody, e.g., at residue Q295 and/or at residue 297 when the antibody comprises a N297Q mutation. Consequently, the coupling can be carried out by reacting an antibody comprising an acceptor glutamine residue with a linking reagent with reactive moiety (R), in the presence of a transglutaminase enzyme, wherein solvent (e.g., organic solvent, polar solvent, non-polar solvent, DMSO) is absent or is present at less than 10% (v/v), optionally further less than 5%, 4%, 3% or 2% (v/v). The resulting antibody is then reacted with a linker comprising a complementary reactive group (R') and a hydrophobic drug (e.g., a pyrrolobenzodiazepine moiety) to yield an antibody coupled (e.g., via the reaction produce of R and R') to the hydrophobic drug (or other moiety of interest (Z)). The reaction step with linker comprising a complementary reactive group (R') and a hydrophobic drug can be carried out in the presence of solvent, e.g., wherein solvent (e.g., organic solvent, polar solvent, non-polar solvent, DMSO) is present in the reaction mixture, wherein solvent is present is present at more than 2%, 3%, 4%, 5%, 10%, 20%, 40% or 50% (v/v). See, e.g., Example 11 herein.

The R and complementary R' reactive groups can each be any suitable reactive moiety, for example a moiety comprising an unprotected or protected bioorthogonal-reaction compatible reactive group, for example an unprotected or protected thiol, epoxide, maleimide, haloacetamide, o-phoshenearomatic ester, azide, fulminate, sulfonate ester, alkyne, cyanide, amino-thiol, carbonyl, aldehyde, generally any group capable of oxime and hydrazine formation, 1,2,4,5-tetrazine, norbornene, other stained or otherwise electronically activated alkene, a substituted or unsubstituted cycloalkyne, generally any reactive groups which form via bioorthogonal cycloaddition reaction a 1,3- or 1,5-disubstituted triazole, any diene or strained alkene dienophile that can react via inverse electron demand Diels-Alder reaction, a protected or unprotected amine, a carboxylic acid, an aldehyde, or an oxyamine.

The reactive groups can for example chosen to undergo thio-maleimide (or haloacetamide) addition, Staudinger ligation, Huisgen 1,3-cycloaddition (click reaction), or Diels-Alder cycloaddition with a complementary reactive group attached to an agent comprising a therapeutic moiety, a diagnostic moiety, or any other moiety for a desired function. In one embodiment, the reactive group is a haloacetamide, (e.g., bromo-acetamide, iodo-acetamide, chloro-acetamide). Such reactive groups will be more stable in vivo (and in serum) compared with maleimide groups.

In one advantageous embodiment, the reactive groups R and R' are complementary reagents capable of undergoing a "click" reaction. For example a 1,3-dipole-functional compound can react with an alkyne in a cyclization reaction to form a heterocyclic compound, preferably in the substantial absence of added catalyst (e.g., Cu(I)). A variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups. Examples include o-phoshenearomatic ester, an azide, a fulminate, an alkyne (including any strained cycloalkyne), a cyanide, an anthracene, a tetrazine (e.g. 1,2,4,5-tetrazine), or a norbornene (or other strained cycloalkene). In one embodiment, one or R and R' is an azide and the other of R or R' is a strained cycloalkyne (e.g. a cyclooctyne). In one embodiment, one or R and R' is a tetrazine and the other of R or R' is a strained cycloalkene (e.g. a trans-cyclooctene).

In one aspect, present disclosure relates to a method for conjugating a moiety of interest (Z) (e.g., a hydrophobic, high molecular weight and/or charged organic compound) to an anti-NKp46 antibody of the disclosure, comprising the steps of:
a) providing an anti-NKp46 antibody of the disclosure comprising at least one acceptor glutamine residue; and
b) reacting said antibody with a linker comprising a primary amine (a lysine-based linker) comprising a reactive group (R), in the presence of a TGase, under conditions sufficient to obtain an antibody comprising an acceptor glutamine linked (covalently) to a reactive group (R) via said linker, wherein the reaction mixture is free of organic solvent or contains less than 10% (v/v) or contains less than 5%, 4%, 3% or 2% (v/v) organic solvent; and
c) reacting, optionally in the presence of organic solvent (e.g., at least 2%, 3%, 4%, 5%, 10%, 20%, 25%, 40% or 50% (v/v) organic solvent):
   (i) an antibody of step (b) comprising an acceptor glutamine linked to a reactive group (R) via the linker (the lysine-based linker), with
   (ii) a compound comprising a moiety of interest (Z) and a reactive group (R') capable of reacting with reactive group R,
under conditions sufficient to obtain an antibody comprising an acceptor glutamine linked to a moiety of interest (Z) (e.g., a cytotoxic agent) via a linker comprising a primary amine (a lysine-based linker). The resulting antibody can be characterized by the structure of formula III. In one embodiment provided is an antibody or antibody fragment comprising a functionalized acceptor glutamine residue, the functionalized acceptor glutamine residue having the structure of Formula III,

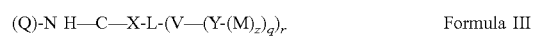

$$(Q)\text{-N H}—C—X\text{-L-}(V—(Y\text{-}(M)_z)_q)_r \quad \text{Formula III}$$

or a pharmaceutically acceptable salt or solvate thereof, wherein:
Q is a glutamine residue present in an antibody or antibody fragment;
C is a substituted or unsubstituted alkyl or heteroalkyl chain, optionally wherein any carbon of the chain is substituted with a alkoxy, hydroxyl, alkylcarbonyloxy, alkyl-S—, thiol, alkyl-C(O)S—, amine, alkylamine, amide, or alkylamide;
X is NH, O, S, absent, or a bond;
L is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;
r is an integer selected from among 1, 2, 3 or 4;
q is an integer selected from among 1, 2, 3 or 4;
z is an integer selected from among 1, 2, 3 or 4;

V is independently absent, a bond or a continuation of a bond, a non-cleavable moiety or a conditionally-cleavable moiety;

Y is independently absent, a bond or a continuation of a bond, or a spacer system which is comprised of 1 or more spacers;

M is independently: R or (RR')-L'-(V'—(Y'—(Z)$_{z'}$)$_{q'}$)$_{r'}$, wherein

R is a reactive moiety;

(RR') is an addition product between R and a complementary reactive moiety R';

L' is independently absent, a bond or a continuation of a bond, or a carbon comprising framework of 1 to 200 atoms substituted at one or more atoms, optionally, wherein the carbon comprising framework comprises a linear framework of 3 to 30 carbon atoms optionally substituted at one or more atoms, optionally wherein the carbon comprising framework is a linear hydrocarbon, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or a dimer, trimer, or higher oligomer (linear, asymmetrically branched or symmetrically branched) resulting from any chain-growth or step-growth polymerization process;

V' is independently absent, a bond or a continuation of a bond, a non-cleavable moiety or a conditionally-cleavable moiety;

Y' is independently absent, a bond or a continuation of a bond, or a spacer system which is comprised of 1 or more spacers;

Z is a cytotoxic agent, and each Z is directly coupled to either Y or V when Y is absent, or L when both Y and V are absent; and z', q' and r' are each independently an integer selected from among 1, 2, 3 or 4. In one embodiment, V is absent, a bond or a continuation of a bond and V' is a non-cleavable moiety or a conditionally-cleavable moiety. In one embodiment, Y is absent, a bond or a continuation of a bond and Y' is a spacer system which is comprised of 1 or more spacers.

The immunoconjugate can be purified from reactants by employing methodologies well known to those of skill in the art, e.g., column chromatography (e.g., affinity chromatography, ion exchange chromatography, gel filtration, hydrophobic interaction chromatography), dialysis, diafiltration or precipitation. The immunoconjugate can be evaluated by employing methodologies well known to those skilled in the art, e.g., SDS-PAGE, mass spectroscopy, or capillary electrophoresis.

The one or more moieties Z can be for example taxanes, anthracyclines, camptothecins, epothilones, mytomycins, combretastatins, vinca alkaloids, nitrogen mustards, maytansinoids, calicheamycins, duocarmycins, tubulysins, dolastatins and auristatins, enediynes, pyrrolobenzodiazepines, ethylenimines, radioisotopes, therapeutic proteins and peptides, and toxins or fragments thereof.

In one embodiment, Z is or comprises a DNA minor groove binding agent. In one embodiment, the Z moiety comprises a pyrrolobenzodiazepine (PBD). In one embodiment, Z is a pyrrolobenzodiazepine monomer. In one embodiment, Z is a pyrrolobenzodiazepine dimer comprising two pyrrolobenzodiazepine units. In one embodiment, Z is a pyrrolobenzodiazepine trimer comprising three pyrrolobenzodiazepine units. In one embodiment, Z is a pyrrolobenzodiazepine multimer comprising more than three pyrrolobenzodiazepine units. Structures of PBDs, as well as formulas and methods of producing them are described for example in PCT publications Nos: WO 2013/177481, WO 2011/130616, WO 2004/043880, WO 2005/085251, WO2012/112687 and WO 2011/023883, the disclosures of each of which are incorporated herein by reference.

The pyrrolo[2,1-c][1,4] benzodiazepines are a family of sequence-selective, minor-groove binding DNA-interactive agents that covalently attach to guanine residues. It has been reported that the (S)-chirality at the C11a-position of PBDs provides them with the appropriate 3-dimensional shape to fit perfectly into the DNA minor groove. PBDs can have different effects and modes of action. PBDs can be DNA-binders or DNA-alkylators that do not cause crosslinking of DNA, or PBDs can be DNA cross-linkers.

The pyrrolobenzodiazepine unit or monomer can have a general structure as follows:

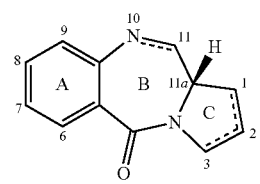

wherein the PBD can have different number, type and position of substituents, in both the aromatic A rings and pyrrolo C rings, and can vary in the degree of saturation of the C ring. In the B-ring there is either an imine (N=C), a carbinolamine (NH—CH(OH)), or a carbinolamine methyl ether (NH—CH(OMe)) at the $N^{10}$—$C^{11}$ position which is the electrophilic centre responsible for alkylating DNA.

The biological activity of PBDs can be potentiated by joining two PBD monomers or units together, typically through their C8/C8'-hydroxyl functionalities via a flexible alkylene linker.

In one aspect of the any of the embodiments herein, a pyrrolobenzodiazepine monomer or unit is a pyrrolo[2,1-c][1,4]benzodiazepine. In one aspect of the any of the embodiments herein, a pyrrolobenzodiazepine dimer is a C8/C8'-linked pyrrolo[2,1-c][1,4]benzodiazepine dimer.

A PBD can be attached to a linker through any suitable position. For example, the PBD can be connected to a linker (e.g., to a Y or to V, or, when absent, to L in a compound of Formula II; or to a Y' or to V', or, when absent, to L' in a compound of Formula III), via any of the positions in a PBD unit indicated below.

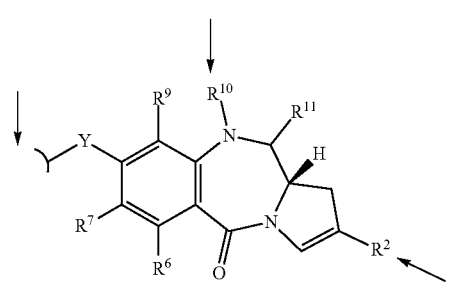

In one embodiment, a PBD dimer comprises the structure of the general formula below, with exemplary attachments points to other substituents or functionalities within a compound of Formula II or III indicated by arrows:

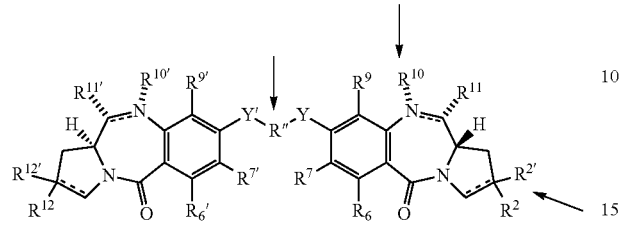

wherein:

$R^{12}$ and $R^{12'}$, and/or $R^2$ and $R^{2'}$ together respectively form a double bond =CH$_2$ or =CH—CH$_3$; or $R^{2'}$ and $R^{12'}$ are absent and $R^2$ and $R^{12}$ are independently selected from:

(iia) $O_{1-5}$ saturated aliphatic alkyl;

(iib) $O_{3-6}$ saturated cycloalkyl;

(iic)

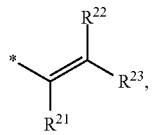

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(iid)

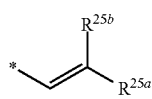

wherein one of $R^{25a}$ and $R^{25b}$ is H and the other is selected from: phenyl, which phenyl is optionally substituted by a group selected from halo, methyl, methoxy; pyridyl; and thiophenyl; and (iie)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

$R^6$ and $R^9$ are independently selected from H, R, OH, OR, SH, SR, NH$_2$, NHR, NRR', nitro, Me$_3$Sn and halo; where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, NH$_2$, NHR, NHRR', nitro, Me$_3$Sn and halo;

either:

(a) $R^{10}$ is H, and $R^{11}$ is OH, OR$^A$, where R$^A$ is alkyl;

(b) $R^{10}$ and $R^{11}$ form a nitrogen-carbon double bond between the nitrogen and carbon atoms to which they are bound; or (c) $R^{10}$ is H and $R^{11}$ is SO$_z$M, where z is 2 or 3 and M is a monovalent pharmaceutically acceptable cation;

R" is a $C_{3-12}$ alkylene group, which chain may be interrupted by one or more heteroatoms, e.g., O, S, NR$^{N2}$ (where R$^{N2}$ is H or $C_{1-4}$ alkyl), and/or aromatic rings, e.g., benzene or pyridine;

Y and Y' are selected from O, S, or NH; and $R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$, wherein if $R^{11}$ and $R^{11'}$ are SO$_z$M, M may represent a divalent pharmaceutically acceptable cation.

In another example, a PBD dimer comprises the structure of the general formula below:

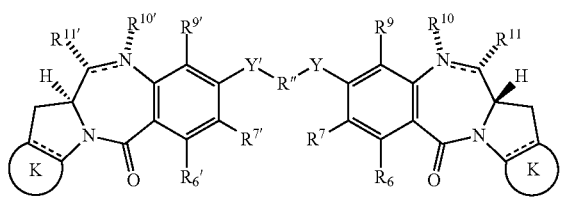

wherein $R^6$, $R^7$, $R^9$, $R^{6'}$, $R^{7'}$, $R^{9'}$, $R^{10}$, $R^{11}$, $R^{10'}$ and $R^{11'}$ are as defined above, and wherein the "K" ring is a substituted or unsubstituted aromatic or non-aromatic ring, optionally a 6-member ring, optionally a phenyl.

Examples of PBD dimers include:

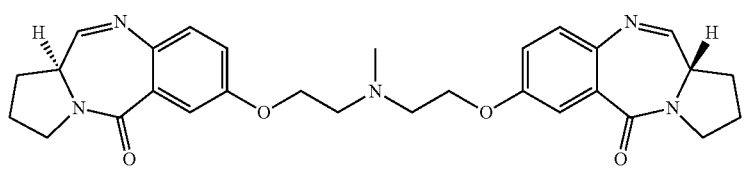

30

-continued

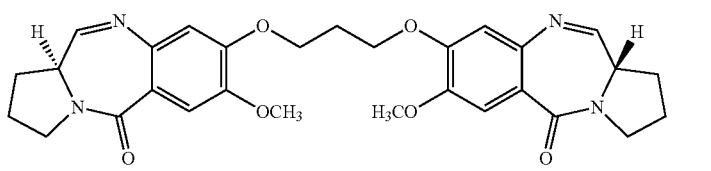

31

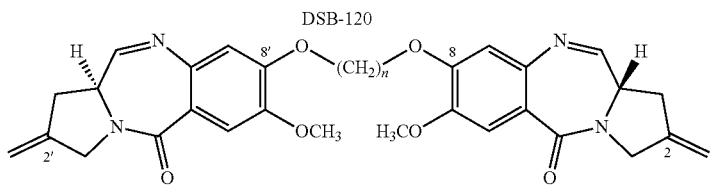

DSB-120

32 n = 3
33 n = 5

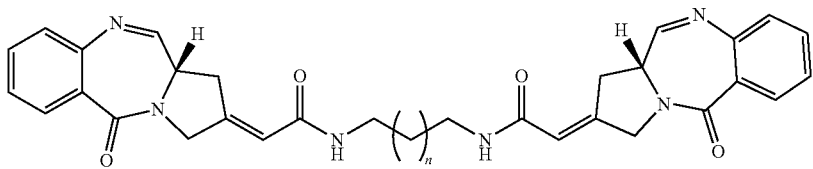

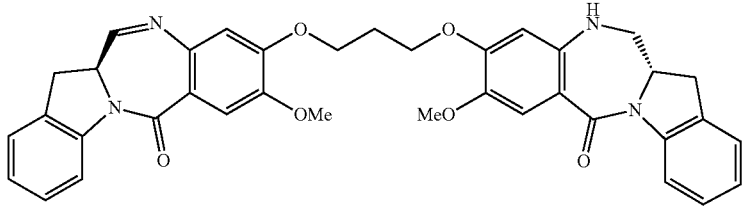

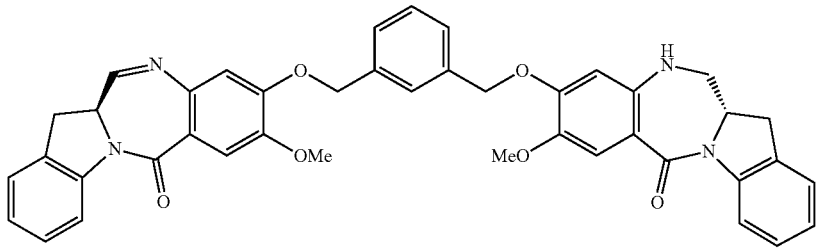

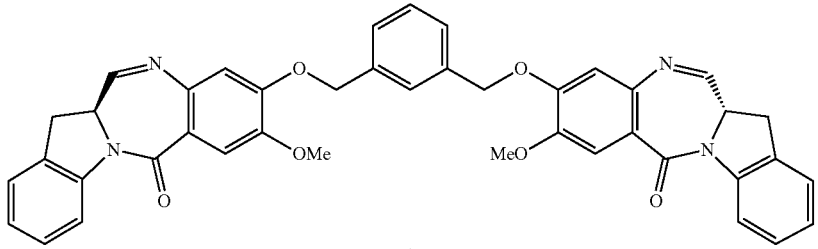

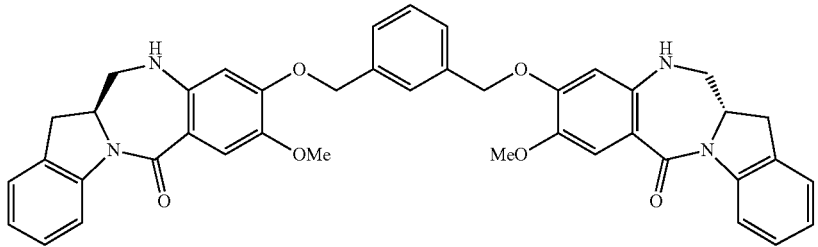

Constant Regions

In one aspect, in view of the ability of the anti-NKp46 antibodies to induce ADCC, the antibodies can comprise an Fc domain (or portion thereof) of human IgG1 or IgG3 isotype, for example a wild-type Fc domain, or optionally modified, that binds human CD16A, and optionally furthermore other human Fcγ receptors, thereby permitting the antibody to recruit immune effector cells and to mediate ADCC toward a NKp46-expressing malignant cell. When such an antibody is additionally conjugated to a cytotoxic agent, the antibody can eliminate NKp46-expressing target cell via (at least) two mechanisms of action: ADCC and direct cytotoxicity.

An example of an amino acid sequences (positions 230 to 447 sequence) of a human IgG1 Fc region (GenBank accession #: J00228) is shown as follows:

```
                                            (SEQ ID NO: 69)
      PAPELLGGPSVFLFPPKPKDTLMISRTPEVTCVVVD

VSHEDPEVKFNWYVDGVEVHNAKTKPREEQYNSTYR

VVSVLTVLHQDWLNGKEYKCKVSNKALPAPIEKTIS

KAKGQPREPQVYTLPPSRDELTKNQVSLTCLVKGFY

PSDIAVEWESNGQPENNYKTTPPVLDSDGSFFLYSK

LTVDKSRWQQGNVFSCSVMHEALHNHYTQKSLSLSP

GK.
```

In one aspect, as illustrated herein in the antibodies in the Examples using the anti-NKp46 antibodies immunoconjugates with stoichiometrically functionalized acceptor glutamines wherein substantially all antibodies in a mixture have a particular DAR (e.g., a DAR of 2 or 4), the antibodies are capable of potently inducing tumor cell death as immunoconjugates despite lacking Fc-mediated effector function. The antibodies of the disclosure can therefore comprise an Fc domain (or portion thereof) of human IgG1, IgG2, IgG3 or IgG4 isotype modified to reduce or abolish binding to one or more human Fcγ receptors (e.g., CD16A, CD16B, CD32A, CD32b, CD64). Such an antibody will avoid being taken up by non-tumoral Fcγ receptor-expressing cells. Consequently, when conjugated to a cytotoxic agent having high potency/toxicity (e.g., an agent that comprises a pyrrolobenzodiazepine moiety), the antibody is capable of being used at higher doses that would be possible otherwise, and may thus lead to greater efficacy in cancer treatment than an ADCC-mediating immunoconjugate. Optionally, as illustrated in the Examples herein, the antibody retains binding to human FcRn proteins thereby providing a vivo half-life.

In one embodiment, the antibody can comprise one or more specific mutations in the Fc region that result in "Fc silent" antibodies that have minimal interaction with effector cells. Silenced effector functions can be obtained by mutation in the Fc region of the antibodies and have been described in the art: N297X mutation, wherein X is any amino acid other than N, the LALA mutations (Strohl, W., 2009, Curr. Opin. Biotechnol., Vol. 20(6):685-691); and D265A (Baudino et al., 2008, J. Immunol. 181: 6664-69) see also Heusser et al., WO2012/065950, the disclosures of which are incorporated herein by reference. In one embodiment, an antibody comprises one, two, three or more amino acid substitutions in the hinge region. In one embodiment, the antibody is an IgG1 or IgG2 and comprises one, two or three substitutions at residues 233-236, optionally 233-238 (EU numbering). In one embodiment, the antibody is an IgG4 and comprises one, two or three substitutions at residues 327, 330 and/or 331 (EU numbering). Examples of silent Fc IgG1 antibodies are the LALA mutant comprising L234A and L235A mutation in the IgG1 Fc amino acid sequence. Another example of an Fc silent mutation is a mutation at residue D265, or at D265 and P329 for example as used in an IgG1 antibody as the DAPA (D265A, P329A) mutation (U.S. Pat. No. 6,737,056). Another silent IgG1 antibody comprises a mutation at residue N297 (e.g., N297A, N297S mutation), which results in aglycosylated/non-glycosylated antibodies.

Uses in Diagnostics and Therapy

In certain embodiments, the present antibodies are used to purify or identify NKp46 positive cells in a biological sample. Biological samples can be obtained from a patient, e.g., for diagnostic or ex vivo therapeutic purposes, or from individuals or non-human primates to obtain a source of such cells for research purposes.

NKp46 positive cells can be purified or identified using the present antibodies with any of a number of standard methods. For example, peripheral blood cells can be sorted using a FACS scanner using labeled antibodies specific for NKp46, and optionally to other cell surface molecules typically present on cells.

Regardless of the method used to isolate, purify or identify the NKp46 positive cells, the ability to do so is useful for numerous purposes, e.g., to diagnose a disorder characterized by a pathogenic expansion of NKp46-expressing cells, by assessing the number or activity or other characteristics of NKp46 positive cells obtained from a patient, or to evaluate the ability of the antibodies, or fragments or derivatives thereof, to modulate the activity or behavior of the cells of a patient prior, e.g., to one of the herein-described treatments using the antibodies. Further, purified NKp46 positive cells are useful in a research context, e.g., to better characterize the cells and their various properties and behaviors, as well as to identify compounds or methods that can be used to modulate their behavior, activity, or proliferation. The antibodies can also be useful in diagnostic methods, for example in methods of detecting NKp46 polypeptides on cells, e.g., disease cells from a patient.

Also provided is a pharmaceutical composition that comprises an antigen-binding agent (e.g., an antibody) of the disclosure which specifically binds to NKp46 polypeptides on the surface of cells. The antibody inhibits the growth or activity of the cells and/or leads to the elimination of the NKp46 positive cells. The composition further comprises a pharmaceutically acceptable carrier.

Further provided is a method of inhibiting the growth or activity of, and/or depleting, NKp46-positive cells, in a patient in need thereof, comprising the step of administering to said patient a composition according to the disclosure. Such treatment methods can be used for a number of disorders, including, but not limited to the treatment of cancers.

In one aspect, the methods of treatment of the disclosure comprise administering to an individual a composition comprising an antigen-binding compound that binds NKp46 in a therapeutically effective amount. A therapeutically effective amount may be for example an sufficient to cause an increase in the depletion of NKp46-expressing cells (e.g., tumor cells) in vivo.

The methods of the disclosure are utilized advantageously for the treatment of cancers and other proliferative diseases characterized by NKp46-expressing cells, including, but not limited to lymphomas, e.g., CTCLs, PTCLs.

In some embodiments, prior to the administration of the anti-NKp46 antibody or composition, the presence of NKp46 on cells (e.g., tumor cells) of the patient will be assessed, e.g., to determine the relative level and activity of NKp46-positive cells in the patient as well as to confirm the binding efficacy of the antibodies to the cells of the patient. A patient whose tumor cells express NKp46 can then be treated with an anti-NKp46 antibody or composition. This can be accomplished by obtaining a sample of PBLs or tumor cells from the site of the disorder, and testing e.g., using immunoassays, to determine the relative prominence of NKp46 and optionally further other markers on the cells. Other methods can also be used to detect expression of NKp46 and other genes, such as RNA-based methods, e.g., RT-PCR or Northern blotting.

In one embodiment, where it is sought to inhibit the activity or growth of, or deplete, a patient's NKp46-positive cells, the ability of the anti-NKp46 antibody to inhibit proliferation of or deplete a patient's NKp46-positive cells can optionally be assessed. If the NKp46-positive cells are depleted by the anti-NKp46 antibody or composition, the patient is determined to be responsive to therapy with an anti-NKp46 antibody or composition, and optionally the patient is treated with an anti-NKp46 antibody or composition.

The treatment may involve multiple rounds of antibody or compound administration. For example, following an initial round of administration, the level and/or activity of NKp46-expressing cells (e.g., on malignant tumor cells), in the patient will generally be re-measured, and, if still elevated, an additional round of administration can be performed. In this way, multiple rounds of NKp46 detection and antibody or compound administration can be performed, e.g., until the disorder is brought under control.

In some embodiments, the method may comprise the additional step of administering to said patient an appropriate additional (second) therapeutic agent selected from an immunomodulatory agent, a hormonal agent, a chemotherapeutic agent, or a second antibody (e.g., a depleting antibody) that binds to a polypeptide present on a NKp46-expressing cell. Such additional agents can be administered to said patient as a single dosage form together with said antibody, or as a separate dosage form. The dosage of the antibody (or antibody and the dosage of the additional therapeutic agent collectively) are sufficient to detectably induce, promote, and/or enhance a therapeutic response in the patient. Where administered separately, the antibody, fragment, or derivative and the additional therapeutic agent are desirably administered under conditions (e.g., with respect to timing, number of doses, etc.) that result in a detectable combined therapeutic benefit to the patient.

For tumor treatment, for example, the administration of an anti-NKp46 composition may be used in combination with classical approaches, such as surgery, radiotherapy, chemotherapy, and the like. Provides are combined therapies in which the anti-NKp46 antibodies are used simultaneously with, before, or after surgery or radiation treatment; or are administered to patients with, before, or after conventional chemotherapeutic, radiotherapeutic or anti-angiogenic agents, or targeted immunotoxins or coaguligands.

The anti-NKp46 compounds may be useful, for example to treat lymphoproliferative disease of granular lymphocytes (LDGL), particularly NK-LDGL (NK-type lymphoproliferative disease of granular lymphocytes; alternatively called NK-LGL). NK-LDGL refers to a class of proliferative disorders that is caused by the clonal expansion of NK cells or NK-like cells, i.e., large granular lymphocytes showing a characteristic combination of surface antigen expression (e.g., CD3−, CD56+, CD16+, etc.).

The anti-NKp46 compounds may be useful, for example to treat a cutaneous T-cell lymphoma (CTCL), for example a CD4+ T cell lymphoma such as Sezary Syndrome or Mycosis Fungoides.

The anti-NKp46 compounds may be generally useful to treat a variety of PTCLs. In one embodiment of any of the therapeutic uses or PTCL treatment or prevention methods herein, the individual has a NK/T-lymphoma. In one embodiment of any of the therapeutic uses or PTCL treatment or prevention methods herein, the individual has an enteropathy associated T cell lymphoma (EATL), RCDI or RCDII. In one embodiment of any of the therapeutic uses or PTCL treatment or prevention methods herein, the individual has an anaplastic large cell lymphoma (ALCL). In one embodiment of any of the therapeutic uses or PTCL treatment or prevention methods herein, the individual has a PTCL-NOS (PTCL-not otherwise specified), also referred to as PCTL-U or PTCL-unspecified; PCTL-NOS are a type of aggressive lymphoma, mainly of nodal type, but extranodal involvement is common. The majority of nodal cases are CD4+ and CD8−, and CD30 can be expressed in large cell variants.

In one embodiment, the antibodies of the disclosure are used to treat an individual having celiac disease (coeliac disease; CD), including celiac disease and advanced or refractory celiac disease stages. In one embodiment, the individual has a refractory, progressing or advanced celiac disease, optionally wherein the celiac disease is an RCD, an RCDI, or a RCDII.

In one embodiment of any of the therapeutic uses or PTCL treatment or prevention methods herein, the treatment or prevention of a LDGL or a PTCL (e.g., an EATL, an ALCL, a PTCL-NOS, or a pre-malignant condition thereof) in an individual comprises:

a) determining the NKp46 polypeptide status of malignant (or pre-malignant) cells within the individual having a lymphoma or a pre-malignant condition (e.g., a CTCL, a LDGL, a PTCL, celiac disease, etc.), and b) upon a determination that the patient that a NKp46 polypeptide is expressed on the surface of the cells (e.g., is prominently expressed; expressed at a high level and/or at high intensity of staining with an anti-NKp46 antibody, compared to a reference), administering to the individual a compound that binds a NKp46 polypeptide of any of the embodiments herein.

In one embodiment of any the treatment methods or uses herein, NK/T lymphoma, nasal type, is treated, and the method does not require (e.g., is free of, or does not use, or does not comprise) a step of determining the NKp46 polypeptide status of malignant cells within the individual having a PTCL prior to administration of a compound that binds a NKp46 polypeptide.

In a further aspect, it has been found that patients with NKp46-positive PTCL-NOS can have tumors that are CD30-negative (tumor cells do not express CD30 on their surface). Thus, provided are methods of treating a CD30-negative PTCL, e.g., a PTCL-NOS, comprising administering a compound that binds a NKp46 polypeptide to a patient having CD30-negative PTCL. In another embodiment of treating an individual having a PTCL, the method comprises administering a compound that binds a NKp46 polypeptide to an individual having a PTCL who is refractive to treatment with an anti-CD30 antibody. In other embodiments, when PTCLs are CD30-positive (e.g., anaplastic large cell lymphomas which broadly express CD30, certain PTCL-NOS), a compound that binds a NKp46 polypeptide can be administered in combination with an anti-CD30 antibody (e.g., a depleting anti-CD30 antibody, for example an anti-CD30 antibody linked to a toxic moiety).

In one embodiment, provided is a method for detecting a lymphoma, e.g., a peripheral T cell lymphoma, in an individual, the method comprising detecting a NKp46 nucleic acid or polypeptide in a biological sample (e.g., on a cell)

from an individual. In one embodiment, provided is a method for detecting an aggressive or advanced (e.g., stage IV or higher) peripheral T cell lymphoma in an individual, the method comprising detecting a NKp46 nucleic acid or polypeptide in a biological sample (e.g., on a cell) from an individual. A determination that a biological sample expresses NKp46 indicates that the patient has a lymphoma (e.g., a peripheral T cell lymphoma (or advanced/aggressive PTCL)). In one embodiment, the method comprises determining the level of expression of a NKp46 nucleic acid or polypeptide in a biological sample and comparing the level to a reference level (e.g., a value, weak cell surface staining, etc.) corresponding to a health individual. A determination that a biological sample expresses NKp46 nucleic acid or polypeptide at a level that is increased compared to the reference level indicates that the patients has a lymphoma (e.g., a peripheral T cell lymphoma). Optionally, detecting an NKp46 polypeptide in a biological sample comprises detecting NKp46 polypeptide expressed on the surface of a malignant lymphocyte.

Optionally, in any embodiment, determining the NKp46 polypeptide status of cells comprises conducting an immunohistochemistry assay using a sample from an individual. Optionally determining the NKp46 polypeptide status of cells comprises conducting a flow cytometry assay using a sample from an individual. Both IHC and flow cytometry can detect surface expression of NKp46.

Optionally, the compound that binds an NKp46 polypeptide is administered between once daily and once per month. Optionally, the composition is administered as monotherapy. Optionally, the composition is administered in combination with a second therapeutic agent. Optionally, the composition is administered in combination with an anti-cancer agent.

In one embodiment, provided is a method of producing a composition for the treatment of peripheral T cell lymphoma or for use in the prevention of peripheral T cell lymphoma in a mammalian subject, said method comprising the steps of: a) providing a plurality of test compositions comprising an anti-NKp46 antibody of the disclosure; b) testing each compound for the ability to bind NKp46 and/or cause the depletion of NKp46-expressing cells; and c) selecting a compound which binds a NKp46 polypeptide and/or causes the depletion of NKp46-expressing cells as suitable for the treatment of peripheral T cell lymphoma (or a pre-malignant condition) or for use in the prevention of peripheral T cell lymphoma (e.g., by treating a pre-malignant condition).

Optionally, the method further comprises producing a quantity of the compound selected in step c) and/or formulation a quantity of the compound selected in step c) with a pharmaceutically acceptable excipient.

In one embodiment, provided is a method comprising: (a) determining whether an individual has a peripheral T cell lymphoma; and (b) if the individual has a peripheral T cell lymphoma, treating the individual with a therapeutically active amount of a compound of the disclosure that binds a NKp46 polypeptide.

In one embodiment, determining whether an individual has a peripheral T cell lymphoma is made according to standard medical guidelines.

In one embodiment, determining whether an individual has a peripheral T cell lymphoma comprises identifying a population of abnormal cells or abnormal numbers of cells.

Optionally, said identification is by flow cytometry. Optionally, the method further comprises sorting or isolating the population of abnormal cells.

In one embodiment, determining whether an individual has a peripheral T cell lymphoma comprises detecting cytogenetic aberrations (e.g., assessing karyotype).

In one embodiment, determining whether an individual has a peripheral T cell lymphoma comprises sorting the population of abnormal cells; and contacting nucleic acid isolated from the sorted cells with one or more oligonucleotides, wherein the contacting determines the presence of a neoplastic genetic marker; thereby detecting the presence of peripheral T cell lymphoma.

In one embodiment, determining whether an individual has a peripheral T cell lymphoma comprises assessing the levels of a serum protein in the individual.

Optionally, the method further comprises a step of assessing, following treatment with a compound that binds a NKp46 polypeptide, whether the individual has an amelioration in peripheral T cell lymphoma, e.g., whether the individual has decreased numbers of peripheral T cell lymphoma cells.

In one embodiment of any aspect herein, the PTCL is an aggressive and/or advanced PTCL. In one embodiment, the PTCL is aggressive non-cutaneous PTCL. In one embodiment, the PTCL is PTCL-NOS. In one embodiment, the PTCL is a nodal (e.g., primarily nodal) PTCL, for example a PTCL-NOS, AITL, or ALCL (ALK+ or ALK−). In one embodiment, the PTCL is an anaplastic large cell lymphoma (ALCL), optionally an ALK-negative ALCL. In one embodiment, the PTCL is an angioimmunoblastic T-cell lymphoma (AITL), optionally a cutaneous AITL, optionally a non-cutaneous AITL. In one embodiment, a PTCL may be an aggressive, non-cutaneous, primarily nodal PCTL. In one embodiment, the PTCL is an extranodal (e.g., primarily extranodal) PTCL. In one example a PTCL may be an aggressive, non-cutaneous, extranodal PCTL. In one embodiment, the PTCL is an adult T cell leukemia or lymphoma (ATL), e.g., an HTLV+ATL. In one embodiment, the PTCL is an orthovisceral extranodal disease, e.g., NK-/T cell lymphoma or an enteropathy-associated T cell lymphoma. In one embodiment, the PTCL is an extranodal NK-/T-cell lymphoma, nasal type. In one embodiment, the PTCL is an enteropathy-associated T cell lymphoma (EATL).

In one embodiment of any aspect herein, the PTCL is a CD30 positive PTCL (e.g., an ALK-negative ALCL) and the anti-NKp46 antibody is administered in combination with an anti-CD30 antibody. In one embodiment of any aspect herein, the PTCL is a CD4 positive PTCL and the anti-NKp46 antibody is administered in combination with an anti-CD4 antibody.

In one embodiment of any aspect herein, the PTCL is characterized by absence of NK cell—associated or NK-specific markers, e.g., CD56 and/or CD57. In one embodiment of any aspect herein, the PTCL is characterized by presence of NK cell—associated or NK-specific markers, e.g., CD56 and/or CD57.

The antigen-binding compounds can be included in kits. The kits may optionally further contain any number of antibodies and/or other compounds, e.g., 1, 2, 3, 4, or any other number of anti-NKp46 antibodies and/or other compounds. It will be appreciated that this description of the contents of the kits is not limiting in any way. For example, the kit may contain other types of therapeutic or diagnostic agents. Preferably, the kits also include instructions for using the antibodies and/or agents, e.g., detailing the herein-described methods.

Dosage Forms

Therapeutic formulations of compounds are prepared for storage by mixing the compound (e.g., antibody) having the desired degree of purity with optional pharmaceutically acceptable carriers, excipients, or stabilizers in the form of lyophilized formulations or aqueous solutions. For general information concerning formulations, see, e.g., Gilman et al. (eds.), The Pharmacological Bases of Therapeutics, 8$^{th}$ Ed. (Pergamon Press, 1990); Gennaro (ed.), Remington's Pharmaceutical Sciences, 18th Edition (Mack Publishing Co., Easton, Pa., 1990); Avis et al. (eds.), Pharmaceutical Dosage Forms: Parenteral Medications (Dekker, New York, 1993); Lieberman et al. (eds.), Pharmaceutical Dosage Forms: Tablets (Dekker, New York, 1990); Lieberman et al. (eds.) Pharmaceutical Dosage Forms: Disperse Systems (Dekker, New York, 1990); and Walters (ed.), Dermatological and Transdermal Formulations (Drugs and the Pharmaceutical Sciences), Vol 119 (Dekker, New York, 2002).

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low-molecular-weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as ethylenediaminetetraacetic acid (EDTA); sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or PEG.

Lyophilized formulations adapted for subcutaneous administration are described, for example, in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

The formulation herein may also contain more than one active compound (a second medicament as noted above), preferably those with complementary activities that do not adversely affect each other. The type and effective amounts of such medicaments depend, for example, on the amount and type of compound present in the formulation, and clinical parameters of the subjects. The preferred such second medicaments are noted above.

The active ingredients may also be entrapped in microcapsules prepared, e.g., by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's Pharmaceutical Sciences, supra, for example.

Sustained-release formulations may be prepared. Suitable examples of sustained-release preparations include semipermeable matrices of solid hydrophobic polymers containing the compound, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Further aspects and advantages of this invention will be disclosed in the following experimental section, which should be regarded as illustrative and not limiting the scope of this application.

EXAMPLES

Example 1— NKp46 is Expressed in PTCL

Tumor biopsies were obtained and staining was performed on frozen samples. NKp46 was detected with anti-human NKp46 antibody clone "9E2" (mIgG1), Beckton Dickinson, Franklin Lakes, NJ, USA, product ref. 557911, by DAB chromogenic detection according to standard protocols, adapted for immunostaining with BenchMark XT Ventana Roche. For all staining control isotype (mIgG1) and control DAB were performed. CD30 was additionally stained. Tumors 3, 4 and 5 were from the same patient. Tumors 1-5 are from patients having PTCL not otherwise specified. Tumors 6-8 are mycosis fungoides samples, a cutaneous T cell lymphoma (CTCL).

PTCL from each of the samples from patient from which tumor samples 3, 4 and 5 were obtained had strong membrane staining, with a high percentage of cells being NKp46 positive. The patient from which samples 3-5 were obtained had advanced (stage IV) disease. On the other hand, samples 1, 2, 6, 7 and 8 representing less advanced disease (stage I or II) all had either no staining or low percentages of NKp46+ tumor cells. Consequently, while some tumors are capable of expressing NKp46 at high levels and are thus suitable for targeting with an NKp46 binding agent, tumor cells may acquire the NK marker NKp46 at more advanced stages of disease, or more aggressive disease. NKp46 may therefore be a particularly suitable target for treatment of advanced disease, or for preventing progression of disease to advanced stages. Additionally, treatment of earlier stage disease with an NKp46 binding agent may benefit from diagnostic (e.g., theranostic) assays to identify patients having prominent expression of NKp46 on the surface of tumor cells. The NKp46 positive tumors were CD30 negative; NKp46 may therefore furthermore represent a therapeutic target when anti-CD30 antibodies cannot be used (or when tumors resistant to anti-CD30 antibody).

Example 2— NKp46 is Expressed in Samples from ALCL and Ortho Visceral Extranodal Disease (NK/T Lymphoma and EATL)

MEC04 and SNK6 NK/T lymphoma cells were stained for NKp46 expression using flow cytometry (FACS), together with characterization of various cell surface markers. NKp46 was stained with anti-NKp46 antibody linked to phycoerythrin (PE), Additional markers evaluated were hCD56 PE, hCD183/CXCR3 PE, hCD3 PE, hCD4 PE, hCD8 PE and CD54/ICAM PE. Cells were harvested and stained using PE-labeled antibodies. After two washes, stainings were acquired on a BD FACS Canto II and analyzed using the FlowJo software.

Results are shown in FIG. 1. Anti-NKp46 antibody showed staining on the MEC04 and SNK6 cells, although with greater expression on SNK6. MEC04 and SNK6 cells were additionally strongly stained with CD183 (CXCR3), CD56 and CD54 (ICAM), but not CD3, CD4 or CD8 (the most common phenotype of extranodal NK/Tlymphomas are surface CD3– and CD56+).

NK/T lymphoma cells, and in particular extranodal NK/T cell lymphoma, nasal type, can express NKp46, thereby providing the possibility to treat NK/Tlymphoma with anti-NKp46 antibodies. Additionally, NKp46-positive NK/Tlymphoma tumors were found to express CD183 (CXCR3), CD56 and CD54 (ICAM), which may permit administration of anti-NKp46 in poor prognosis patients, notably those having CXCR3 expression typically associated with poor disease prognosis.

Immunohistochemistry (IHC) was carried out to provide confirmation on patient samples and for different indications, by staining primary tumor cells from human patients in frozen tissue sections with labelled anti-NKp46 antibody. Briefly, cell lines known to be positive and negative for NKp46 expression were used as positive and negative controls, respectively. Next, frozen hematopoietic tissues sections from healthy donors were stained for NKp46 expression, all of which were negative for NKp46 expression. In NK/T lymphomas, nasal type, 6 patient samples were tested, of which 5 samples were interpretable. All 5 interpretable samples were positively stained, confirming that NK/T lymphomas express NKp46. In samples from patients diagnosed with enteropathy-associated T cell lymphoma (EATL), of 6 patient samples, 5 samples were interpretable, of which in turn 2 were positively stained and 3 were negative for staining, confirming that EATL cells can express NKp46. In samples from patients diagnosed with anaplastic large cell lymphoma (ALCL), of 4 interpretable patient samples, 3 of which were positively stained and 1 were negative for staining, confirming that ALCL cells can express NKp46. Of the ALCL that stained positive for NKp46, 2 samples were ALK+ while one was ALK–.

Example 3—Generation of New Anti-huNKp46 Antibodies

A recombinant human NKp46 extracellular domain recombinant-Fc protein was produced and used to immunize Balb/c mice. Mice received one primo-immunization with an emulsion of 50 µg NKp46 protein and Complete Freund Adjuvant, intraperitoneally, a 2nd immunization with an emulsion of 50 µg NKp46 protein and Incomplete Freund Adjuvant, intraperitoneally, and finally a boost with 10 µg NKp46 protein, intravenously. Immune spleen cells were fused 3 days after the boost with X63.Ag8.653 immortalized B cells, and cultured in the presence of irradiated spleen cells.

Primary screen: Supernatant (SN) of growing clones were tested in a primary screen by flow cytometry using a reporter cell line expressing the human NKp46 construct at the cell surface. The reporter cell lines were generated by transduction of the DO. 11. 10 mouse T cell hybridoma with retroviral particles encoding a chimeric protein in which the intra-cytoplasmic domain of mouse CD3ζ was fused to the extracellular portion of human NKp46. For FACS screening, the presence of reacting antibodies in supernatants was revealed by Goat anti-mouse polyclonal antibody (pAb) labeled with PE.

120 antibodies that bound NKp46 were selected for further assessment, which included, inter alia, 8B6A, 8B6B, 9H11A, 9H11B and 17E1. Antibodies were then produced as chimeric human IgG1 antibodies.

Example 4—Binding Study of Anti-NKp46 Antibodies on Cells Expressing Human NKp46

The antibodies (including 8B6A, 8B6B, 9H11A, 9H11B and 17E1) were tested for binding to human NKp46 (hNKp46) protein. The data were analyzed by flow cytometry.

Flow cytometry: Cells were harvested and stained in PBS 1×/BSA 0.2%/EDTA 2 mM buffer during 30 minutes at 4° C. using a dose-range of the anti-NKp46 mAbs. After two washes in staining buffer, cells incubated with anti-NKp46 antibodies were stained for 30 min at 4° C. with mouse anti-human IgG1-PE monoclonal antibodies from Miltenyi (dil. 1/10). After two washes, the stainings were acquired on the HTFC Intellicyt device and analyzed using the ForeCyt software.

8B6A, 8B6B, 9H11A, 9H11B and 17E1 were found to bind to human NKp46 with good EC50. Results are shown in Table 1.

TABLE 1

| Clone CHG1-M-H46 | EC50 (µg/ml)/Raji-hNKp46 Med |
|---|---|
| 8B6-A | 0.148 |
| 8B6-B | 0.076 |
| 9H11-A | 0.051 |
| 9H11-B | 0.124 |
| 17E1 | 0.055 |

Example 5—Binding Affinity of Anti-NKp46 for NKp46

Competition and Affinity Study by Surface Plasmon Resonance (SPR)

Biacore T100 General Procedure and Reagents

SPR measurements were performed on a Biacore T100 apparatus (Biacore GE Healthcare) at 25° C. In all Biacore experiments HBS-EP+(Biacore GE Healthcare) and NaOH 10 mM NaCl 500 mM served as running buffer and regeneration buffer respectively. Sensorgrams were analyzed with Biacore T100 Evaluation software. Protein-G was purchase from GE Healthcare and Anti-His antibody from QIAGEN. Human 6×His tagged NKp46 recombinant proteins (NKp46-His) were cloned, produced and purified at Innate Pharma.

Immobilization of Protein-G and of Anti-his Antibodies

Protein-A and Anti-His antibodies were immobilized covalently to carboxyl groups in the dextran layer on a Sensor Chip CMS. The chip surface was activated with EDC/NHS (N-ethyl-N'-(3-dimethylaminopropyl) carbodiimidehydrochloride and N-hydroxysuccinimide (Biacore GE Healthcare)). Protein-A and Anti-His antibodies were diluted to 10 µg/ml in coupling buffer (10 mM acetate, pH 5.6) and injected until the appropriate immobilization level was reached (i.e., 2000 to 2500 RU). Deactivation of the remaining activated groups was performed using 100 mM ethanolamine pH 8 (Biacore GE Healthcare).

Affinity Study

Affinity study has been performed using the Protein-G chip. Monovalent affinity study was done following the Single Cycle Kinetic (SCK) protocol. Five serial dilutions of soluble NKp46-His recombinant proteins ranging from 12.5 to 200 nM were injected over the captured Anti-NKp46 antibodies (without regeneration) and allowed to dissociate for 10 min before regeneration. For each antibody, the entire sensorgram was fitted using the 1:1 SCK binding model. Results are shown in Table 2.

TABLE 2

| Antibody | ka (M−1*s−1) | kd (s−1) | KD (M) |
|---|---|---|---|
| 8B6-A | 2.67E+05 | 0.001089 | 4.08E−09 |
| 8B6-B | 2.71E+05 | 0.001101 | 4.07E−09 |
| 9H11-A | 2.73E+05 | 1.99E−04 | 7.28E−10 |
| 9H11-B | 2.83E+05 | 2.53E−04 | 8.92E−10 |

Example 6—Cross-Reaction of Anti-NKp46 Antibodies with *Macaca fascicularis* NKp46 Protein The antibodies (including 8B6A, 8B6B, 9H11A, 9H11B and 17E1) were assessed for binding to *Macaca fascicularis* NKp46 (cyno NKp46) protein. The sequence of cyno NKp46 (shown below) was cloned from *Macaca fascicularis* cDNA and transfected into the CHO cell line. The binding of CHG1-M-H46 to CHO-cynoNKp46 was analyzed by flow cytometry. *Macaca fascicularis* NKp46 amino acid sequence:

```
                                        (SEQ ID NO: 2)
         M S S T L R A L L C L G L C L S Q
         R I S A P K Q T L P K P I I R A E
         S T Y M V P K E K Q A T L C C Q G
         S Y G A V E Y Q L H F E G S L F A
         V E R P K P P E R I N G V K F H I
         P D M N S R K A G R Y S C I Y R V
         G E L W S E R S D L L D L V V T E
         M Y D T P T L S V H P G P E V T S
         G E K V T F Y C R L D T A T S M F
         L L L K E G R S R D V Q R S Y G K
         V Q A E F P M G P V T T A H R G S
         Y R C F G S Y N N Y A W S F P S E
         P V K L L V T G D I E N T S L A P
         T D P T F P D S W D T C L L T R E
         T G L Q K D L A L W D H T A Q N L
         L R M G L A F L V L V A L V C L L
         V E D W L S R K R T R E Q A S R A
         S T W E G R R R L N K H K D S E E
```

Flow cytometry: CHO cells were harvested and stained in PBS 1x/BSA 0.2%/EDTA 2 mM buffer during 30 minutes at 4° C. using a dose-range of the anti-NKp46 mAbs. After two washes in staining buffer, cells incubated with anti-NKp46 antibodies were stained for 30 min at 4° C. with mouse anti-human IgG1-PE monoclonal antibodies from Miltenyi (dil 1/10). After two washes, stainings were acquired on a HTFC Intellicyt and analyzed using ForeCyt software.

8B6A, 8B6B, 9H11A, 9H11B and 17E1 bind to cynomolgus NKp46 with good EC50. Results are shown in Table 3.

TABLE 3

| Clone CHG1-M-H46 | EC50 (µg/ml)/CHO Cyno NKp46 |
|---|---|
| 8B6-A | 0.029 |
| 8B6-B | 0.028 |
| 9H11-A | 0.026 |
| 9H11-B | 0.025 |
| 17E1 | 0.059 |

Example 7: Induction of ADCC by NK Cells Toward an NKp46+NK/T Lymphoma Cell Line Antibodies selected for binding to NKp46 were tested as human IgG1 for functional ability to direct NK cells to lyse a RAJI tumor cell line made to express human NKp46. While many of the antibodies did not induce cytotoxicity in this assay, a several antibodies (8B6A, 8B6B, 9H11A, 9H11B and 17E1) were effective in inducing ADCC.

Antibodies 8B6A, 8B6B, 9H11A, 9H11B and 17E1 were tested for functional ability to direct NK cells to mediate ADCC towards NKp46-positive tumor target SNK6 NK/T lymphoma cells. Briefly, the cytolytic activity of human NK cell line KHYG-1 transfected with human CD16 (V isoform) or purified NK was assessed in a classical 4-h $^{51}$Cr-release assay in 96 well plates U from Greiner. SNK6 cells were labelled with $^{51}$Cr (100 µCi (3.7 MBq)/1×106 cells), then mixed with KHYG-transfected with hCD16 (V allele at residue 158) (to bind human IgG1) or NK cells at an effector/target ratio equal to 10, in the presence of antibody at indicated concentrations. After brief centrifugation and 4 hours of incubation at 37° C., 50 µL supernatant were removed, and the $^{51}$Cr release was measured with a TopCount NXT beta detector (PerkinElmer Life Sciences, Boston, MA). All experimental groups were analyzed in triplicate, and the percentage of specific lysis was determined as follows: 100×(mean cpm experimental release—mean cpm spontaneous release)/(mean cpm total release—mean cpm spontaneous release). Percentage of total release obtained by lysis of target cells with 2% Triton X100 (Sigma).

Figure 2A:
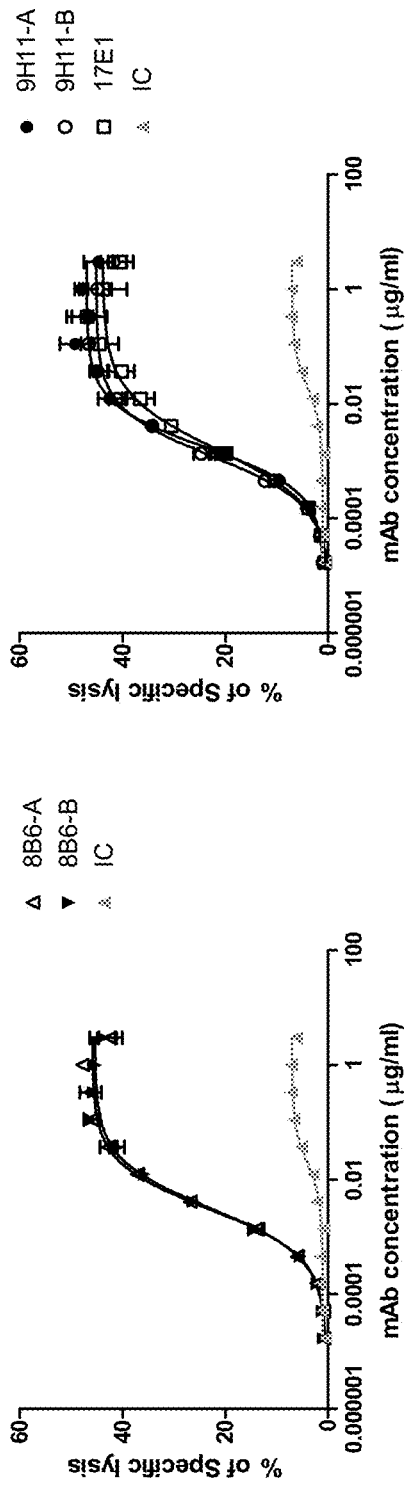
FIGS. 2A-2B show induction of ADCC by NK cells toward an NKp46+NK/T lymphoma cell line, SNK6. In these ADCC assays, were used as effector cells: A. the NK cell line transfected with human CD16, B. NK purified from human blood. In both cases, the SNK6 target (T) cells were loaded with 51Cr, mix with effector (E) cells at a ratio E:T=10:1 in the presence of chimeric anti-NKp46 at indicated concentrations. The release of $^{51}$Cr in the medium was assessed after 4 hours incubation time. The percentage of specific lysis was calculated relatively to controls of minimal and maximal release.
Figure 2B:
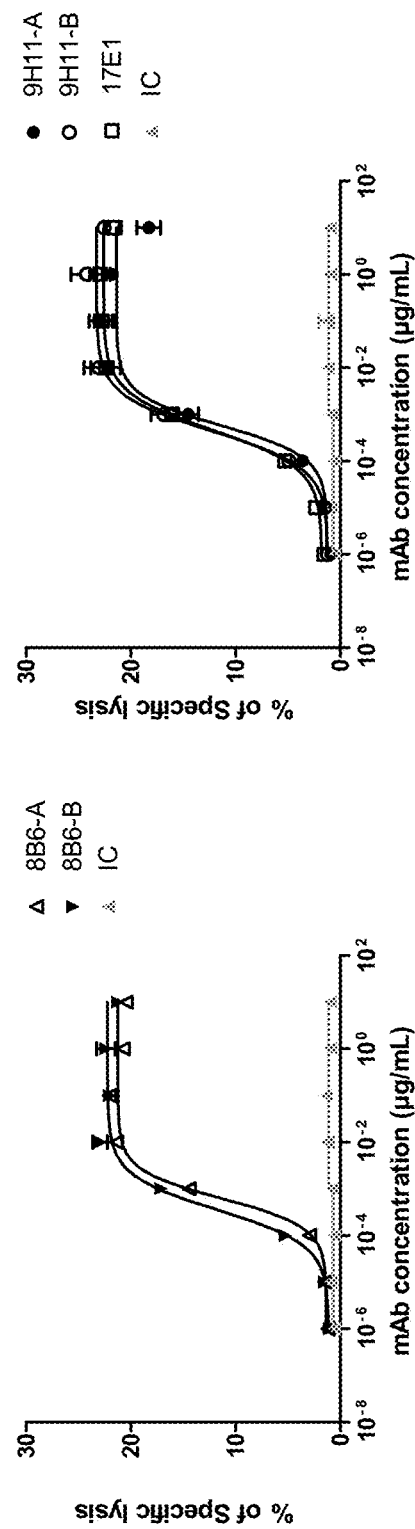

Results are shown in FIG. 2. 8B6A, 8B6B, 9H11A, 9H11B and 17E1 induced specific lysis of SNK6 lymphoma cells by the human KHYG-1 hCD16V NK cell line or purified NK cells compared to negative controls (Irrelevant chimeric IgG1 isotype control antibody), thereby showing that these antibodies induce ADCC toward NKp46-expressing target cells.

Example 8—Naked Anti-NKp46 Antibodies Show Anti-Tumoral Efficacy in a RAJI Xenograft Mouse Model Antibodies were tested in a mouse long-term Raji-hNKp46 tumor model in which Raji cells expressed high level of NKp46. SCID mice were intravenously (i.v.) engrafted with 5.10$^6$ Raji-hNKp46 and treated intraperitoneally (i.p.) with either isotype control antibody (IC) or chimeric antibodies 8B6-A, 9H11-B or 17E1 at the dosage of 300 µg/mouse, twice/week for 3 weeks from the day of tumor cell graft.

Raji-hNKp46 were cultured in complete RPMI 1640 culture medium containing supplemented with 10% of Fetal Bovine Serum Heat Inactivated, 1% L-glutamine, 1% Sodium/Pyruvate and without antibodies prior to injection into mice. Mice were weighed twice per week. Kaplan-Meier survival curves were established to assess survival of treated mice.

Figure 3:
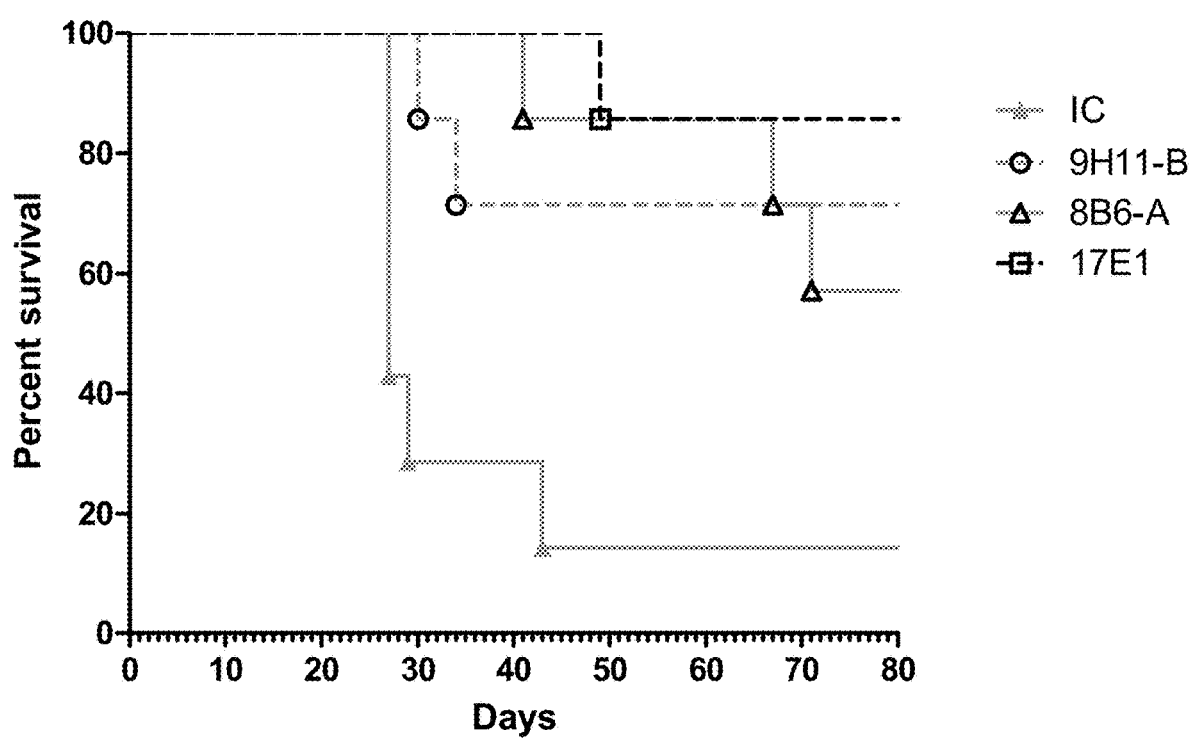
FIG. 3 shows anti-tumoral efficacy using chimeric anti-NKp46 in a Raji xenograft mouse model. 5×10⁶ Raji cells expressing high level of NKp46 were intravenously (i.v) engrafted in SCID mice. One day after tumor cell graft, mice were treated intraperitoneally with either isotype control antibody (IC) or anti-NKp46 chimeric antibodies (8B6-A, 9H11-B, 17E1) at the dosage of 300 μg/mouse, twice/week for 3 weeks. Mice were weighed twice per week. Kaplan Meier survival curves were established to assess survival of treated mice.

Results are shown in FIG. 3. All chimeric antibodies showed anti-tumoral activity. Animals receiving isotype control had a median survival of 27 days. The mice treated with 8B6-A, 9H11-B or 17E1 antibodies showed more than 50% of animals still alive at day 70, this preventing the calculation of the median survival and indicating a very strong anti-tumoral effect.

Example 9: Epitope Mapping of Anti-NKp46 for Binding to NKp46

A competition study between antibodies 8B6A, 8B6B, 9H11A, 9H11B and 17E1 was performed using the Anti-His antibody chip according to the methods described for Example 5. All the soluble analytes were injected at a constant concentration of 10 µg/mL.

For any given pair of anti-NKp46 antibodies, the competitive binding inhibition cycle was performed in four steps. In the first step, NKp46-His recombinant proteins were captured onto the Anti-His chip. Then, the first antibody was injected twice over captured NKp46-His in order to ensure a nearly complete saturation of its own epitopes. In the fourth and final step the second antibody was injected over the first antibody/NKp46 complexes. Second antibody signal was monitored and compared to the signal obtained when the second antibody was injected onto nude captured antigen. After each cycle Anti-His chip was regenerated by a short injection of regeneration buffer.

Figure 4:
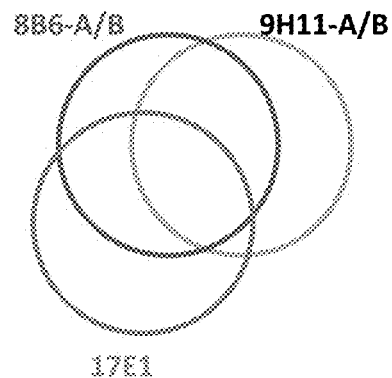
FIG. 4 shows the results of a study to assess competition for binding to human NKp46 (by surface plasmon resonance) amongst combinations of 8B6A, 8B6B, 9H11A, 9H11B and 17E1. Each of the antibodies competed with one another for binding to NKp46 showing that these antibodies all bind to a common region on NKp46.

The competition matrix is shown in FIG. 4. All of antibodies 8B6A, 8B6B, 9H11A, 9H11B and 17E1 competed with one another for binding to NKp46 showing that these antibodies all bind to a common region on NKp46.

Example 10: Epitope Mapping of Anti-NKp46 for Competition with Existing mAbs by Flow Cytometry The antibodies (including 8B6A, 8B6B, 9H11A, 9H11B and 17E1) were assessed for the binding competition with known anti-NKp46 mAbs 195314 (R&D), 9E2 (BD), and Bab281 (BC)) on SNK6 cell line. Bab281, mIgG1, is available commercially from Beckman Coulter, Inc. (Brea, CA, USA) (see Pessino et al, J. Exp. Med, 1998, 188 (5): 953-960 and Sivori et al, Eur J Immunol, 1999. 29:1656-1666) describing chromium release cytotoxicity assays). 9E2, mIgG1, is available commercially from Becton Dickinson (Franklin Lakes, NJ, USA) and Miltenyi Biotec (Bergisch Gladback, Germany) (see Brando et al, (2005) J. Leukoc. Biol. 78:359-371; and El-Sherbiny et al, (2007) Cancer Research 67(18):8444-9). 195314, mIgG2b, is available commercially from R&D Systems, Inc. (Minneapolis, USA) (see Nolte-'t Hoen et al, (2007) Blood 109:670-673). Clones 195314, 9E2 and Bab281 have been reported previously to be blocking interactions of NKp46 with natural ligands.

The binding competition was analysed by flow cytometry. A sub-optimal dose of each commercial mAbs was previously defined.

Sub-optimal dose determination of commercial mAbs: SN K6 cells were harvested and stained in PBS 1x/BSA 0.2%/EDTA 2 mM buffer during 30 minutes at 4° C. using a dose-range of the commercial anti-NKp46 mAbs labeled with PE. After two washes, stainings were acquired on the HTFC Intellicyt device and analyzed using the ForeCyt software. A dose below the saturation plateau was selected for the competition assay.

Binding competition assay: SNK6 cells were harvested and stained in PBS 1x/BSA 0.2%/EDTA 2 mM buffer. The commercial mAbs labeled with PE were added (at a sub-optimal dose) simultaneously with a dose range of CHG1-M-H46 non-labeled and incubated during 30 minutes at 4° C. After two washes, stainings were acquired on the HTFC Intellicyt device and analyzed using the ForeCyt software.

Figure 5:
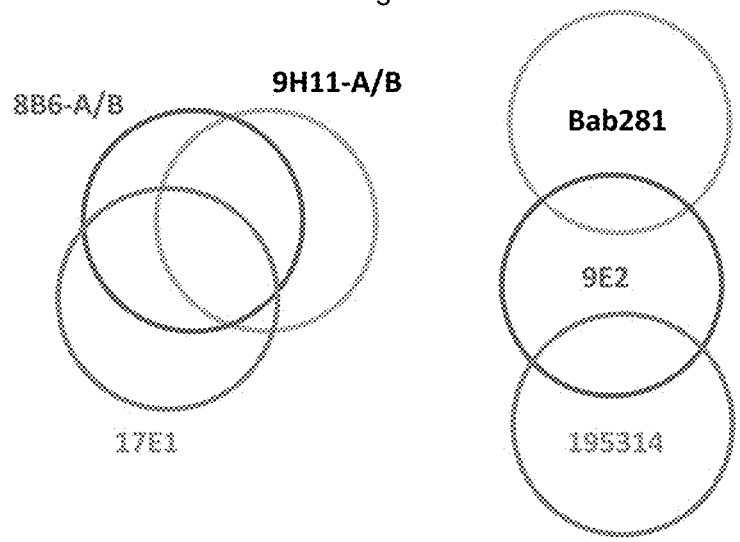
FIG. 5 shows the results of a study to assess competition for binding to human NKp46 (by surface plasmon reflow cytometry) amongst antibodies 8B6A, 8B6B, 9H11A, 9H11B and 17E1 and known antibodies. While the 8B6A, 8B6B, 9H11A, 9H11B and 17E1 group all competed with one another for NKp46, none of them competed with the known antibodies.

The competition matrix is shown in FIG. 5. Antibodies at 1 µg/mL were captured onto Protein-A chip and recombinant human NKp46 proteins were injected at 5 µg/mL together with a second test antibody. The antibodies 8B6A, 8B6B, 9H11A, 9H11B and 17E1 competed with one another for binding to NKp46 proteins. However, none of the antibodies 8B6A, 8B6B, 9H11A, 9H11B or 17E1 competed with any of the known antibodies 195314, 9E2 or Bab281 for binding to NKp46 proteins.

Example 11—Production of ADCs

Antibodies obtained in Example 3 (including IPH1, IPH2, IPH3, 8B6A, 9H11A, 9H11B and 17E1) in PBS were deglycosylated with PNGaseF (New England Biolabs, 800 U/mg of mAb) overnight at 37° C. Completion of the reaction was controlled by LC-ESI-MS.

A two-step process based on use of Click chemistry reactive groups was used in which a lysine based linker with a reactive group is first bound to the acceptor glutamines of the antibodies (in the absence of organic solvent), followed by reaction with a second compound that includes the PBD and a complementary reactive group (in the presence of organic solvent). To obtain the intermediate antibody bound to a reactive linker, 1 mg/mL deglycosylated mAb was incubated with 20 equivalents of a reactive lysine based linker (amino-PEG-azide, structure below) per site of coupling and 5 U/mL BTG overnight at 37° C. in PBS. The antibodies all comprised an acceptor glutamine at amino acid residue 295 (Kabat EU numbering) of their heavy chains, such that the reactive linker was conjugated to residue Q295 on each heavy chain of the antibodies (each antibody has two conjugated moieties; DAR=2).

The structure of the reactive linker was as follows:
NH2-Peg-N3 Spacer:

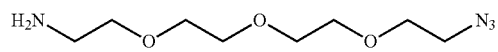

The mAb-reactive linker conjugate was purified by affinity chromatography on protA.

In order to produce the final ADC comprising a pyrrolobenzodiazepine (PBD) dimer, the azide-functionalized antibodies above (2 mg/mL in PBS/1,2-propane-diol 50/50 v/v) were then incubated with 1.75 molar equivalent of DBCO-derivatized-PBD per site of coupling (the DBCO reacts with the azide). The mixture was incubated for 48-72 h at RT with gentle agitation. Completion of the reaction was controlled by LC-ESI-MS. Excess of derivatized-PBD was removed by dialysis (MWCO=10 kDa), followed by purification by size exclusion chromatography (Superdex 200 10/300GL column, GEHealthcare). The final compounds were concentrated on Amicon 30K devices.

The structure of the DBCO-derivatized-PBD compound is shown as follows:
DBCO-val-ala—PBD:

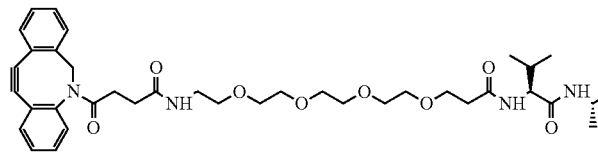

The final structure of the compound linked to the glutamine (represented by "mAb") is shown as follows:
mAb-PEG-DBCO-PBD:

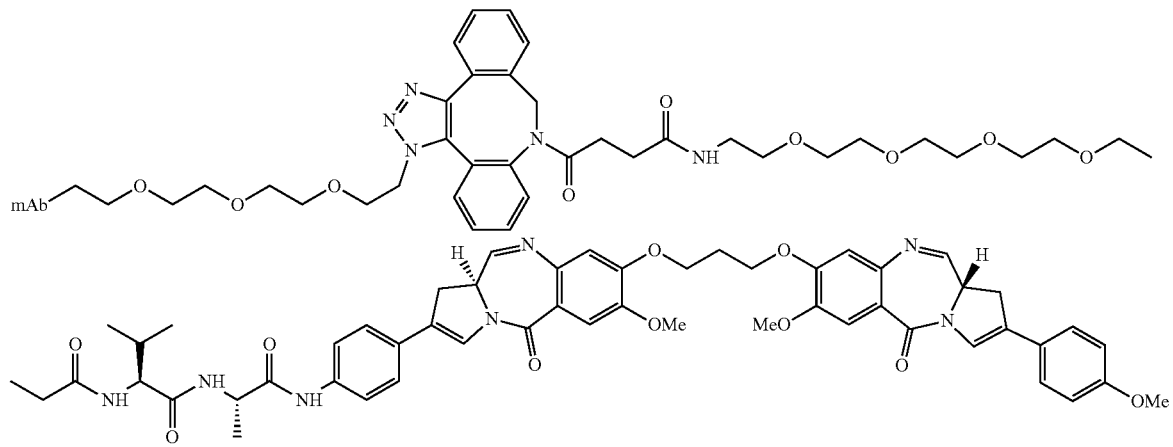

Example 12—Comparative Evaluation of Antibodies as ADCs in Lymphoma Models

The anti-NKp46 antibody-drug conjugates of Example 11 bearing PDB dimers with a DAR=2 were tested in different tumor models using first native or NKp46-transduced (high NKp46 expression) human Raji cells (Raji and Raji-NKp46 respectively) to assess efficacy in a context of high NKp46 expression. In a second model, the anti-NKp46 ADCs were tested for in a human SNK6 cell line derived from a human NK-T-lymphoma, nasal type, that naturally expresses NKp46.

Materials and Methods
Cell Lines and Culture Media:

Raji and Raji-NKp46 were cultured in RPMI 1640 Medium (Life Technologies SAS,) supplemented with 10% decomplemented FBS (Life Technologies SAS)+2 mM L-Glutamine (Life Technologies SAS)+1 mM Sodium pyruvate (Life Technologies SAS), at 37° C., 5% CO2.

SNK6 cells were cultured in RPMI 1640 Medium (Life Technologies SAS) supplemented with 15% decomplemented FBS (Life Technologies SAS)+2 mM L-Glutamine (Life Technologies SAS)+1 mM Sodium pyruvate (Life Technologies SAS)+100 U/ml recombinant human IL-2 at 37° C., 5% CO2.

Antibody Drug Conjugates (ADCs):

Anti-human NKp46 or negative control antibodies (Ab) were coupled with the PBD toxine with a Drug/Ab ratio 2 in Example 11. The Ab clones used were: 8B6A, 9H11A, 9H11B, 17E1, and antibodies with high affinity to NKp46 that bind to distinct epitopes on NKp46: Ab1, Ab2, Ab3, and Ab negative control.

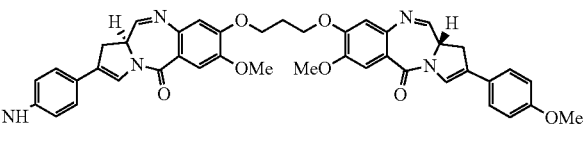

Cytotoxicity Experiments:

Efficacy of PBD-coupled anti-NKp46 (or control) antibodies (ADCs) was assessed by measuring ATP production of cells (reflecting cell viability) using the Cell Titer Glo Luminescent Cell Viability Assay (Promega). 10000 Raji or Raji-NKp46 or 7500 SNK6 cells were seeded in 80 μL of culture medium per wells of white opaque flat bottom 96-wells plate (Fisher Scientific). 20 μL of 5× concentrated ADCs are added per wells (triplicates) in order to obtain 4 or 8 different final concentrations ranging from 10 μg/ml to 0.01 μg/ml+0 μg/ml control (depending on the experiments). After 72 h of incubation at 37° C., 5% CO2, 100 μL per wells of CellTiter Glo reagent (Promega) were added. After 10 minutes of incubation at room temperature in the dark, bioluminescent signal was measured in each wells using the Glomax Luminometer (Promega). Data were analysed using GraphPad Prism software.

Cytometry Experiments:

Cells NKp46 expression was evaluated at the beginning of the cytotoxicity experiment using 100000 cells/point. Cells were incubated on ice in 100 μl of FACS buffer (PBS 1×, SVF 0.2%, EDTA 2 mM, 0.22 μm filtered) containing either 1/10 of PE-conjugated anti hNKp46 (clone 9E2/NKp46, BD Pharmingen) or 1/10 of PE-conjugated mouse IgG1 isotype control (clone MOPC-21, BD pharmingen). Cells were washed twice and resuspended in FACS buffer containing 1/10000 SYTOX Blue Dead Cell Stain (Molecular Probes) just before using the cytometer (BD FACSCanto 10-Color System-BD Biosciences). Data were analysed using FlowJo software.

Results

The half maximal inhibitory concentration ($IC_{50}$) for cytotoxicity towards tumor cells was determined for each of the immunoconjugates.

Raji-NKp46 (High Expression)

In the high expressing Raji-NKp46 cells, immunoconjugates based on antibodies 8B6A, 9H11A, 9H11B, 17E1 were compared to immunoconjugates based on antibodies that bind to distinct epitopes on NKp46: Ab1, Ab2, Ab3, and Ab negative control. All immunoconjugates showed high efficacy and similar $IC_{50}$ values, although 8B6A, 9H11A, 9H11B and 17E1 ADCs displayed modestly lower IC50 values (ranging from an improvement of 15% to 3-fold (mAb 17E1) over the best $IC_{50}$ value for Ab1, Ab2, Ab3. In the Raji (non-transduced) cells that do not express NKp46, $IC_{50}$ values for all immunoconjugates, including negative control, were similar.

SNK6 NK/T Cell Lymphoma

In the SNK6 cells naturally expressing NKp46, immunoconjugates based on antibodies 8B6A, 9H11A, 9H11B, 17E1 were compared to immunoconjugates based on antibodies that bind to distinct epitopes on NKp46: Ab1, Ab2, Ab3, and Ab negative control. In this setting, 8B6A, 9H11A, 9H11B, 17E1 ADCs had much lower $IC_{50}$ values than any of mAbs Ab1, Ab2, Ab3. The ADCs had up 50-fold lower $IC_{50}$ than the mAbs Ab1, Ab2, Ab3 (9H11A: $IC_{50}$=0.00002 μg/ml; 9H11B: $IC_{50}$=0.00001 μg/ml; 17E1: $IC_{50}$=0.00001 μg/ml; Ab1: $IC_{50}$=0.00059 μg/ml; Ab2: $IC_{50}$=0.0007 μg/ml; Ab3: $IC_{50}$=0.0001 μg/ml).

Example 13—Antibodies Internalize in NKp46-Expressing B-Cell Lymphoma and NK/T Lymphoma (Nasal Type)

Internalization of anti-NKp46 antibody 8B6A or negative control (antibodies that do not bind NKp46) was tested by flow cytometry using CypHer5E conjugated antibodies. CypHer5E dye is a red-excitable, pH-sensitive cyanine dye derivative, which is minimally fluorescent at basic pH (as at cell surface) and maximally fluorescent at an acidic pH (as in internal acidic endosomes). A fluorescence signal increase will correlate with the internalization of the CypHer5-conjugated antibody. Antibodies were coupled with CypHer5E using the CypHer5E NHS Ester kit (GE Healthcare Life Sciences) according to the manufacturer's instructions.

50,000 cells (Raji (lacking surface NKp46), Raji-NKp46 and SNK6) per wells were seeded in 96 wells plate and were incubated at 37° C., 5% CO2 for 24 h. CypHer5-coupled antibodies (1 μg/ml) were added in wells containing cells at different time points in order to obtain the following kinetic of incubation of cells with antibodies: 0, 15, 30, 60, 120, 240 minutes and 24 hours. After 24 h, plates were put on ice for 10 minutes (to stop internalization). CypHer5E-antibodies were then added in wells corresponding to the point 0 minute. Cells were washed with cold FACS buffer and resuspended in cold FACS buffer containing 1/10000 SYTOX Blue Dead Cell Stain (Molecular Probes) and kept on ice until using the cytometer (BD FACSCanto 10-Color System-BD Biosciences). Data were analyzed using FlowJo software.

Results showed that antibody 8B6A (but not control antibody) underwent significant intracellular internalization in NKp46-expressing tumor cells (Raji-NKp46 and SNK6), but not in Raji cells that do not express NKp46. Control antibody was not internalized in any of the cell lines.

Example 14—Epitope Mapping by H/D Exchange

HX-MS technology exploits that hydrogen exchange (HX) of a protein can readily be followed by mass spectrometry (MS). By replacing the aqueous solvent containing hydrogen with aqueous solvent containing deuterium, incorporation of a deuterium atom at a given site in a protein will give rise to an increase in mass of 1 Da. This mass increase can be monitored as a function of time by mass spectrometry in quenched samples of the exchange reaction. The deuterium labelling information can be sub-localized to regions in the protein by pepsin digestion under quench conditions and following the mass increase of the resulting peptides.

One use of HX-MS is to probe for sites involved in molecular interactions by identifying regions of reduced hydrogen exchange upon protein-protein complex formation. Usually, binding interfaces will be revealed by marked reductions in hydrogen exchange due to steric exclusion of solvent. Protein-protein complex formation may be detected by HX-MS simply by measuring the total amount of deuterium incorporated in either protein members in the presence and absence of the respective binding partner as a function of time. The HX-MS technique uses the native components, i.e. protein and antibody or Fab fragment, and is performed in solution. Thus HX-MS provides the possibility for mimicking the in vivo conditions (for a recent review on the HX-MS technology, see Wales and Engen, Mass Spectrom. Rev. 25, 158 (2006)).

Materials and Methods:

NKp46: NKp46-His protein was produced and formulated as 20 μM solution in PBS.

mAbs: 8B6A, 9H11A and 17E1 and were formulated 20 μM solution in PBS.

HX-MS experiments: The HDX experiments were automated using a PAL System (CTC Analytics) robot allowing initiation and cessation of exchange, control of temperature and duration of digestion, injection of the deuterated peptides, control of the injection and washing valves and triggering the acquisition of the mass spectrometer and the HPLC. A polystyrene box cooled by Peltier effect at 4° C. contains two Rhéodyne valves (6 channels for injection and 10 channels for desalting), a desalting cartridge (Michrom microtrap) and UPLC column (RRHD Eclipse Plus C18, 2.1×50 mm, 1.8 u). After desalting with an Agilent HPLC pump with 0.4% formic acid at 200 μl/min, the peptides were separated on the UPLC column using an Agilent UPLC pump, with a gradient of 15-70% B at 50 μl/min (A: 0.4% Formic Acid, B: 95% acetonitrile, 0.08% FA). The mass spectrometer was an electrospray-TOF (6210 Agilent). The mapping experiments were carried out by mass spectrometry tandem (MS-MS) using a Bruker Solarix XR (15 T) mass spectrometer. In addition to the Bruker and Agilent software, Magtran (2) and HDExaminer (Sierra Analytics) were used for data processing.

The hydrogen-deuterium exchange was initiated with 10 μL of NKp46 (20 μM) in the presence or absence of an antibody in deuterated PBS. The exchange was carried out at 4° C. for 15 s. The antigen-antibody complex was formed by mixing 10 μL of NKp46 (20 μM) and 10 μL of antibody (20 μM) for at least 30 min at 4° C. The exchange was blocked by mixing a solution of Guanidium Chloride (3M)

with TCEP (400 mM) in glycine-HCl (1M), at a final pH of 2.5. Reduction and denaturation were carried out for 5 min at 4° C. Each experiment was repeated at least three times. Results: Epitope Mapping of 8B6A, 9H11A and 17E1.

The HX time-course of peptides, covering a substantial portion of the primary sequence of the NKp46 polypeptide sequence shown in SEQ ID NO 70, below, were monitored in the presence and absence of 8B6A, 9H11A, or 17E1 for 15 seconds.

```
                                          (SEQ ID NO: 70)
QQQTLPKPF IWAEPHEMVP KEKQVTICCQ

GNYGAVEYQL HFEGSLFAVD RPKPPERINK

VKFYIPDMNS RMAGQYSCIY RVGELWSEPS

NLLDLVVTEM YDTPTLSVHP GPEVISGEK

VTFYCRLDTAT SMFLLLKEGR SSHVQRGYGK

VQAEFPLGPV TTAHRGTYRC FGSYNNHAWS

FPSEPVKLLV TGDIENTSLA PEDPTFPADT

WGTYLLTTET GLQKDHALWD HTAQN
```

The observed deuterium incorporation in the presence or absence of one of these antibody can be divided into two groups: one group of peptides display a deuterium incorporation that is unaffected by the binding of the antibody to NKp46. In contrast, another group of peptides in NKp46 show a lower deuterium incorporation, which reflects that a complex is formed, as the deuterium incorporation is lower in the complexed form than in the non-complexed form. For the peptides of the regions 100-118, 133-151, 150-169, 177-187 differences of deuteration were observed between free NKp46 and the complexed form with antibodies.

The observed deuterium incorporation (in percentage) measured in the presence or absence of 8B6A at 15s exchange showed the 4 following peptides in NKp46 display a deuterium incorporation that is affected by the binding of 8B6A to NKp46: approximately 2 times less deuterium uptake is observed in the region 101-105 as well as in the region 150-169 upon 8B6A binding, whereas a weaker difference was observed in the 133-151 and 177-187 regions.

The observed deuterium incorporation in the presence or absence of 9H11A is showed the 4 following peptides in NKp46 display a deuterium uptake that is affected by the binding of 9H11A to NKp46: the percentage of deuterium incorporation is approximately 4 times lower in the presence of a peptide in the region 101-118 and approximately 2 times lower in the region 150-169, whereas a weaker difference was observed in the 135-151 and 178-187 regions.

The observed deuterium uptake in the presence or absence of 17E1: the 4 following peptides in NKp46 display an incorporation that is affected by the binding of 17E1A to NKp46: more than 2 times less deuterium uptake is observed in the region 150-169, about ⅓ less in the region 100-105, whereas a weaker difference was observed in the 133-151 and 178-187 regions.

CONCLUSION

The epitope regions within residues 101-118 (or 101-105 or 100-105) as well as the region within residues 150-169 display a relative strong protection upon binding of either one of the three mAbs 8B6A, 9H11A and 17E1. The regions containing residues 135-151 (or 133-151) and 178-187 (or 177-187) displayed a weaker (9H11A, 8B6A, 17E1), exchange protection upon binding on the mAbs.

Antibody 9H11A

Two NKp46 peptides are strongly impacted in the presence of 9H11A:

```
NKp46_101-118:
                                          (SEQ ID NO: 71)
DTPTLSVHPGPEVISGEK

NKp46_150-169:
                                          (SEQ ID NO: 72)
VQAEFPLGPVTTAHRGTYRC
```

Residues that significantly contribute to the molecular surface in the peptide are:

| D101 | T102 | T104 | S106 | H108 | P109 | P111 | E112 | I114 | S115 | G116 | E117 | K118 |
|------|------|------|------|------|------|------|------|------|------|------|------|------|
| V150 | Q151 | E153 | P155 | G157 | P158 | T160 | T161 | A162 | H163 | R164 | T166 | R168 |

Two NKp46 peptides are weakly impacted in the presence of 9H11A:

```
NKp46_178-187:
                                          (SEQ ID NO: 74)
WSFPSEPVKL

NKp46_135-151:
                                          (SEQ ID NO: 76)
LKEGRSSHVQRGYGKVQ
```

Residues that significantly contribute to the molecular surface in the peptide are:

| F180 | P181 | E183 | P184 | K186 |      |      |      |      |      |      |
|------|------|------|------|------|------|------|------|------|------|------|
| E137 | G138 | R139 | S140 | S141 | H142 | Q144 | R154 | Y147 | G148 | K149 | V150 | Q151 |

Antibody 8B6A

Two NKp46 peptides are significantly impacted in the presence of 8B6A:

```
NKp46_101-105:
                                          (SEQ ID NO: 73)
DTPTL

NKp46_150-169:
                                          (SEQ ID NO: 72)
VQAEFPLGPVTTAHRGTYRC
```

Residues that significantly contribute to the molecular surface in the peptide are:

| | | | | | | | | | | | |
|---|---|---|---|---|---|---|---|---|---|---|---|
| D101 | T102 | T104 | | | | | | | | | |
| V150 | Q151 | E153 | P155 | G157 | P158 | T160 | T161 | A162 | H163 | R164 | T166 | R168 |

Two NKp46 peptides are weakly impacted in the presence of 8B6A:

NKp46_177-187:
(SEQ ID NO: 75)
AWSFPSEPVKL

NKp46_133-151:
(SEQ ID NO: 77)
LLLKEGRSSHVQRGYGKVQ

Residues that significantly contribute to the molecular surface in the peptide are:

| | | | | | | | | | | | |
|---|---|---|---|---|---|---|---|---|---|---|---|
| F180 | P181 | E183 | P184 | K186 | | | | | | | |
| E137 | G138 | R139 | S140 | S141 | H142 | Q144 | R145 | Y147 | G148 | K149 | V150 | Q151 |

Antibody 17E1

One NKp46 peptide is strongly impacted in the presence of 17E1:

NKp46_150-169:
(SEQ ID NO: 72)
VQAEFPLGPVTTAHRGTYRC

Residues that significantly contribute to the molecular surface in the peptide are:

| | | | | | | | | | | | |
|---|---|---|---|---|---|---|---|---|---|---|---|
| V150 | Q151 | E153 | P155 | G157 | P158 | T160 | T161 | A162 | H163 | R164 | T166 | R168 |

One NKp46 peptide is significantly impacted in the presence of 17E1:

NKp46_100-105:
(SEQ ID NO: 78)
YDTPTL

Residues that significantly contribute to the molecular surface in the peptide are:

| Y100 | D101 | T102 | T104 |
|---|---|---|---|

Two NKp46 peptides are weakly impacted in the presence of 17E1:

NKp46_178-187:
(SEQ ID NO: 74)
WSFPSEPVKL

NKp46_133-151:
(SEQ ID NO: 77)
LLLKEGRSSHVQRGYGKVQ

Residues that significantly contribute to the molecular surface in the peptide are:

| | | | | | | | | | | | |
|---|---|---|---|---|---|---|---|---|---|---|---|
| F180 | P181 | E183 | P184 | K186 | | | | | | | |
| E137 | G138 | R139 | S140 | S141 | H142 | Q144 | R145 | Y147 | G148 | K149 | V150 | Q151 |

Figure 6A:
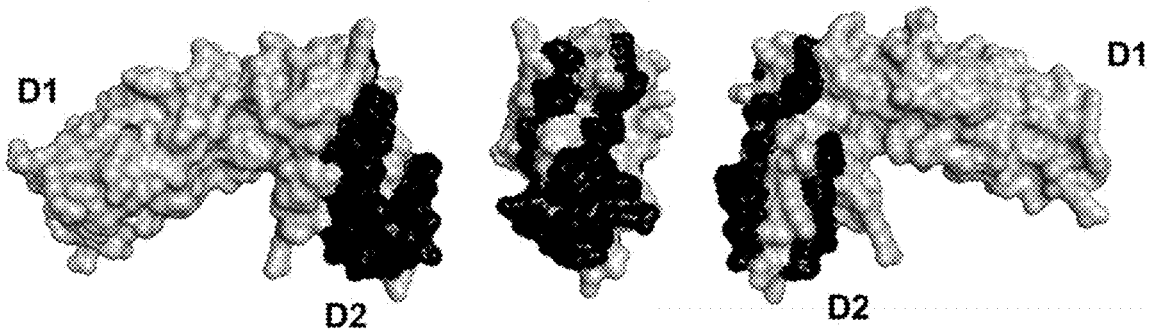
FIGS. 6A, 6B and 6C show the show the tertiary structure of NKp46 (in three orientations) on which the segments bound by antibodies 9H11A, 8B6A and 17E1 are represented, respectively.
Figure 6B:
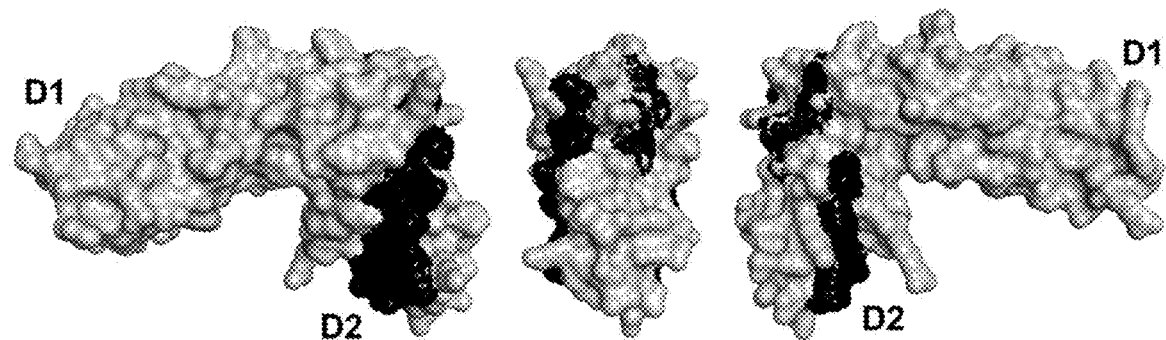
Figure 6C:
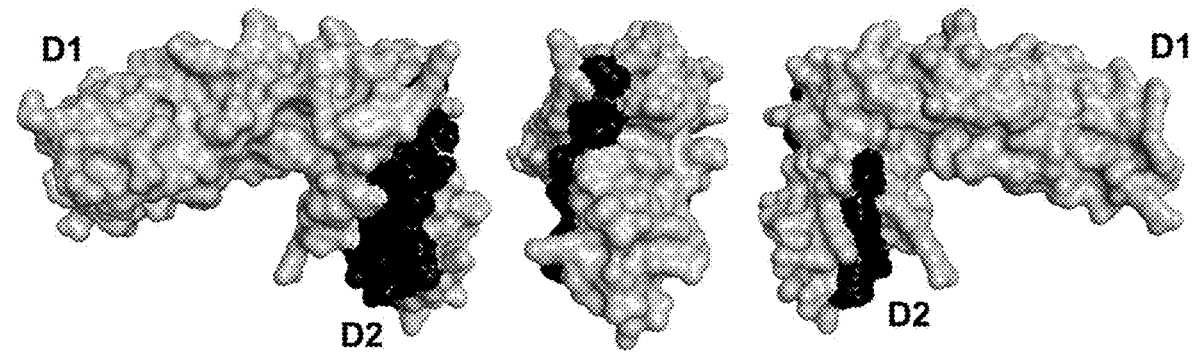

FIGS. 6A, 6B and 6C show the show the tertiary structure of NKp46 (in three orientations) on which the segments bound by antibodies 9H11A, 8B6A and 17E1 are represented, respectively. As shown, the antibodies bind to the D2 domain of NKp46.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as reference to an element or elements is intended to provide support for a similar aspect or embodiment of the invention that "consists of"," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

We claim:

1. A nucleic acid or set of nucleic acids encoding an antibody, an antibody fragment, or a protein comprising said antibody fragment, said nucleic acid encoding an antibody or antibody fragment selected from the group consisting of:
   (a) an antibody or antibody fragment comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;
   (b) an antibody or antibody fragment comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 21;
   (c) an antibody or antibody fragment comprising (i) a heavy chain comprising CDR 1, 2 and 3 of the heavy chain variable region of SEQ ID NO: 29 and (ii) a light chain comprising CDR 1, 2 and 3 of the light chain variable region of SEQ ID NO: 30;
   (d) an antibody or antibody fragment comprising (i) a heavy chain comprising CDR 1, 2 and 3 of the heavy chain variable region of SEQ ID NO: 29 and (ii) a light chain comprising CDR 1, 2 and 3 of the light chain variable region of SEQ ID NO: 47; and
   (e) an antibody or antibody fragment comprising (i) a heavy chain comprising CDR 1, 2 and 3 of the heavy chain variable region of SEQ ID NO: 55 and (ii) a light chain comprising CDR 1, 2 and 3 of the light chain variable region of SEQ ID NO: 56.

2. The nucleic acid or set of nucleic acids of claim 1, said nucleic acid or set of nucleic acids encoding an antibody or antibody fragment comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4.

3. The nucleic acid or set of nucleic acids of claim 1, said nucleic acid or set of nucleic acids encoding an antibody or antibody fragment comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 21.

4. The nucleic acid or set of nucleic acids of claim 1, said nucleic acid or set of nucleic acids encoding an antibody or antibody fragment comprising (i) a heavy chain comprising CDR 1, 2 and 3 of the heavy chain variable region of SEQ ID NO: 29 and (ii) a light chain comprising CDR 1, 2 and 3 of the light chain variable region of SEQ ID NO: 30.

5. The nucleic acid or set of nucleic acids of claim 1, said nucleic acid or set of nucleic acids encoding an antibody or antibody fragment comprising CDR 1, 2 and 3 of the heavy chain variable region of SEQ ID NO: 29 and (ii) a light chain comprising CDR 1, 2 and 3 of the light chain variable region of SEQ ID NO: 47.

6. The nucleic acid or set of nucleic acids of claim 1, said nucleic acid or set of nucleic acids encoding an antibody or antibody fragment comprising CDR 1, 2 and 3 of the heavy chain variable region of SEQ ID NO: 55 and (ii) a light chain comprising CDR 1, 2 and 3 of the light chain variable region of SEQ ID NO: 56.

7. The nucleic acid or set of nucleic acids of claim 1, said nucleic acid or set of nucleic acids encoding a protein comprising said antibody fragment.

8. The nucleic acid or set of nucleic acids of claim 7, said nucleic acid or set of nucleic acids encode a chimeric cell surface receptor protein comprising said antibody fragment.

9. A recombinant host cell comprising the nucleic acid of claim 1.

* * * * *